(12) United States Patent
Yun et al.

(10) Patent No.: US 11,174,465 B2
(45) Date of Patent: Nov. 16, 2021

(54) PH-SENSITIVE AND BIOREDUCIBLE POLYMER-VIRUS COMPLEX FOR CANCER TREATMENT

(71) Applicant: GENEMEDICINE CO., LTD., Seoul (KR)

(72) Inventors: Chae Ok Yun, Seoul (KR); Dayananda Kasala, Seoul (KR)

(73) Assignee: GENEMEDICINE CO., LTD., Seoul (KR)

( * ) Notice: Subject to any disclaimer, the term of this patent is extended or adjusted under 35 U.S.C. 154(b) by 531 days.

(21) Appl. No.: 15/331,619

(22) Filed: Oct. 21, 2016

(65) Prior Publication Data

US 2017/0119890 A1    May 4, 2017

Related U.S. Application Data

(63) Continuation-in-part of application No. PCT/KR2015/003685, filed on Apr. 13, 2015.

(51) Int. Cl.

| | |
|---|---|
| *C12N 7/00* | (2006.01) |
| *A61K 9/06* | (2006.01) |
| *A61K 47/26* | (2006.01) |
| *A61K 47/54* | (2017.01) |
| *A61K 47/60* | (2017.01) |
| *A61K 47/59* | (2017.01) |
| *A61K 47/64* | (2017.01) |
| *A61K 35/761* | (2015.01) |
| *A61K 9/00* | (2006.01) |
| *A61K 31/713* | (2006.01) |

(52) U.S. Cl.
CPC .............. *C12N 7/00* (2013.01); *A61K 9/0014* (2013.01); *A61K 9/06* (2013.01); *A61K 31/713* (2013.01); *A61K 35/761* (2013.01); *A61K 47/26* (2013.01); *A61K 47/542* (2017.08); *A61K 47/545* (2017.08); *A61K 47/59* (2017.08); *A61K 47/60* (2017.08); *A61K 47/645* (2017.08); *C12N 2710/10032* (2013.01); *C12N 2710/10042* (2013.01)

(58) Field of Classification Search
None
See application file for complete search history.

(56) References Cited

PUBLICATIONS

Lin et al (J Controlled Release 116:130-137, 2006) (Year: 2006).*
Wonganan et al (Viruses 2:468-502, 2010) (Year: 2010).*
Fisher et al., "Polymer-coated adenovirus permits efficient retargeting and evades neutralizing antibodies", Gene Therapy (2001) 8:341-348.
International Search Report for PCT/KR2015/003685, dated Jun. 30, 2015, 6 pages.
Kim et al., "The effect of surface modification of adenovirus with an arginine-grafted bioreducible polymer on transduction efficiency and immunogenicity in cancer gene therapy", Biomaterials 31 (2010):1865-1874.

* cited by examiner

*Primary Examiner* — Craig D Ricci
(74) *Attorney, Agent, or Firm* — Sughrue Mion, PLLC

(57) ABSTRACT

The present invention relates to a pH-sensitive and bioreducible polymer-virus complex which can destroy tumor cells more effectively by increasing the efficiency of virus transduction, to a pH-sensitive and bioreducible polymer, and to a pharmaceutical composition containing the polymer-virus complex.

5 Claims, 61 Drawing Sheets
Specification includes a Sequence Listing.

(B)

1-PBS
2-DNA
3-DNA/PPR 1 ug
4-DNA/PPR 2 ug
5-DNA/PPR 4 ug
6-DNA/peptide/PPR 1 ug
7-DNA/peptide/PPR 2 ug
8-DNA/peptide/PPR 4 ug

PH-SENSITIVE AND BIOREDUCIBLE POLYMER-VIRUS COMPLEX FOR CANCER TREATMENT

CROSS-REFERENCE TO RELATED APPLICATIONS

This application claims priority to and is a Continuation-In-Part of PCT/KR2015/003685 (WO2015/163622), filed on Apr. 13, 2015 entitled "PH-SENSITIVE AND BIO-REDUCTIVE POLYMER-VIRUS COMPOSITE FOR CANCER TREATMENT", which application claims priority to and the benefit of Korean Patent Application No. 10-2014-0048146, filed Apr. 22, 2014; the disclosures of which is incorporated herein by reference in their entirety.

SEQUENCE LISTING

Incorporated by reference herein in its entirety is the Sequence Listing entitled "Sequence listing_ST25.txt," created Oct. 21, 2016, size 7 kilobyte.

TECHNICAL FIELD

The present invention was made by Task No. 2013050188 under the support of the Ministry of Science, ICT and Future Planning in Korea, where the research management professional organization of the task was the National Research Foundation of Korea, the title of research project was "Science and Technology Internationalization Business/International Joint Research Project/Global Research Laboratory (GRL)," the title of research task was "development of drug delivery system of intelligent cancer cell killing gene for metastatic cancer diagnosis/treatment," the lead agency was Industry-University Cooperation Foundation Hanyang University and the research period was Sep. 1, 2013 Aug. 31, 2014.

The present invention was made by Task No. 2013065203 under the support of the Ministry of Science, ICT and Future Planning, where the research management professional organizations of the task was the National Research Foundation of Korea, the title of research project was "Science and Engineering Basic Research Business/Mid-career Researcher Support Project/Bottom-up Research," the title of research task was "development of nano-material hybrid gene delivery system for selective tumor control," the lead agency was Industry-University Cooperation Foundation Hanyang University and the research period was Sep. 1, 2013~Aug. 31, 2014.

The present patent application claims a priority of KR Patent Application No. 10-2014-0048146 filed in the Korean Intellectual Property Office on Apr. 22, 2014, the disclosure of which is incorporated by reference herein.

The present invention relates to a pH-sensitive and bioreducible polymer-virus complex which can destroy tumor cells more effectively by increasing the efficiency of virus transduction, to a pH-sensitive and bioreducible polymer, and to a pharmaceutical composition containing the polymer-virus complex.

BACKGROUND ART

During the past 50 years, the oncolytic adenovirus (Ad) has been suggested as therapeutic strategies due to its various biochemical advantages. These oncolytic adenoviruses establish, first, cancer-specificity; defense mechanism of replication viruses present in normal cells, for example an endogenous tumor suppressor protein (p53, pRb, p12ARF, etc.) does not represent a function in cancer cells, which establishes the selectivity of the adenovirus to the tumor. Adenoviruses not only destroy hosts directly at the end of the lytic cycle, but also diffuse progeny viruses, which also infect the neighboring tumor cells and then destroy them. The adenovirus is one of the most effective viral vectors in gene therapy as well as the oncolytic properties. The adenovirus has high gene transfer efficiency in dividing cells and non-dividing cells, and an effective nucleic acid entry mechanism and titer. Consequently, various clinical trials have been successfully reported using the topical administration of adenoviruses for tumor gene therapy.

However, adenoviruses face a number of challenges in realizing a maximum therapeutic effect in systemic administration in spite of the preferred features. Adenoviruses are removed from blood vessels through the following three major immunological barriers on being systemically delivered: 1) the innate immune reaction induced by macrophages and dendritic cells, 2) the adaptive immune reaction due to neutralization of anti-adenovirus antibodies 3) collection of virus particles by the Kupffer cells. Three immunological barriers cause acute liver toxicity and infection of liver cells. Also, adenoviruses interact with platelets and red blood cells, and these lead to toxicity and other possible side effects. The transduction efficiency of adenoviruses is severely limited by the expression level of CAR (coxsackie and adenovirus receptor) in tumor cells as well as the immunological barriers. CAR is an inner membrane-permeable protein of 46 kDa acting as the primary entrance that adenoviruses enter into the target cells. An adenovirus penton base interacts with, especially, $\alpha_v\beta_3$ and $\alpha_v\beta_5$ using an Arg-Gly-Asp (RGD) motif. This leads to the formation of clathrin-coated pits to facilitate internalization of viruses inside endosomes. The therapeutic effect of intratumor and systemic administration by adenoviruses may be compromised by the low expression level of CAR in the tumor cells because of such dependence.

In using a viral vector, one strategy designed to overcome the intrinsic biochemical and immunological barrier is the development of "smart" adenovirus nano complexes through surface modification of viruses having non-viral systems. Non-viral systems have unique advantages, such as low immunogenicity, effective reproductive property and simple quality control process. These advantages compensate for the limitations of the above-mentioned viral vectors. As a result, a variety of adenovirus nano complexes have been developed in order to minimize the targeting efficiency while minimizing harmful side effects. For example, polyethylene glycol (PEG) is one of major polymers coupling with adenoviruses to reduce the hepatic uptake and extend the half-life thereof in the blood circulation. In addition, it was demonstrated that polyethylene glycolation of adenoviruses not only reduces the innate immune reaction to adenoviruses, but also inhibits neutralizing adenoviruses by host antibodies.

Adenovirus encapsulation using a cationic polymer is another effective strategy to overcome the CAR dependence and the immunological barriers. Because cell membranes and adenoviruses all have negative charges, the positive charges of the polymer not only allow ionic interaction between the polymer and the viruses, but also facilitate the entry into the host cells of the viruses using the electrostatic interaction. To handle this problem, poly (ethylimine) (PEI) and poly(L-lysine) (PLL) became 22 most standard cationic polymers used for improving the transduction efficiency of adenovirus and DNA delivery. However, the adenoviruses coated with these polymers remain in an insufficient state in terms of tumor selectivity-selective because of non-specific uptake by positive charges. In addition, such a cationic polymer causes severe cytotoxicity due to in-vivo undegradability and the strong uptake of the polymer having positive charges and the cell membrane having negative charges, and this cytotoxicity is due to the cytotoxicity mediated by PEI and PLL (see in vitro cytotoxicity test of multiple cation: cell viability and impact of hemolytic-PLL).

Recently, interest in developing tumor nanoparticles/nanomaterials of tumor hypoxia reactive polymers for the tumor targeting delivery of genes and drugs has increased. Furthermore, hypoxia induces two typical biological responses, that is, stabilization of hypoxia-induced factor-1 and the accelerated bioreducible reaction. Also, hypoxia is a diseased state and the tissues of this state are derived of the supply of oxygen to show significantly adverse effects on gene therapy as well as chemotherapy of cancer treatment. Because of high rate aerobic and anaerobic glycolysis induced by the hypoxia state, lactic acid is accumulated in the extracellular environment, which is finally acidic compared to the normal physiological pH (7.4). Therefore, the "smart" nano complexes targeting specific aspects of the tumor microenvironment including the extracellular pH may be developed as a tumor-selective and safe vector system. In this regard, a number of stimulus-sensitive polymers have been developed, and their working mechanism is based on the chemical structure of the polymer. For example, the polymer having acidic or basic groups exhibits a reaction with a pH solution. To develop a pH-reactive system, an acidic residue, such as a carboxylic acid or a basic residue, such as a quaternary amine is incorporated into a copolymer. However, the number of the system which reacts in a physiologically accessible pH range (pH 4.5-7.4) is very limited. Recently, in pH reactive drug delivery systems, those reported on the basis of some charge conversion polymer, e.g., poly(histidine) and poly (beta-aminoester) are the minority. In these studies, the present inventors have devised and synthesized the pH-sensitive polymer (mPEG-PiP-CBA) (CBA) with bioreducible disulfide linkages on the polymer backbone. Furthermore, the present inventors studied the in vitro transduction efficiency and the cellular uptake of the Ad-CBA.

A number of literatures and patent documents are referenced throughout the present specification, and their citations are shown in parentheses. The disclosures of the cited literatures and patent documents are incorporated by reference herein in their entireties to explain the level of the technical field to which the present invention pertains and the content of the present invention more clearly.

DETAILED DESCRIPTION OF INVENTION

Technical Problem

The present inventors have devised and synthesized the pH-sensitive polymer (mPEG-PiP-CBA) (CBA) having bioreducible disulfides linkage on the polymer backbone, and further studied the in vitro transduction efficiency and the cellular uptake of Ad-CBA, so that the present invention has been accomplished by confirming the fact that the pH-sensitive and bioreducible polymer-virus complex has an excellent effect of anticancer treatment.

Therefore, it is the object of the present invention to provide a polymer-virus complex that a pH-sensitive and bioreducible polymer is bonded to the surface of virus.

It is another object of the present invention to provide a pharmaceutical composition for anticancer treatment comprising the polymer-virus complex.

It is yet another object of the present invention to provide a pH-sensitive and bioreducible polymer comprising (i) an escapable portion from immune reactions, (ii) a chargeable portion and (iii) a bioreducible portion including disulfide linkages.

It is yet another object of the present invention to provide a method of anticancer treatment comprising a step of administering a therapeutically effective amount of a polymer-virus complex to a subject.

The objects and advantages of the invention will become apparent by the detailed description of invention and claims below.

Technical Solution

According to one aspect of the present invention, the present invention provides a polymer-virus complex that a pH-sensitive and bioreducible polymer is bonded to the surface of virus, which comprises (i) an escapable portion from immune reactions, (ii) a chargeable portion and (iii) a bioreducible portion including disulfide linkages.

The polymer used in the complex of the present invention is prepared to contain three portions. And the three portions include (i) an escapable portion from immune reactions, (ii) a chargeable portion and (iii) a bioreducible portion including disulfide linkages, respectively.

The escapable portion from immune reactions acts to be capable of avoiding in vivo immune reactions (including cellular immune reactions and humoral immune reactions) by the virus binding the polymer. A material that may be used for the escapable portion from immune reactions is, specifically, a polymer which may avoid in vivo immune reactions (including cellular immune reactions and humoral immune reactions), more specifically, PEG (polyethylene glycol), polyalkylene oxide [for example, polyoxyethylene, polyoxypropylene, or a copolymer thereof (e.g., polyethylene oxide-polypropylene oxide-polyethylene oxide copolymer)], polyphenylene oxide, a copolymer of PEG and polyalkylene oxide, poly (methoxyethyl methacrylate), poly (methacryloyl phosphatidylcholine), perfluorinated polyether, dextran, or polyvinylpyrrolidone, more specifically, PEG, polyalkylene oxide or a copolymer of PEG and polyalkylene oxide, and more further specifically PEG.

The chargeable portion of the polymer used in the present invention may give the polymer charges (for example, positive charges) at the in vivo pH, specifically about neutral pH to be bonded to the surface of virus (for example, negatively charged surface of adenovirus) by ionic interactions. The chargeable portion comprises a material to give positive charges or negative charges to the polymer, for which a material, for example, having a carboxylate group in the case of providing negative charges or a tertiary amine group or an amino group in the case of providing positive charges may be used, and for example, include 1-(2-aminoethyl)piperazine, 4-(aminomethyl)piperidine, N-methylethylenediamine, N-ethylethylenediamine, N-hexylethylenediamine, dimethyldipropylenetriamine or imidazole, without being limited thereto.

The bioreducible portion including disulfide linkages comprises any material including disulfide linkages. The bioreducible portion is reduced under in vivo acidic environment to convert the disulfide linkage into a sulfhydryl group and thus to form fracture of the polymer structure, and the bonded virus is finally released (naked virus), and for example, may include N,N-cystaminebisacrylamide, disulfide based diacrylate, or N,N-cystaminebis(acrylamide), without being limited thereto.

Most specifically, the polymer used in the complex of the invention is represented by Formula 1 below:

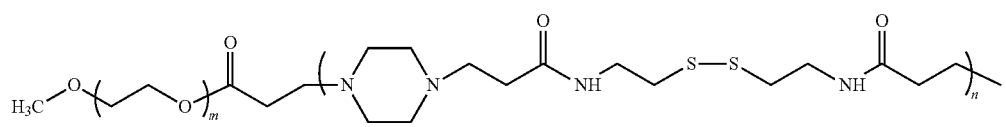

Formula 1 wherein, m and n are independently an integer of 1 to 6.

Furthermore, in one embodiment of the present invention, to maximize the cell transfer efficiency of Ad plasmid DNA, it may be established in a form additionally bonded by PEI-Arg (polyethyleneimine-arginine) at the end of the reducible portion of said polymer.

The virus used in the polymer-virus complex comprises any virus, specifically a virus used for gene therapy, for example as follows:

i. Adenovirus

An adenovirus has been widely used as a gene transfer vector because of genome size of moderate degree, ease of operation, high titer, wide target cells and excellent infection. Both ends of the genome comprise an ITR (inverted terminal repeat) of 100-200 bp, which is a cis element essential for DNA replication and packaging. An E1 region of the genome (E1A and E1B) encodes proteins that regulate the transcription and the transcription of the host cell gene. An E2 region (E2A and E2B) encodes proteins involved in the viral DNA replication.

Among the currently developed adenovirus vectors, replication-incompetent adenoviruses lacking the E1 region are largely used. Furthermore, an E3 region is removed from a usual adenovirus vector to provide a seat which is inserted by a foreign gene (Thimmappaya, B. et al., Cell, 31:543-551 (1982); and Riordan, J. R. et al., Science, 245: 1066-1073 (1989)). Therefore, the decorin gene of the present invention is preferably inserted into the deleted E1 region (E1A region and/or E1B region, preferably E1B region) or the deleted E3 region, and more preferably inserted into the E3 region. Moreover, the desired nucleotide sequence intended to be carried in cells is preferably inserted into the deleted E1 region (E1A region and/or E1B region, preferably E1B region), and more preferably inserted into the E1 region. The term "deleted" as used herein with respect to the virus genome sequence has a meaning that the corresponding sequence includes the partially deleted sequence as well as the completely deleted sequence.

In addition, since the adenovirus can pack up to about 105% of the wild-type genome, it can further package about 2 kb (Ghosh-Choudhury et al., EMBO J., 6:1733-1739 (1987)). Therefore, the above-mentioned foreign sequence to be inserted into the adenovirus may be additionally combined to the genome of the adenovirus.

The adenovirus has 42 different serotypes and A-F subgroups. Among them, the adenovirus type 5 belonging to the subgroup C is the most preferred starting material for obtaining the adenovirus vector of the present invention. Biochemical and genetic information for the adenovirus type 5 are well known.

The foreign gene carried by the adenovirus is replicated in the same way as an episome, and thus the genetic toxicity for the host cell is very low. Accordingly, it is expected that the gene therapy using the adenovirus gene delivery system of the present invention will be highly safe.

ii. Retrovirus

Because a retrovirus is subjected to inserting its gene into a genome of host, is capable of carrying a large amount of foreign genetic materials and has a wide spectrum of cells which may be infected, it has been largely used as a gene transfer vector.

For establishing a retrovirus vector, the decorin gene and the desired nucleotide sequence intended to be carried are inserted into the retrovirus genome instead of the retrovirus sequence to produce a replication-incompetent virus. To produce a virion, a packaging cell line is established, which includes gag, pol and env genes, but do not include the LTR (long terminal repeat) and ψ sequence (Mann et al., Cell, 33:153-159 (1983)). If a recombinant plasmid including the decorin gene, the desired nucleotide sequence intended to be carried, LTR and ψ sequence is transferred in the cell line, the ψ sequence allows to produce an RNA transcript of the recombinant plasmid, this transcript is packaged in a virus, and the virus is discharged into a medium (Nicolas and Rubinstein "Retroviral vectors," in: vectors: A survey of molecular cloning vectors and their uses, Rodriguez and Denhardt (eds.), Stoneham: Butterworth, 494-513 (1988)). The medium containing the recombinant retroviruses is collected and concentrated to use as a gene delivery system.

The gene transfer using the second generation retrovirus vector was announced. Kasahara et al. (Kasahara et al. Science, 266: 1373-1376 (1994)) prepared a variant of Moloney murein leukemia virus (MMLV), where the EPO (erythropoietin) sequence was inserted into the envelope site to produce chimeric proteins having new binding properties. The gene delivery system of the present invention can be prepared in accordance with the implementation strategy of such second generation retrovirus vectors.

iii. AAV Vector

Because the adeno-associated virus (AAV) has a capability which can infect non-dividing cells and be infected by various types of cells, it is suitable as a gene delivery system of the present invention. The detailed description for preparation and use of the AAV vector has been disclosed in detail in U.S. Pat. Nos. 5,139,941 and 4,797,368.

Studies on AAV as a gene transfer system have been disclosed in LaFace et al., Viology, 162:483486 (1988); Zhou et al., Exp. Hematol. (NY), 21:928-933 (1993); Walsh et al., J. Clin. Invest., 94:1440-1448 (1994); and Flotte et al., Gene Therapy, 2:29-37 (1995). Recently, the AAV vector is conducted under clinical I as a therapeutic agent of cystic fibrosis.

Typically, the AAV virus is prepared by co-transforming a plasmid (McLaughlin et al, J. Virol., 62: 1963-1973 (1988); and Samulski et al., J. Virol., 63:3822-3828 (1989)) comprising the desired gene sequence (the decorin gene and the desired nucleotide sequence intended to be carried)

where two AAV terminal repeats are located and an expression plasmid (McCarty et al., *J. Virol.*, 65: 2936-2945 (1991)) comprising a wild-type AAV coding sequence without any terminal repeat.

iv. Other Viral Vectors

Other viral vectors may be also used in the present invention. Vectors derived from vaccinia virus (Puhlmann M. et al., *Human Gene Therapy* 10:649-657 (1999); Ridgeway, "Mammalian expression vectors," In: *Vectors: A survey of molecular cloning vectors and their uses*. Rodriguez and Denhardt, eds. Stoneham: Butterworth, 467-492 (1988); Baichwal and Sugden, "Vectors for gene transfer derived from animal DNA viruses: Transient and stable expression of transferred genes," In: Kucherlapati R, ed. *Gene transfer*. New York: Plenum Press, 117-148 (1986) and Coupar et al., *Gene*, 68:1-10 (1988)), lentivirus (Wang G. et al., *J. Clin. Invest.* 104 (11): R55-62 (1999)) or herpes simplex virus (Chamber R., et al., *Proc. Natl. Acad. Sci USA* 92:1411-1415 (1995)) can be also used in the present invention.

The virus used in the present invention can additionally include the following therapeutic gene: the form that the therapeutic gene is included in the complex may be restricted, and as an example, be a virus having or modified to have a therapeutic effect by itself, or include a form combined or supported to the virus of the complex of the present invention, without being limited thereto. In one embodiment, the therapeutic gene may be a cancer therapeutic gene indicating the therapeutic effect on expressing in the cancer cells, and specifically, include a drug-sensitizing gene, a tumor suppressor gene, an antigen gene, a cytokine gene, a cytotoxic gene, a cytostatic gene, a pro-apoptotic gene, an antibody gene, a metastasis-suppressing gene and an anti-angiogenic gene, but is not limited thereto.

The term "antigenic gene" herein means the nucleotide sequence to produce cell surface antigenic proteins which may be expressed in target cells and recognized by the immune system. Examples of such antigenic genes include carcinoembryonic antigen (CEA) and PSA (prostate specific antigen), AFP (α-feto protein), and p53 (WO 94/02167). In order to easily recognize the immune system, the antigenic gene can be coupled to MHC type I antigen.

The term "cytotoxic gene" herein refers to a nucleotide sequence which is expressed in cells to show a toxic effect. Examples of such a cytotoxic gene include nucleotide sequences encoding *Pseudomonas* exotoxin, ricin toxin, diphtheria toxin and the like.

The term "cytostatic gene" herein refers to a nucleotide sequence which is expressed in cells to stop a cell cycle during the cell cycles. Examples of such a cytostatic gene include p21, retinoblastoma gene, E2F-Rb fusion protein gene, genes encoding cyclin-dependent kinase inhibitors (for example, p16, p15, p18 and p19), growth arrest specific homeobox (GAX) gene (WO 97/16459 and WO 96/30385), and the like, without being limited thereto.

In addition, many therapeutic genes that may be usefully used in the treatment of various diseases are also carried by the system of the present invention. For example, genes encoding cytokines (e.g., interferon-alpha, -beta, -delta and -gamma), interleukins (e.g., IL-1, IL-2, IL-4, IL-6, IL-7, IL-10, IL-12, IL-19 and IL-20) and colony stimulating factors (for example, GM-CSF and G-CSF), and chemokine groups (monocyte chemotactic protein 1 (MCP-1), monocyte chemotactic protein 2 (MCP-2), monocyte chemotactic protein 3 (MCP-3), monocyte chemotactic protein 4 (MCP-4), macrophage inflammatory protein 1α (MIP-1α), macrophage inflammatory protein 1β (MIP-1β), macrophage inflammatory protein 1γ (MIP-1γ), macrophage inflammatory protein 3α (MIP-3α), macrophage inflammatory protein 3β (MIP-3β), chemokine (ELC), macrophage inflammatory protein 4 (MIP-4), macrophage inflammatory protein 5 (MIP-5), LD78β, RANTES, SIS-epsilon (p500), thymus activation-regulated chemokine (TARC), eotaxin, I-309, human protein HCC-1/NCC-2, human protein HCC-3, mouse protein C10, etc.) are included. In addition, genes expressing tissue plasminogen activator (tPA) or urokinase and LAL generating genes to prevent hypercholesteremia by providing the sustained thrombotic effect are included. In addition, various polynucleotides for the treatment of viral, malignant and inflammatory diseases and conditions, such as cytic fibrosis, adenosine deaminase deficiency and AIDS are known.

The term "pro-apoptotic gene" herein refers to a nucleotide sequence which is expressed to induce the programmed apoptosis. Examples of such a pro-apoptotic gene include p53, adenovirus E3-11.6K (derived from Ad2 and Ad5) or adenovirus E3-10.5K (derived from Ad), adenovirus E4 gene, Fas ligand, TNF-, TRAIL, p53 pathway genes and genes encoding caspases.

In the specification of the present invention, the term "antibody gene" means a nucleotide sequence producing a specific antibody which can induce apoptosis of cancer cells by coupling antigens preferentially or exclusively expressed in cancer cells, unlike normal cells. An example of such a gene includes a nucleotide sequence encoding anti-DR4/DR5, anti-CTLA-4, anti-PD-1, anti-PD-L1, anti-Her2/neu, anti-VEGF, anti-VEGFR, anti-cMet, anti-Survivin, anti-EGFR, anti-Wnt, anti-Ly49, and the like.

In the specification of the present invention, the term "metastasis-suppressing gene" is a gene suppressing metastasis by movement and infiltration of cancer cells, and for example includes BRMS1, CRSP3, DRG1, KAI1, KISS1, NM23, and various TIMPs (Tissue inhibitors of metalloproteinase).

The term "anti-angiogenic gene" herein refers to a nucleotide sequence which is expressed to release anti-angiogenic factors out of the cells. In the anti-angiogenic factors, angiostatin, an inhibitory factor of vascular endothelial growth factor (VEGF) such as Tie 2 (PNAS, 1998, 95, 8795-800), endostatin, etc. are included.

According to another aspect of the invention, the present invention provides a pharmaceutical composition for anti-cancer treatment comprising (a) a therapeutically effective amount of the above described polymer-virus complex of the present invention; and (b) a pharmaceutically acceptable carrier.

The pharmaceutical composition of the present invention uses the above described polymer-virus complex as an effective component, and thus the common contents between these two are omitted in order to avoid undue complexity of this specification.

Furthermore, one embodiment of the present invention may be established in a form additionally combined by PEI-Arg (polyethyleneimine-arginine) at the end of the reductible portion of the polymer. In addition, a peptide for enhancing the endosomal escape efficiency may be further contained, and the peptide may preferably consist of SEQ ID NO: 1, but the peptide representing activity equivalent to this may be included without limitation.

Although the above described polymer-virus complex of the present invention may be utilized in the treatment of various diseases, it is particularly useful for anticancer treatment.

Since the polymer-virus complex contained in the composition of the present invention exhibits a killing efficacy against various tumor cells, as described above, the pharmaceutical composition of the present invention may be used in the treatment of various diseases or disorders associated with tumors, such as gastric cancer, lung cancer, breast cancer, ovarian cancer, liver cancer, bronchial cancer, nasopharyngeal cancer, laryngeal cancer, pancreatic cancer, bladder cancer, colon cancer, cervical cancer, non-small cell bone cancer, skin cancer, head or neck cancer, uterine cancer, rectal cancer, perianal cancer, colon cancer, fallopian tube cancer, endometrial cancer, vaginal cancer, vulva cancer, Hodgkin's disease, esophagus cancer, small intestine cancer, endocrine cancer, thyroid cancer, parathyroid cancer, adrenal cancer, soft tissue sarcoma, urethra cancer, penile cancer, prostate cancer, chronic or acute leukemia, lymphocytic lymphoma, kidney or ureter cancer, renal cell carcinoma, renal pelvic carcinoma, central nervous system (CNS) tumor, primary central nervous system lymphoma, spinal tumor, brain stem glioma or pituitary adenoma. The term "treatment" herein means (i) prevention of tumor cell formation; (ii) inhibition of diseases or disorders associated with tumors according to removal of tumor cells; and (iii) mitigation of diseases or disorders associated with tumors according to removal of tumor cells. Accordingly, the terms "therapeutically effective amount" herein means an amount sufficient to achieve the pharmacological effects described above.

The pharmaceutically acceptable carrier contained in the composition of the present invention, which is one usually used on formulating, includes lactose, dextrose, sucrose, sorbitol, mannitol, starch, gum acacia, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate and mineral oil, and the like, but is not limited thereto. The pharmaceutical composition of the present invention may further include a lubricant, a humectant, a sweetener, a flavoring agent, an emulsifier, a suspending agent, a preservative, and the like, in addition to the above components.

The pharmaceutical composition of the present invention can be administered, preferably, parenterally, for example intravenously, intraperitoneally, intramuscularly, subcutaneously or locally. It can be administered by an injection method in the case of being administered intraperitoneally in ovarian cancer and portally in liver cancer, administered by direct injection into the tumor mass in the case of breast cancer, administered by direct injection through enema in the case of colon cancer, and administered by direct injection into a catheter.

A suitable dose of the pharmaceutical composition of the present invention varies depending on factors such as formulation method, dosing regimen, patient age, body weight, sex, degree of disease symptom, food, administration time, administration route, excretion rate and response sensitivity factors, and the normal skilled physician can readily determine and prescribe an effective dosage for the intended treatment. In general, the pharmaceutical composition of the present invention comprises $1\times10^5$-$1\times10^{15}$ pfu/ml of polymer-virus complex, where $1\times10^{10}$ pfu is usually injected once every two days for two weeks.

The pharmaceutical compositions of the present invention may be prepared in a unit dosage form or a form introduced into a multidose container by being formulated with a pharmaceutically acceptable carrier and/or excipient, according to a method that person having ordinary knowledge in the art to which the present invention belongs can easily carry out. At this time, the dosage form may be a solution, suspension or emulsion form in an oil or aqueous medium, or also an extract, powder, tablet or capsule form, and additionally include a dispersant or a stabilizer.

Although the pharmaceutical composition of the present invention can be used as a monotherapy, it may be used together with other usual chemotherapy or radiation therapy, and when performing this combination therapy, it is possible to more effectively treat cancers. Chemotherapeutic agents that may be used with the composition of the present invention include cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastin, methotrexate, and the like. Radiation therapy that can be used with the composition of the present invention is the X-ray irradiation and γ-ray irradiation, and the like.

According to another aspect of the present invention, the present invention provides a polymer that the pH-sensitive and bioreducible polymer may be bonded to the surface of virus, which comprises (i) an escapable portion from immune reactions, (ii) a chargeable portion and (iii) a bioreducible portion including disulfide linkage.

The polymer of the present invention that may be bonded to the surface of virus is defined by Formula 1 as follows, and since it is used as an effective component of the above described polymer-virus complex, the common contents between these two are omitted in order to avoid undue complexity of this specification.

Formula 1

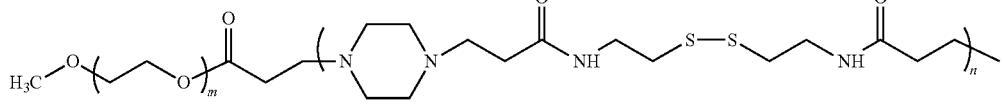

According to another aspect of the invention, the present invention provides a method of anticancer treatment comprising a step of administering a therapeutically effective amount of the polymer-virus complex of the present invention to a subject.

Since the method of anticancer treatment of the present invention corresponds to a method of using the polymer-virus complex or the composition for anticancer treatment using the same, which is another aspect of the present invention, the overlapping contents are omitted in order to avoid undue complexity of the specification.

In one embodiment of the present invention, the cancer in the method of anticancer treatment is any one selected from the group consisting of gastric cancer, lung cancer, breast cancer, ovarian cancer, liver cancer, bronchial cancer, nasopharyngeal cancer, laryngeal cancer, pancreatic cancer, bladder cancer, colon cancer, cervical cancer, non-small cell bone cancer, skin cancer, head or neck cancer, uterine cancer, rectal cancer, perianal cancer, colon cancer, fallopian tube cancer, endometrial cancer, vaginal cancer, vulva cancer, Hodgkin's disease, esophagus cancer, small intestine cancer, endocrine cancer, thyroid cancer, parathyroid cancer, adrenal cancer, soft tissue sarcoma, urethra cancer, penile cancer, prostate cancer, chronic or acute leukemia, lymphocytic lymphoma, kidney or ureter cancer, renal cell carcinoma, renal pelvic carcinoma, central nervous system (CNS) tumor, primary central nervous system lymphoma, spinal tumor, brain stem glioma and pituitary adenoma.

Effects of Invention

As explained in detail above, the present invention provides the pH-sensitive and bioreducible polymer-virus complex, the pH-sensitive and bioreducible polymer, and the pharmaceutical composition for anticancer treatment comprising the polymer-virus complex. The polymer of the present invention may be usefully used as a formulation for anticancer treatment that can destroy more effectively tumor cells by increasing the absorption efficiency into tissues and tumor cells and the transduction efficiency of adenoviruses through the immune evasion mechanism.

BRIEF DESCRIPTION OF DRAWINGS

FIG. 1A is a diagram showing a schematic description of synthesis of the pH-sensitive and bioreducible polymer (CBA).

FIG. 1B is a diagram showing the $^1$H-NMR spectrum of the CBA polymer in the CBA polymer lean $D_2O$.

FIG. 1C is a diagram showing hypothesis of Ad/CBA accumulation in tumor sites and Ad release from the polymer under the microenvironment.

FIG. 1D is a diagram evaluating the cytotoxicity of the CBA polymer in MCF-7 cells by the MTT assay.

FIG. 1E is a diagram measuring the zeta potential values of the CBA coated with Ad in various concentrations of CBA polymer, in 1 mL PBS, $1 \times 10^{10}$ VP and under the room temperature condition) mL PBS shown a also a (CBA polymer concentrations were shown. After repeated three times, data were shown as mean±SD).

FIG. 3A is a view showing fluorescent images of cells treated with Ad-CBA CBA complex in various concentrations of CBA. This is a view showing U343 and MCF7-mot cells transduced with the naked type Ad or Ad/CBA complex (0.05, 0.1, 0.25 and 0.5 mg/mL) at MOI 20 (U343) (FIG. 3A) and MOI 200 (FIG. 3B). Using various concentrations of CBA polymer, the gel retardation assay of the Ad-CBA complex was shown.

FIG. 4A is a view showing transduction into U343 cells with Ad and Ad-CBA in the presence and absence of a CAR specific fiber protein (0.2, 2 µg/ml). The naked type Ad and Ad-CBA was added at MOI 20. The cells were analyzed for GFP expression by the flow cytometry, 48 hours after transduction. Data are representative values of three independent repeated experiments (mean±standard error, ***P<0.001 vs. untreated group). In FIG. 4B, to identify the cellular uptake mechanism of the indicated concentration of the naked type Ad or Ad-CBA complex, the cells were pretreated for 30 min at the indicated concentrations. After that, the naked type Ad or Ad-CBA was added in the presence or absence of an inhibitor for an additional 2 hours. Then, the Ad or Ad-CBA was removed, and the cells were cultured for 24 hours after replacing with a fresh medium. GFP expression levels were observed by a fluorescence microscope and a flow cytometer (primary magnification: 100. The bar represents the mean±standard error, *P<0.05 and **P<0.01 vs. untreated group).

In FIG. 6A, the U343 cells were treated with PBS, RdB/shVEGF or RdB/shVEGF-CBA complex at 1 and 10 MOI. This is a diagram showing VEGF concentrations measured from the culture supernatants 24 hours after being infected by ELISA. In FIG. 6B, U343 and MCF7 cells were treated with PBS, RdB/shVEGF, or RdB/shVEGF-CBA complex. After 48 hours, the cell viability was evaluated by MTT assay. The untreated group was set to 100%. Data are means and SDs of three times repeated experiments. The bar means the mean±standard error (*P<0.05, ***P<0.001, the naked type RdB/shVEGF-treatment group).

FIG. 7A is a view showing the martrigel plug slice with an anti-CD31 antibody by an immunohistochemical staining method (primary magnification: ×200, bars are mean±SE, blood vessel per group*, ***P<0.001, at pH 7.4 RdB/shVEGF or RdB/shVEGF-CBA). FIG. 7B is a view showing the anti-cancer therapeutic effect of the naked type Ad or Ad-CBA complex in the U87 xenografted by U87 glioblastoma of a nude mouse through intratumor injection. The subcutaneous tumor transplanted from the U87 cells was treated with PBS, RdB/shVEGF ($5 \times 10^9$ VP) or RdB/shVEGF-CBA ($5 \times 10^9$ VP) complex. The tumor volume was measured every 2 days after treatment as follows. Bars represent mean±standard error (*P<0.05, ***P<0.001, naked type RdB/shVEGF-treated group).

FIG. 8A is a diagram showing transduction of anti-inflammatory cytokine IL-6. This is a diagram showing IL-6 levels measured by ELISA from sera obtained 6 hours after intravenously injecting $1 \times 10^{10}$ VP of the naked type Ad and Ad-CBA into a mouse. FIG. 8B is a diagram showing ALT and AST serum levels measured after intravenous administration of $1 \times 10^{10}$ VP of Ad or Ad-CBA (data represent mean±standard error and n=3 per each experiment condition; **P<0.01, naked type Ad-treated group).

FIG. 23A is a result of quantifying the number of viral particles, and FIG. 23B is a result showing the cancer cell viability.

FIG. 24A is a result of quantifying the number of viral particles, and FIG. 24B is a result showing the cancer cell viability.

FIG. 30A is a result confirmed by H & E staining, and FIG. 30B is a result confirmed by TUNEL assay.

FIG. 35A is a result visually determining change of the liver size, and FIG. 35B is a result measuring the weight of liver.

FIG. 36A is a result visually determining the sizes of spleen and lymph nodes, FIG. 36B is a result measuring the weight of spleen.

FIG. 37A is a result visually determining change of the thymus size, and FIG. 37B is a result measuring the weight of thymus.

MODE FOR CARRYING OUT INVENTION

Figure 1A:
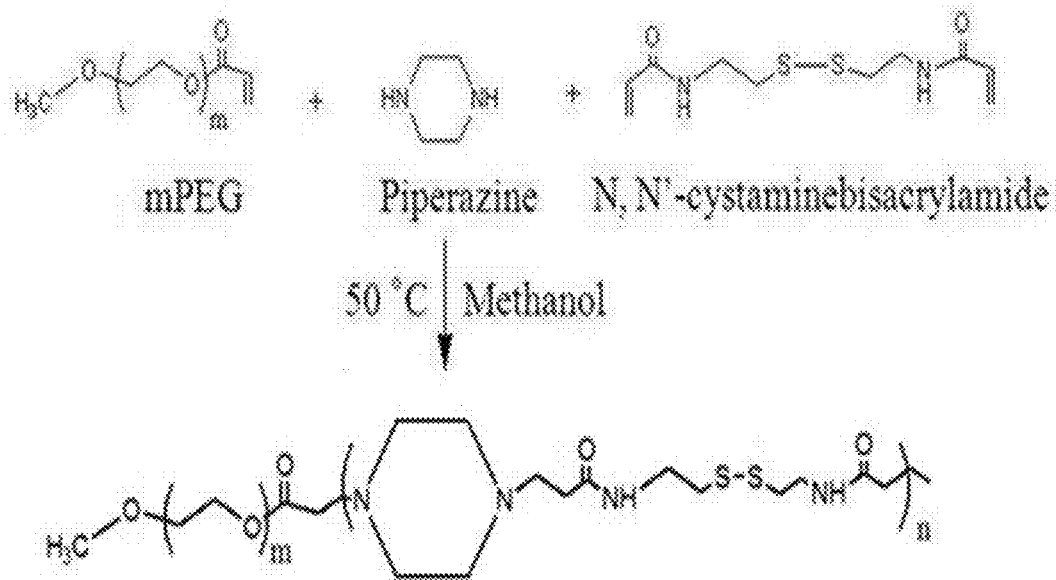
FIGS. 1A, 1B, 1C, 1D, and 1E are diagrams showing a schematic description investigating the Ad-CBA structure and characteristic.

Hereinafter, the present invention will be explained in more detail through examples. These examples are to explain only the present invention in more detail, where it will be apparent to person having ordinary knowledge in the art that the scope of the present invention according to the subject matter of the present invention is not restricted by these examples.

Example

I. pH-Sensitive and Bioreducible Polymer (CBA) and Ad-CBA Complex
Materials and Experimental Methods
1. Cell Culture and Cell Generation of Adenovirus (Ad)
Cell lines used in experiments of the present invention were cultured in Dulbecco's modified Eagle's medium (DMEM; GIBCO-BRL, Grand Island, N.Y.) adding 10% fetal bovine serum (FBS) (GIBCO-BRL) at 37° C. under 5%

$CO_2$ dry atmosphere state. Human embryonic kidney cell line (HEK293), human brain tumor cell line (U343, U87) and human breast tumor cell line, expressing the Ad E1 region, were obtained from American Type Culture Collection (ATCC, Manassas, Va.). The in vitro adenovirus gene transfer efficiency was examined using a GFP expressing replication-incompetent Ad (dE1/GFP). Generation of replication-competent Ad (RdB/shVEGF) mutated in the E1A site and deleted in the E1B site was characterized by dE1/GFP, and RdB/shVEGFs were grew in HEK293 cells and purified by the CsCl concentration gradient method. The number of viral particles (VP) was calculated, where 1 absorbance unit in OD 260 is equal to $10^{12}$ VP/mL. The purified viruses were stored at −80° C. until use. Meanwhile, two target shRNA sequences for VEGF were selected using a dedicated program provided by Ambion Inc. Two double-stranded RNA oligonucleotides, corresponding to two region at nucleotides 124-144 (shVEGF1), and 379-399 (shVEGF-2) of human VEGF mRNA (Genbank accession no. GI6631028).

2. Synthesis of pH-Sensitive and Bioreducible Polymer (CBA)

The pH-sensitive polymer was synthesized through a Michael type reaction polymerization. In summary, mPEG-acrylate ($M_n$=2.0 kDa, 0.10 mmol) (Sigma-Aldrich, St. Louis, Mo., USA) and N,N'-cystaminebisacrylamide (1.0 mmol) (PolySciences Inc, Warrington, Pa.) were dissolved in methanol (5.0 mL). After that, piperazine (1.0 mmol) (Sigma-Aldrich, St. Louis, Mo., USA) was added and then the reaction mixture was stirred at 50° C. in the darkroom condition under nitrogen for 48 hours. After the reactant up to room temperature, the polymer was precipitated in diethyl ether. The precipitated polymer was dried at room temperature in a vacuum for two days. Finally, the polymer was characterized by $^1$H NMR (Mercury plus 300 MHz, Varian Inc., USA), where the molecular weight calculated on the basis of —$OCH_3$ and —$NCH_2CH_2$ proton resonance peak integration values is 4.0 kDa.

3. Characterization of the Naked Type Adenovirus (Naked Ad) and Ad/CBA Complex

The average size and zeta potential of the Ad-CBA complex were measured using Zetasizer 3000HS (Malvern Instruments, Inc., Worcestershire, UK) with a He—Ne laser beam (633 nm, fixed scattering angle of 90°) at 25° C. An electrostatic interaction was generated in the CBA-dose dependent manner. In summary, the Ad ($2\times10^{10}$ VP) was mixed with the polymer at various concentrations, gently stirred using a pipette tip and cultured at room temperature for 30 minutes. After formation of Ad-CBA complexes in each ratio, the PBS (pH 7.4) was added to have the final volume of 1.0 mL. Size and zeta potential values were shown as average value of three measurements.

4. Transmission Electron Microscope (TEM) Image Analysis

The forms of naked type Ad and Ad-CBA complex were cultured in PBS of various pH conditions (7.4 and 6.0) for 30 minutes, and then analyzed by TEM (JEM-2000EX11, JEPL, Nikon, Tokyo, Japan).

5. Ad-CBA Transduction Efficiency Assay

The transduction efficiency of each Ad-CBA complex at various concentrations was measured as a GFP expression level in CAR-positive (U343) and CAR-negative (MCF7) cells by FACS analysis. Each cell line was dispensed in 12-well plate at a density of $1\times10^5$ cells/well before Ad transduction. Cells were transduced for 30 minutes in PBS of pH 7.4 and pH 6.0 at 100 (U343), 500 (MCF7) MOI using the naked type Ad or Ad-CBA complex. After transduction for 48 hours at 37° C., the cells were observed by fluorescence microscopy (Olympus IX81; Olympus Optical, Tokyo, Japan). Also, the cells were observed using the CellQuest software (Becton-Dickinson) FACScan analyzer (Becton-Dickinson, San Jose, Calif.); ten thousand data were collected for further analysis, which represented relative fluorescence signal values. Data represent mean and standard error of 3 experiments.

6. Gel Retardation Assay

In order to evaluate the encapsulation ability of Ad-CBA complexes, the CBA coated with Ad (0.01~0.5 mg/ml) was prepared at various concentrations. The Ad-CBA complex of various concentrations was filled in 0.8% (w/v) agarose gel in 1×TAE buffer (10.0 mM Tris/HCl, 1% (v/v) acetic acid and 1.0 mM EDTA) containing ethidium bromide (EtBr) and electrophoresis was performed in the same buffer at 80V for 30 min Finally, the viral DNA was visualized using the ChemiDoc gel documentation system (Syngene, Cambridge, UK).

7. Competition Assay with Fiber Protein of Adenovirus

U343 cells were plated in 12-well plate at a concentration of $1\times10^5$ cells/well. After 24 hours, the cells were cultured in PBS or FBS-free DMEM containing a fiber protein (0.2 and 2 mg/mL) at 4° C. for one hour.

The naked type Ad or Ad-CBA complex was added to a medium at 20 MOI and incubated at 37° C. for 1 hour. Thereafter, the medium was washed with a cold PBS and replaced with DMEM containing 5% FBS. After incubation for 24 hours, the cells were observed by a fluorescence microscope. GFP expression was quantified by flow cytometry and analyzed using the CellQuest software.

8. Cellular Uptake Mechanism/Endosomal Escape of Ad-CBA Complex

U343 and MCF7 cell lines were pretreated using a) chlorpromazine (0.2 and 1 μM) (a clathrin-mediated endocytosis inhibitor), b) Genistein (1.25 and 5 μM) (a caveolin-mediated endocytosis inhibitor), c) $NH_4Cl$ (0.5 and 1 μM) (a macropinocytosis inhibitor), or d) Bafilomycin A1 (a endosomal escape inhibitor) for 30 minutes at pH 6.0 and 7.4. The naked type Ad or Ad-CBA complex was added in the presence or absence of the inhibitors for an additional 2 hours. Then, the cells were washed with PBS and replaced with DMEM containing 5% PBS. The cultured cells were observed by fluorescence microscope for 48 hours. GFP expression was quantified by flow cytometry and analyzed using the CellQuest software.

9. VEGF Quantification

The human VEGF-A was quantified according to the manual using a human VEGF Quantikine Immunoassay kit (R&D Systems, Minneapolis, Minn.). The standard curve was established using the continuous dilution of a usual amount of the purified recombinant human VEGF-A. In summary, the cells were dispensed in a medium containing 5% FBS in 6-well plates. When the cells reached the density of 50%, the cells were infected with RdB/shVEGF and RdB/shVEGF-CBA (pH 7.4, 6.0) at 1 and 10 MOI, and the secreted VEFG was measured by an ELISA kit.

10. MTT Assay

In order to measure the tumor cell lethal effect of RdB/shVEGF or RdB/shVEGF-CBA at pH 6.0 and 7.4, the U343 and MCF7 cells cultured to the 50% density were infected using the naked type RdB/shVEGF or RdB/shVEGF-CBA at an MOI ((U343 cell—20 MOI, MCF7-mot—200 MOD), and cultured at 37° C. Two days after the infection, 250 μL of 3-(4,5-dimethyl-2-yl)-2,5-diphenyl-tetrazolium bromide (MTT; Sigma-Aldrich, St. Louis, Mo., USA) was added to each well in PBS at a rate of 2 mg/mL and cultured for four hours at 37° C., and then the supernatant was discarded and the precipitate was dissolved in 1.0 mL DMSO. Then, the plate was decoded on a microplate reader of 540 nm. The number of viable cells in a non-infected cell group was analyzed similarly to the negative control group.

11. Ex Vivo Matrigel Plug Assay

MCF7 cells ($2\times10^5$) were dispensed in a 6-well plate and infected with RdB/shVEGF or RdB/shVEGF-CBA in PBS at pH 7.4 or pH 6.0. After 6 hours, the treated cells were obtained after trypsin treatment and washed three times with 5 ml of the HBSS buffer. Then, the cells were mixed with 600 μL cold matrigel and injected into a subcutaneous space on a flank area of a male athymic nu/nu mouse with 1 mL syringe. The injected matrigel rapidly formed a single, solid gel plug. After 14 days, the animal was sacrificed and each mouse skin was pulled up to be exposed to the matrigel plug. And this matrigel plug was placed in an intact state. In order to quantify angiogenesis, the matrigel plug was fixed using a zinc fixing solution embedded in paraffin. These slices were treated with the purified mono monoclonal rat anti-mouse CD31 (platelet/endothelial cell adhesion molecule 1; BD biosciences Pharmingen, San Diego, Calif., USA) and then treated with goat anti-rat-IgG-HRP. All slides were counterstained with hematoxylin of Meyer.

12. Measurement and Toxicity Studies of Inflammatory Cytokines

Inflammatory immune reaction and toxicity were examined after systemic injection of PBS, Ad ($2\times10^{19}$ VP) and Ad-CBA ($2\times10^{19}$ VP). The blood sera were obtained from the retroorbital blood 6 hours after the injection, and the IL-6 (DY406; R&D System) levels were quantified. Three days after injection, the mice were sacrificed to obtain the sera. Aspartate aminotransferase (AST) and alanine aminotransferase (ALT) levels were measured. Measurement of toxicity was carried out by Neodin Corporation (Seoul, Korea).

13. Evaluation of Anticancer Effect

In order to evaluate the anticancer effect of Ad (RdB/shVEGF)-CBA, U87 tumor xenografts were established into subcutaneous fat by abdominally injecting $1\times10^7$ of the cells into 6-8 week old female athymic nude mice (Charles River Korea Inc). Once the tumor size reached 100-120 mm$^3$, three groups of mice (PBS, RdB/shVEGF, and RdB/shVEGF-CBA) were randomized and 30 μL PBS or $5\times10^9$ VP of RdB/shVEGF or RdB/shVEGF-CBA was injected into the tumor once every other day. To assess the anticancer effect of systemic administration, PBS, RdB/shVEGF ($2\times10^{10}$ VP/200 μL) and RdB/shVEGF-CBA ($2\times10^{10}$ VP/200 μL) were injected into the tail vein in the mice having U87 tumor, respectively. The length (L) and width (W) of the tumor were measured using a caliper three times a week to calculate the tumor growth. The tumor volume was calculated according to the following formula:

$$\text{Tumor volume} = 0.523 L W^2 \quad \text{Formula:}$$

14. Stability and DTT Treatment Effect Test

The average size of the polymer-coated Ad complex was tested by DLS analyzer. After coating the Ad (dE1/GFP) with CBA in PBS for 30 minutes at room temperature, the particle size distribution was measured in the predetermined time intervals from 1 hour to 24 hours. The measured sizes were shown as the average value of three times.

Also, before and after treating with DTT (5 mM) for 2 hours at 37° C., the average size distribution of the Ad-CBA complex was measured by DLS analyzer.

15. Statistical Analysis

The data were expressed as mean±mean standard error. Mann-Whitney test (SPSS 18.0 software; SPSS, Chicago, Ill.) was performed for statistical comparison (SPSS 18.0 software; SPSS, Chicago, Ill.). A statistically significant deviation value is 0.05 or less.

Experimental Result

Figure 1B:
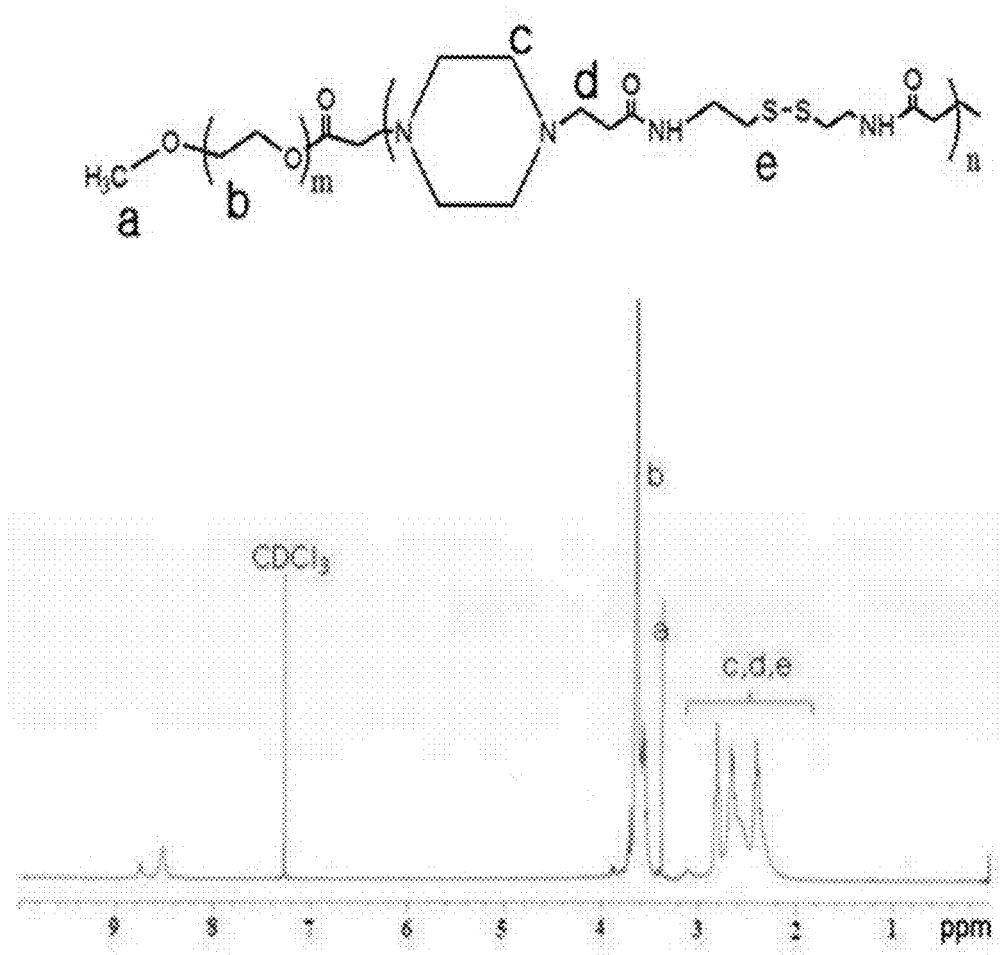

1. Synthesis and Characteristic Analysis of Bioreducible Polymers and Ad-CBA Complexes The synthesis of pH-sensitive and bioreducible polymers (CBA) was explained in FIG. 1A. This polymer (CBA) was synthesized through a Michael type addition polymerization. Then, the reaction of N,N'-cystaminebisacrylamide having mPEG-acrylate and piperazine led to the formation of mPEG-b-Pip-CBA (CBA). The chemical structure of the CBA was identified in 2.3-2.8 ppm, its typical resonance peaks, by $^1$H NMR (300 MHz, CDCl$_3$), which correspond to —N(CH$_2$—CH$_2$), methylene cation of piperazine, and —S—CH$_2$—CH$_2$—NH—CO— proton of CBA according to characteristic peaks of mPEG, according to characteristic peaks of mPEG, respectively (FIG. 1B). The absence of any proton signals between 5 and 6.5 ppm indicates that no residual of acrylamide or acrylate monomers are present in finally synthesized CBA polymer. Further, the average molecular weight was determined by gel permeation chromatography (GPC). The observed average molecular weight was Mw=2.85 kDa with a PDI of 1.87. Furthermore, the matrix-assisted laser desorption/ionization-time of flight mass (MALDI-TOF) spectrum showed that the molecular weight of CBA copolymer in comparison to mPEG (2 kDA) confirms the formation of CBA copolymer. The ratios of —OCH$_3$ of PEG and —S—S—CH$_2$—CH$_2$—NH—CO— of alkyl chain were caculated by integrals of the two peaks, and valure was identified as 1:6 (FIG. 1B). These results suggest that the polymer is close to the expected composition, in a good agreement with MALDI-TOF data.

Figure 1C:
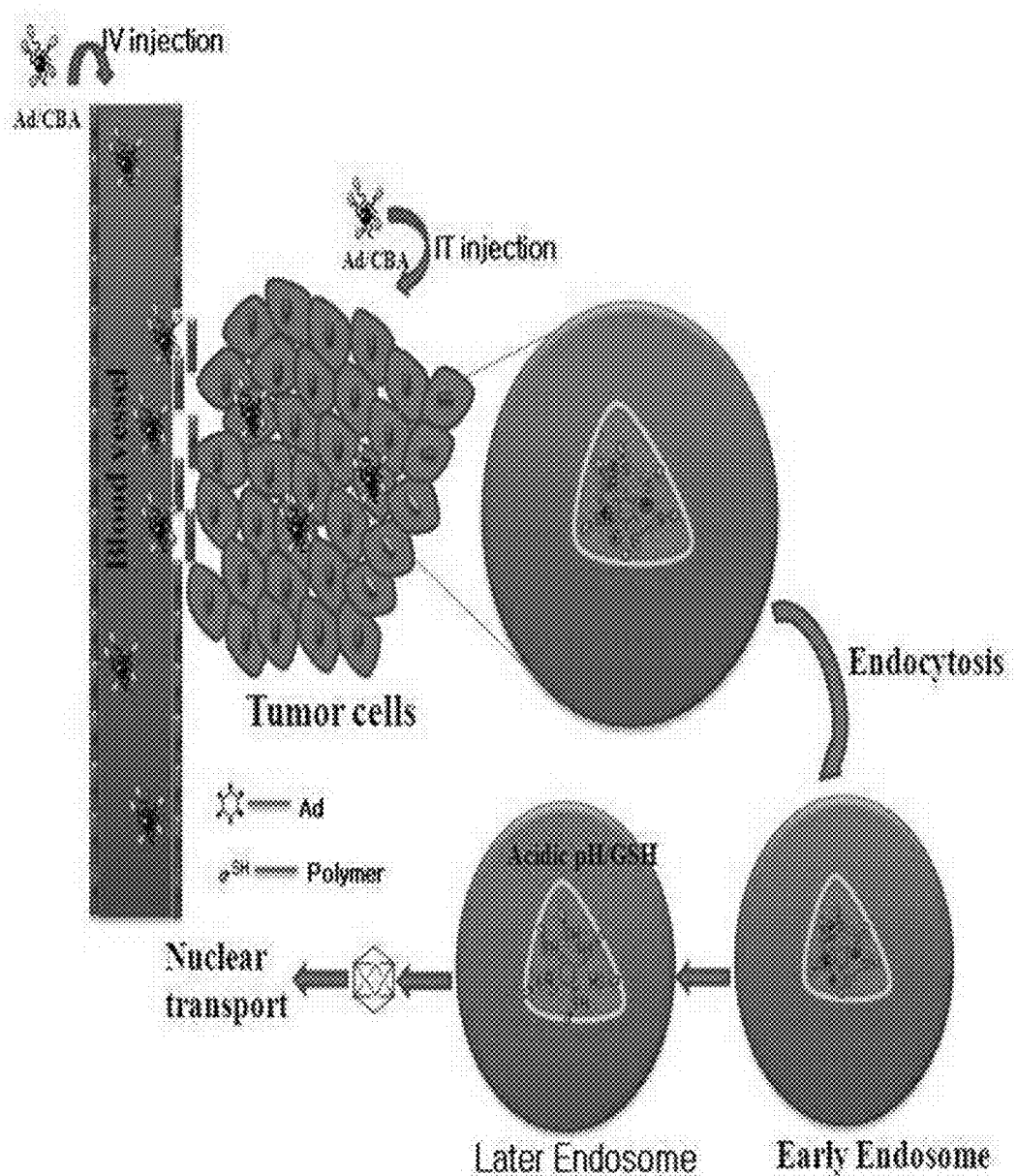
Figure 1D:
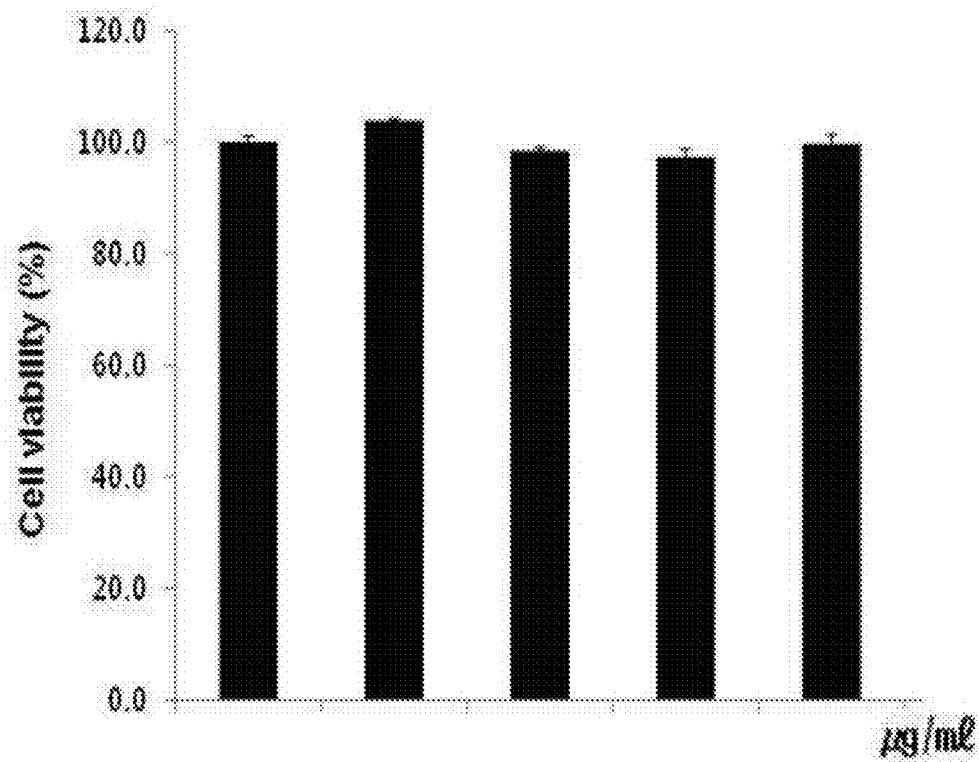
Figure 1E:
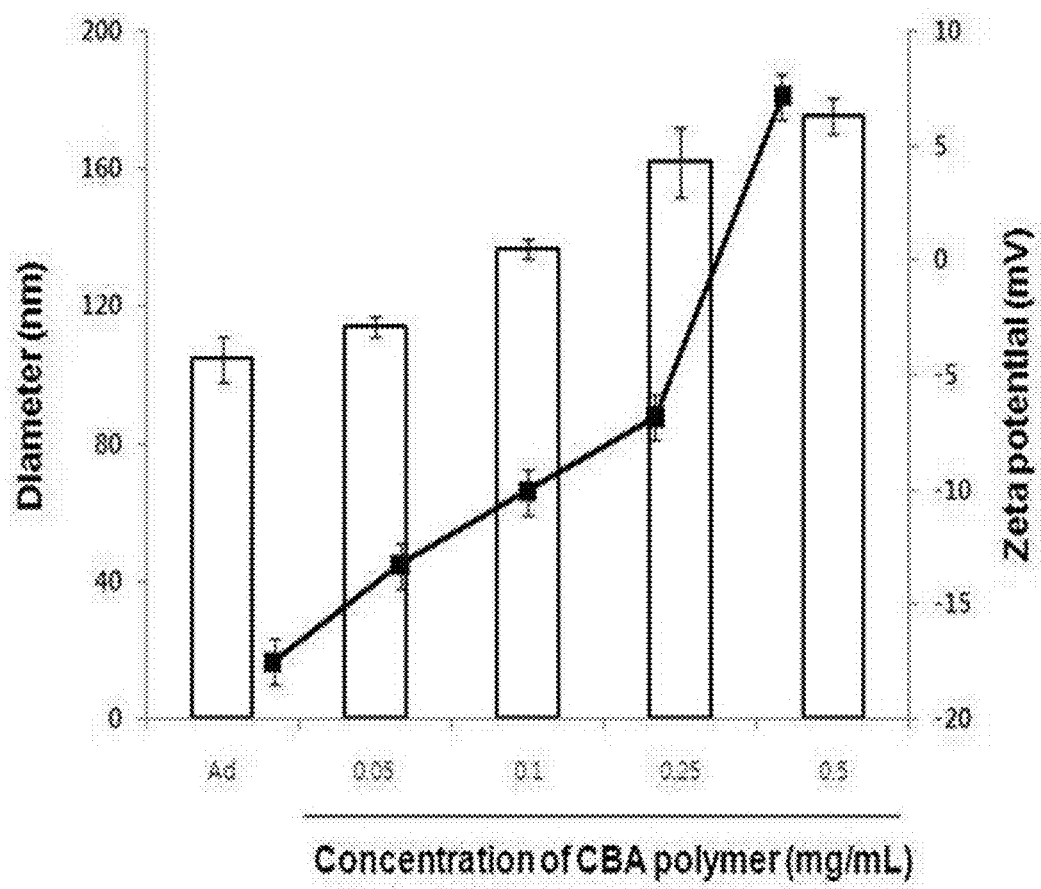

As shown in the structural diagram (FIG. 1C), the positively chargeable CBA polymer allows for complexation and cellular degradative mechanism of the negatively chargeable Ad through ionic interactions. In addition, the disulfide bond present in the polymer allows for cellular degradation of the polymer by reducing an enzyme, such as glutathione and thioredoxin reductase. The cytotoxicity profile of the CBA polymer was evaluated by MTT assay. FIG. 1D shows that the CBA does not exhibit a significant toxicity even in high concentration. Cell viability was 95% or more at less than 100 μg/mL. After generating the Ad-CBA complex through the electrostatic attraction, as the concentration of the CBA increased, the average size and surface charge of the complex were measured by dynamic light scattering method (DLS) and zeta potential analyzer (FIG. 1E). The diameter of the naked type Ad increased from 104±6.64 nm to 175±5.2 nm, where the CBA had the maximum concentration (0.5 mg/mL). In addition, the surface charge of the complex increased from −17.5 mV±0.40 mV of a minus value to 7.31±0.78 mV of a plus value, and then the coating of the CBA was 0.5 mg/mL. These experimental results indicate that the coating of the cationic CBA polymer having virus particles increases the diameter and the zeta potential value of the Ad-CBA in a concentration dependent manner Overall, the experimental results demonstrate that the CBA appropriately forms a complex with Ad through the electrostatic interaction.

2. Transmission Electron Microscope (TEM) Image of Ad-CBA Complex

Figure 2A:
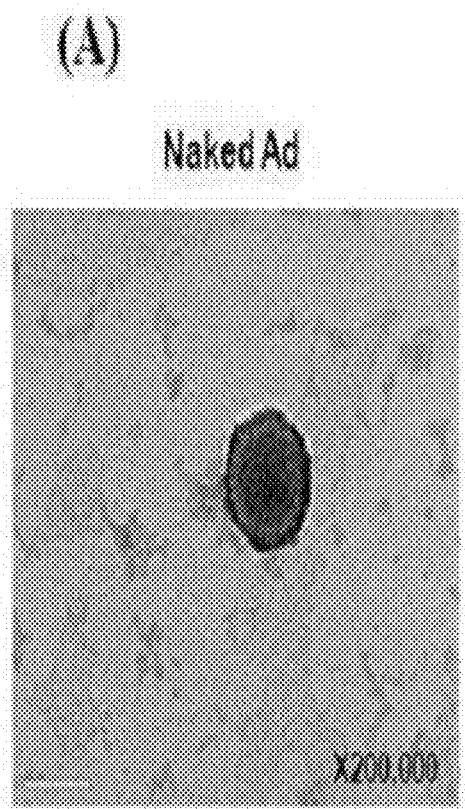
FIGS. 2A, 2B, and 2C are TEM images of the naked type Ad (FIG. 2A) and the Ad-CBA complex (FIGS. 2A, 2B). The Ad and Ad-CBA were cultured at pH 7.4 (FIG. 2B) and pH 6.0 (FIG. 2C) with PBS for 30 minutes.
Figure 2B:
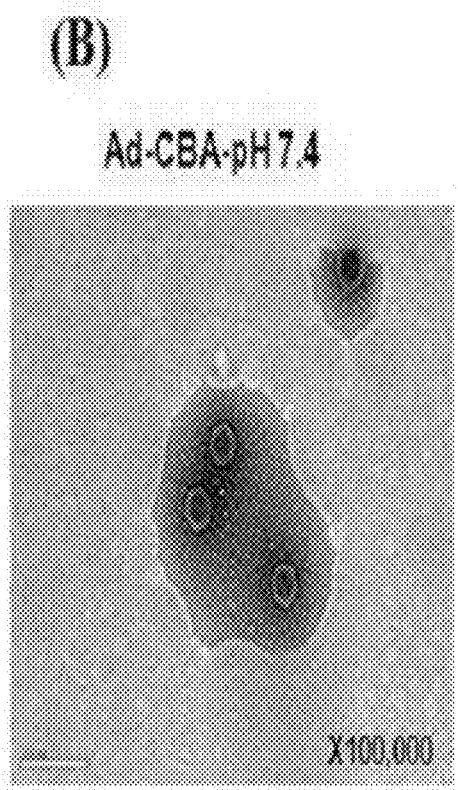
Figure 2C:
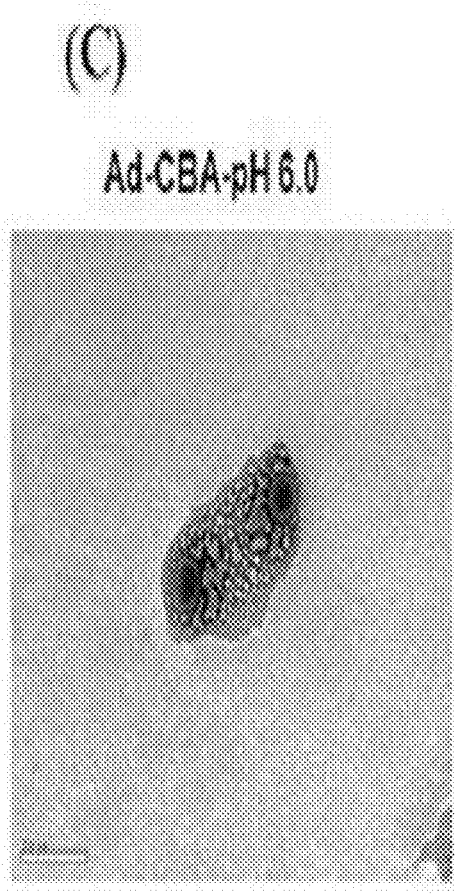

The form of the naked type Ad and Ad-CBA complex was examined by TEM. FIG. 2 shows optical micrographs of the naked type Ad and Ad-CBA complex at 0.5 mg/ml of the CBA concentration, pH 7.4 and pH 6.0. The naked Ad does not only represent icosahedral shape (FIG. 2A) but also the characteristic hexon structure. On the other hand, the present inventors observed at pH 7.4 (FIG. 2B) a tendency that the chunk of Ad particles was surrounded by the "tensile chunk" of the CBA polymer, wherein this tensile chunk leads to collection of the Ad-CBA complex. This observation suggests that the cationic CBA polymer captures other particles and connect them to the negatively charged viruses. In contrast, the present inventors observed at pH 6.0 the shape of the swallowed CBA polymer demonstrated by ionization of the pH-sensitive residue in the polymer, which eventually leads to separation of each Ad particle. It was confirmed from these experimental results that the structure of the compressed Ad-CBA complex appearing at pH 7.4 is compared to the complex at the lower pH due to ionization and deionization characteristics.

3. Evaluation of Transduction of Ad-CBA CBA Based on CBA Concentrations

Figure 3A:
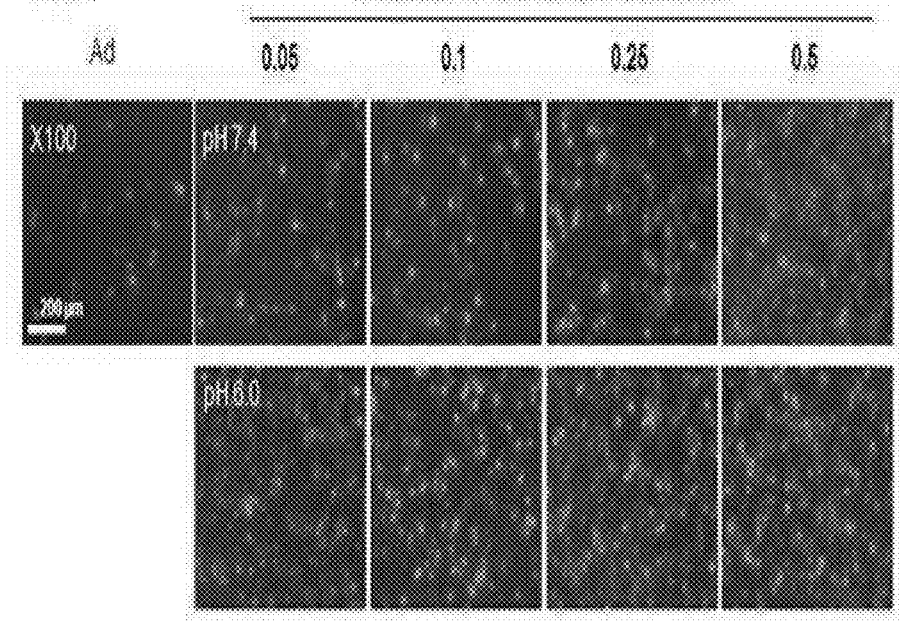
FIGS. 3A and 3B are views showing that the optimum conditions for forming the Ad-CBA complex is determined by the pH-dependent gene transfer efficiency and the gel retardation effect of the Ad-CBA complex.
Figure 3A:
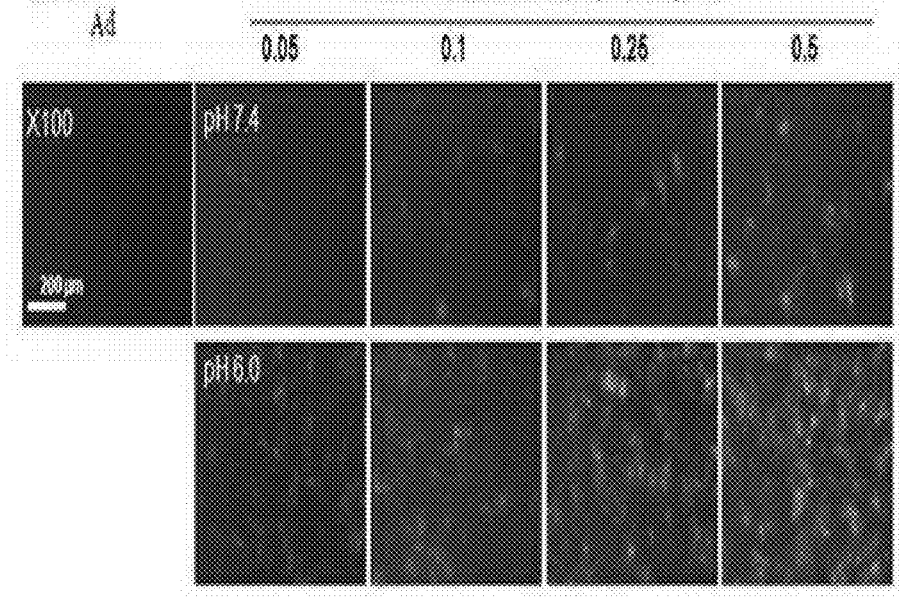
Figure 3B:
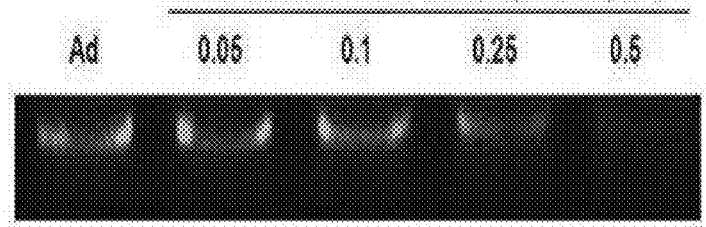

To assess the transformation efficiency of Ad-CBA complex in CAR (+) and CAR (−) cell lines, the present inventors transduced, first at pH 7.4 and pH 6.0, U343 (CAR (+)) and MCF-7 (CAR (−)) anticancer cells to the naked type Ad or Ad-CBA complex using each of MOI 20 and 200, where the CBA concentration is 0.05 mg/mL to 0.5 mg/mL. For U343 cells (FIG. 3A), the naked type Ad exhibits a low expression degree of transgene, but the Ad-CBA nanocomplex shows a low transgene expression at neutral pH and exhibits a high transgene expression at pH 6.4. Furthermore, transgene expression levels all are increased by increasing the polymer concentration for pH conditions. For MCF-7 cells (FIG. 3B), the experimental data show the most obvious difference at 0.5 mg/mL, and at the same time show the outstanding increase in the transgene expression level at pH 6.0 compared to the expression of the naked type Ad and Ad-CBA at neutral pH. In acidic pH conditions, the complex/polymer exhibits more positive surface charges that increase the binding affinity with the negatively chargeable cell membrane, and causes the increased gene transfer at a lower pH compared to neutral pH.

To find the optimum concentration for the Ad complex formation, the present inventors carried out a gel retardation assay (FIG. 3C). It was demonstrated from experimental results that the Ad-CBA retardation started at 0.25 mg/mL and was completed at 0.5 mg/mL. Based on these experimental results, the concentration of 0.5 mg/mL was used for the experimental results below unless otherwise stated. These experimental results did not only designate the CBA concentration of 0.5 mg/mL as the optimized concentration for Ad modification/conjugation, but also demonstrated that the CBA polymer appropriately forms a complex with Ad. Overall, the experimental results demonstrated much more improved transformation efficiency of the Ad-CBA complex than the naked type Ad counterparts in acidic conditions, regardless of the presence of the CAR receptor.

4. Uptake Mechanism of Ad-CBA Complex

Figure 4A:
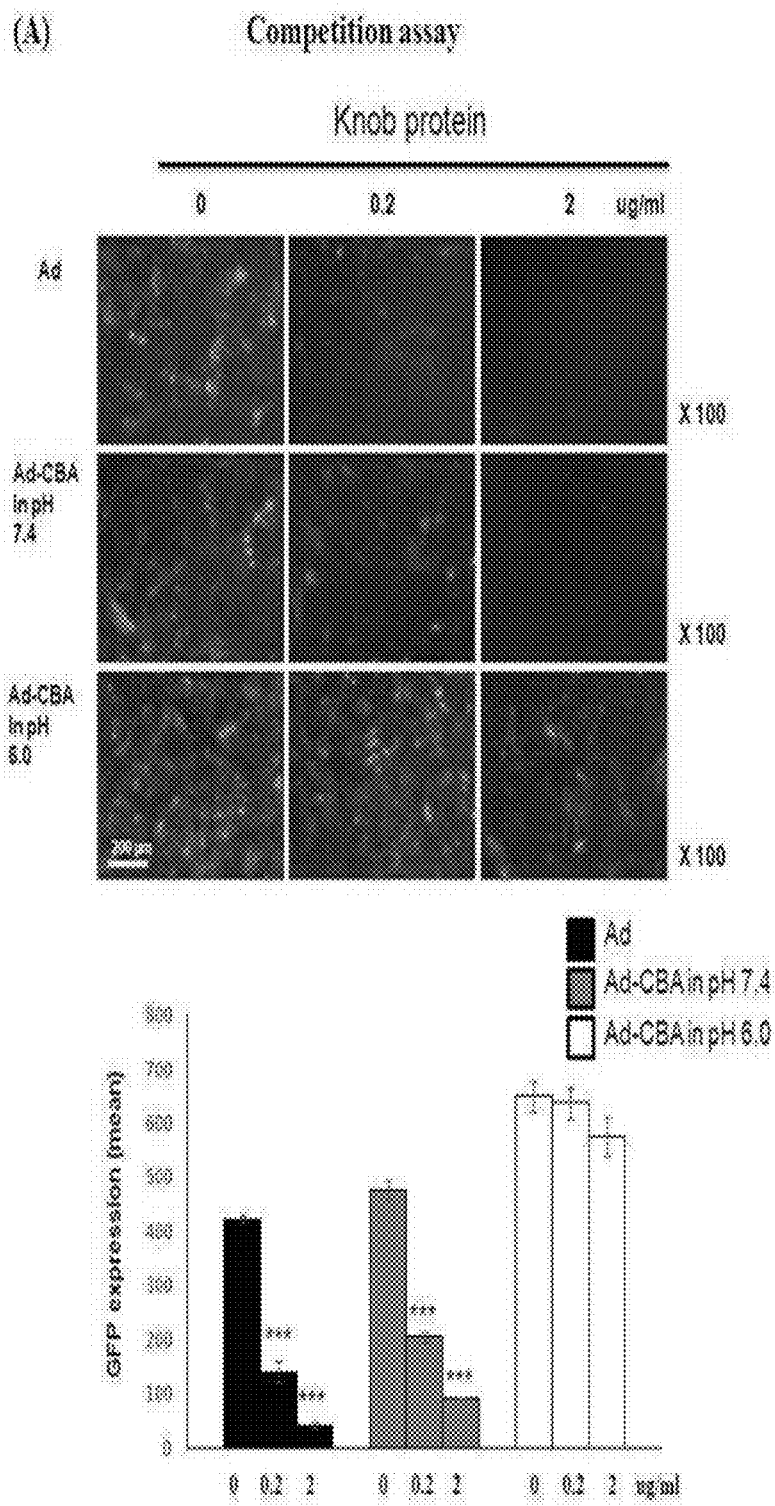
FIGS. 4A, 4B, and 4C are views showing a competition assay using a fiber protein.

The present inventors tried to determine the cellular uptake mechanism of Ad-CBA complex. First, the CAR competition assay was performed to study the CAR deficiency degree of nanocomplexes in the uptake mechanism. Pretreatment into the CAR-specific fiber protein significantly reduced the GFP transduction to the naked type Ad in a dose-dependent manner (when 0.2 and 2 µg/ml of fiber proteins were pretreated, 67% and 90% reduced, respectively). In contrast, the GFP transduction mediated by Ad-CBA (pH 6.0) was not blocked by the fiber protein, and this shows that the Ad-CBA uptake was not mediated by the interaction between the CAR and the fiber. Therefore, these results clearly demonstrated that the uptake of the Ad-CBA has the ability to overcome the CAR-dependent uptake (FIG. 4A).

Figure 4B:
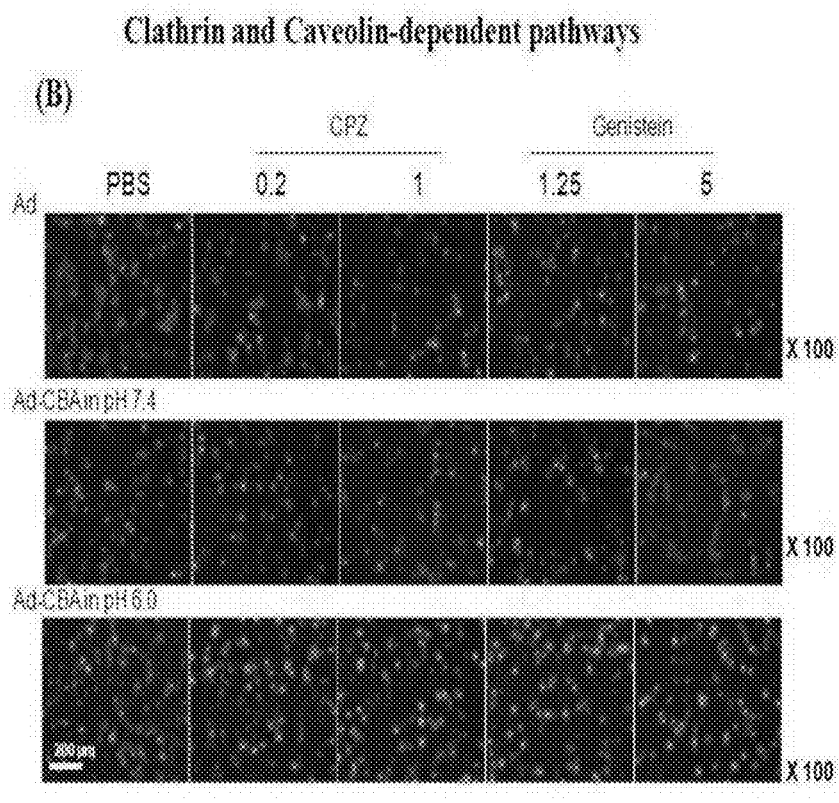
Figure 4B:
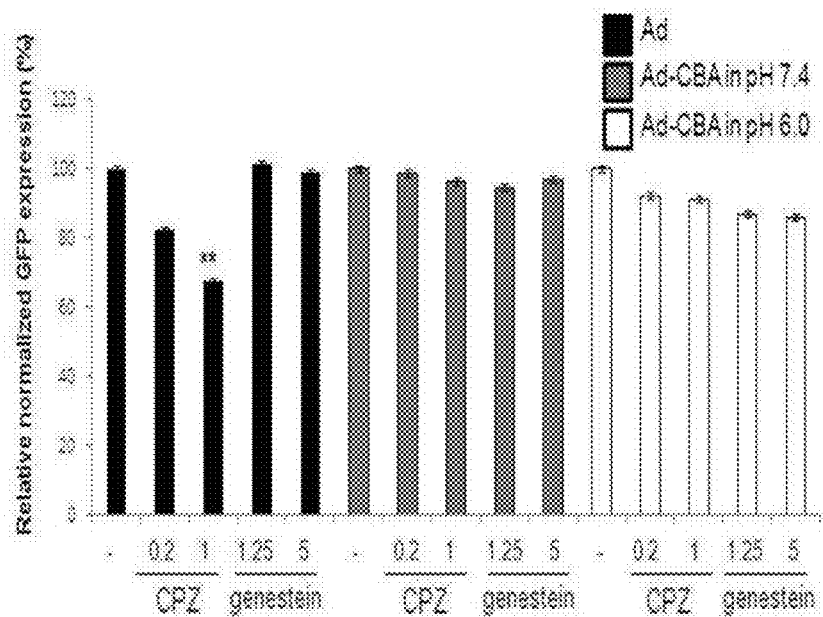
Figure 4C:
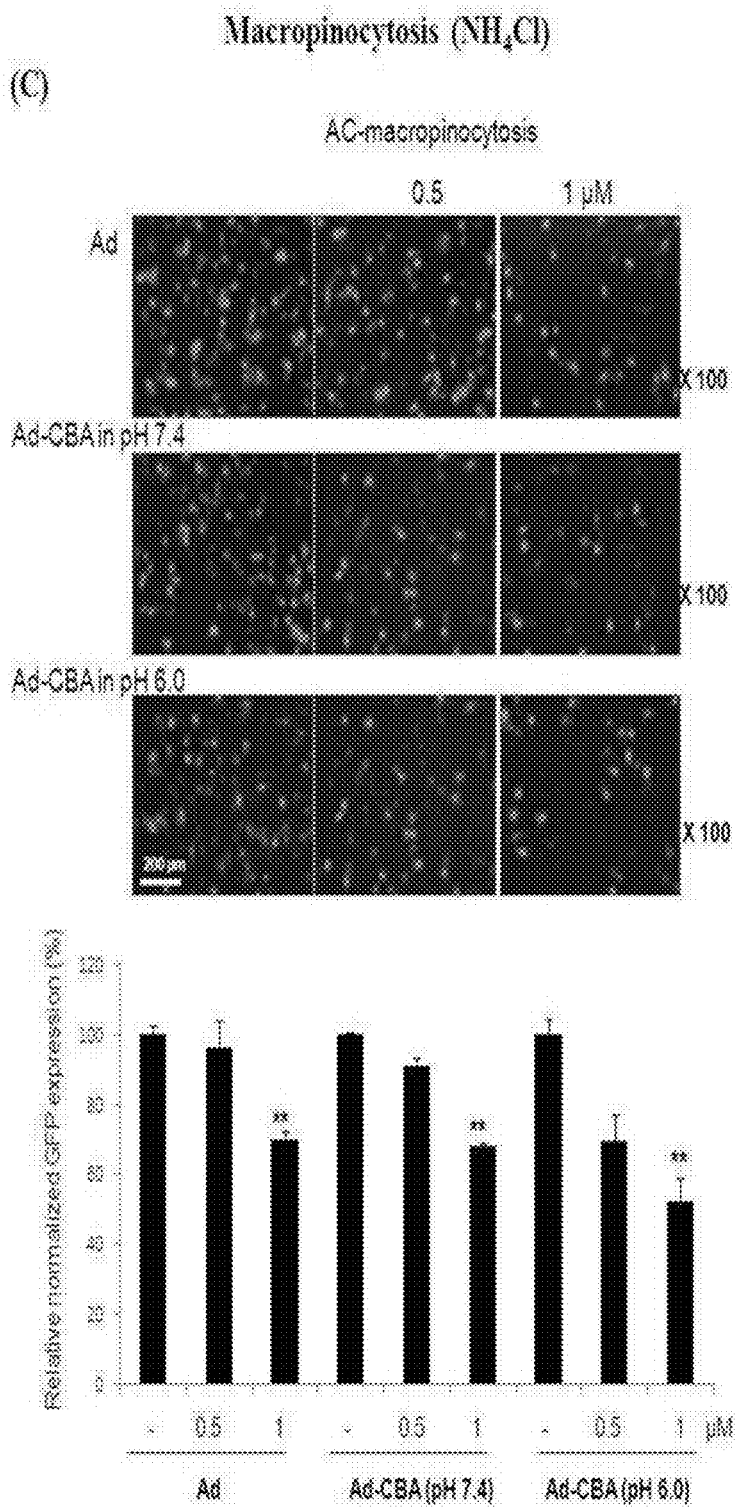

Second, the present inventors co-cultured the u343 cells with other uptake inhibitors: 1) chlorpromazine (CPZ): clathrin-mediated endocytosis inhibitor (0.2 and 1 µM), 2) genistein: caveolae-mediated endocytosis (1.25 and 5 µM), 3) NH$_4$Cl: macropinocytosis (0.5 µM). As shown in FIG. 4B, the Ad-CBA complex was not affected by the CPZ in both two pHs, since the GFP expression level remained the same. In contrast, the naked type Ad group showed a decrease in GFP expression, which confirmed the dependency of Ad on the clathrin-mediated endocytosis. Genistein treatment did not have any inhibitory effect on the uptake of the naked type Ad and Ad-CBA complex at the same pH. This shows that all three groups do not use the caveolin-mediated endocytosis. However, treatment of NH$_4$Cl indicated that macropinocytosis is the major endocytosis path for Ad-CBA (pH 6.0). At 0.5 µM, a decrease in GFP expression level of the Ad-CBA (pH 6.0) is statistically significant, but a decrease in the naked type Ad and Ad-CBA (pH 7.4) is not statistically significant (FIG. 4C). Overall, these experimental results indicate that the Ad-CBA (pH 6.0) overcomes the CAR dependence by using different uptake paths (macropinocytosis).

5. Evaluation of Endosomal Escape of Ad-CBA Complex

Figure 5A:
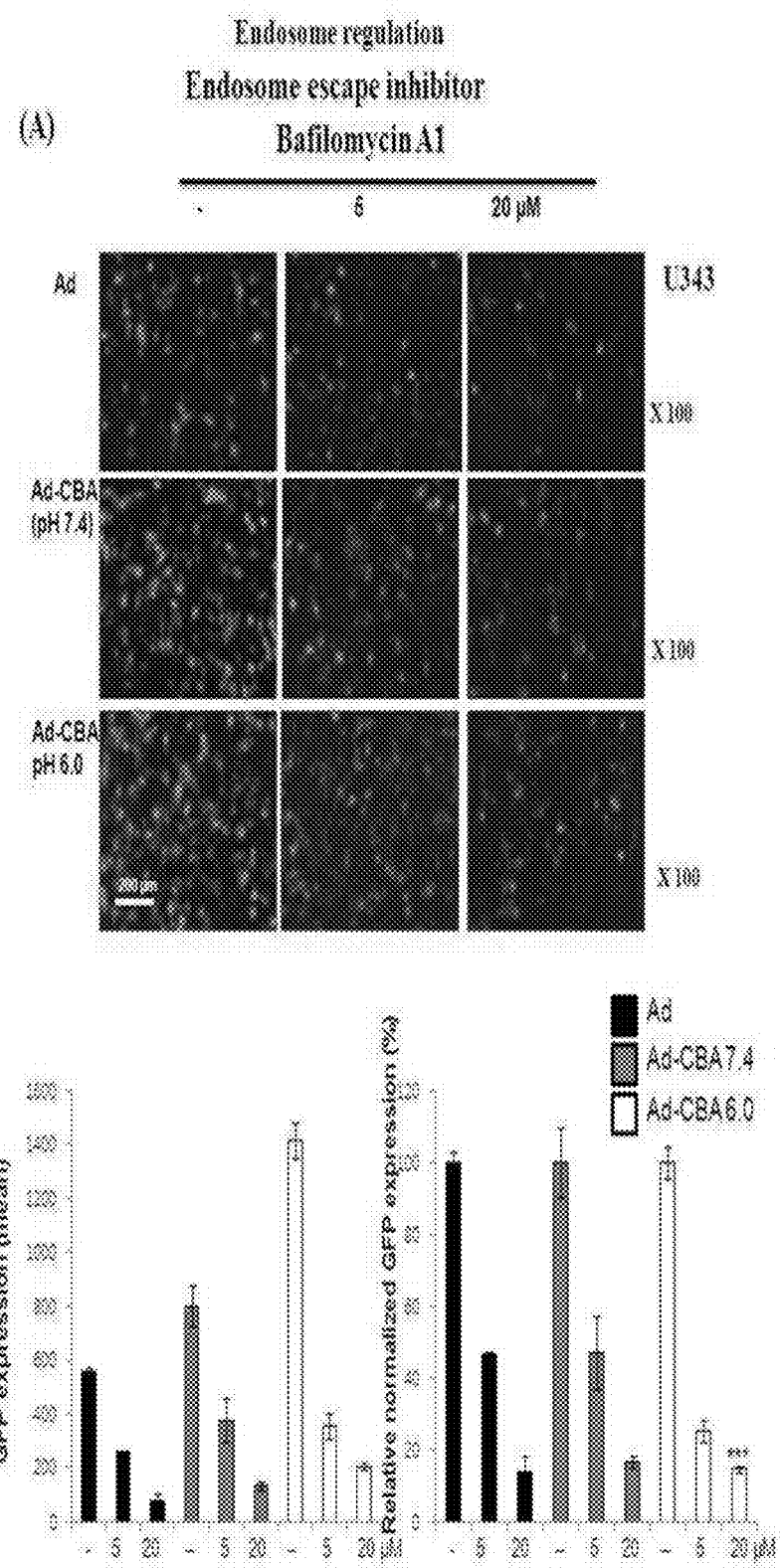
FIGS. 5A-5B are views showing evaluation of Ad-CBA endosome escape capability. The MCF (FIG. 5A) and U343 (FIG. 5B) L cells were precultured with BF-a1 at 4° C. for 1 hour. The naked type Ad and Ad-CBA were added at MOI 20 or 200, respectively. The cells were analyzed for GFP expression by a flow cytometer, 48 hours after transduction. Data were performed in three independent repeated experiments, and the bar represents the mean±standard error, and *P<0.05 and **P<0.01 vs. untreated group.
Figure 5B:
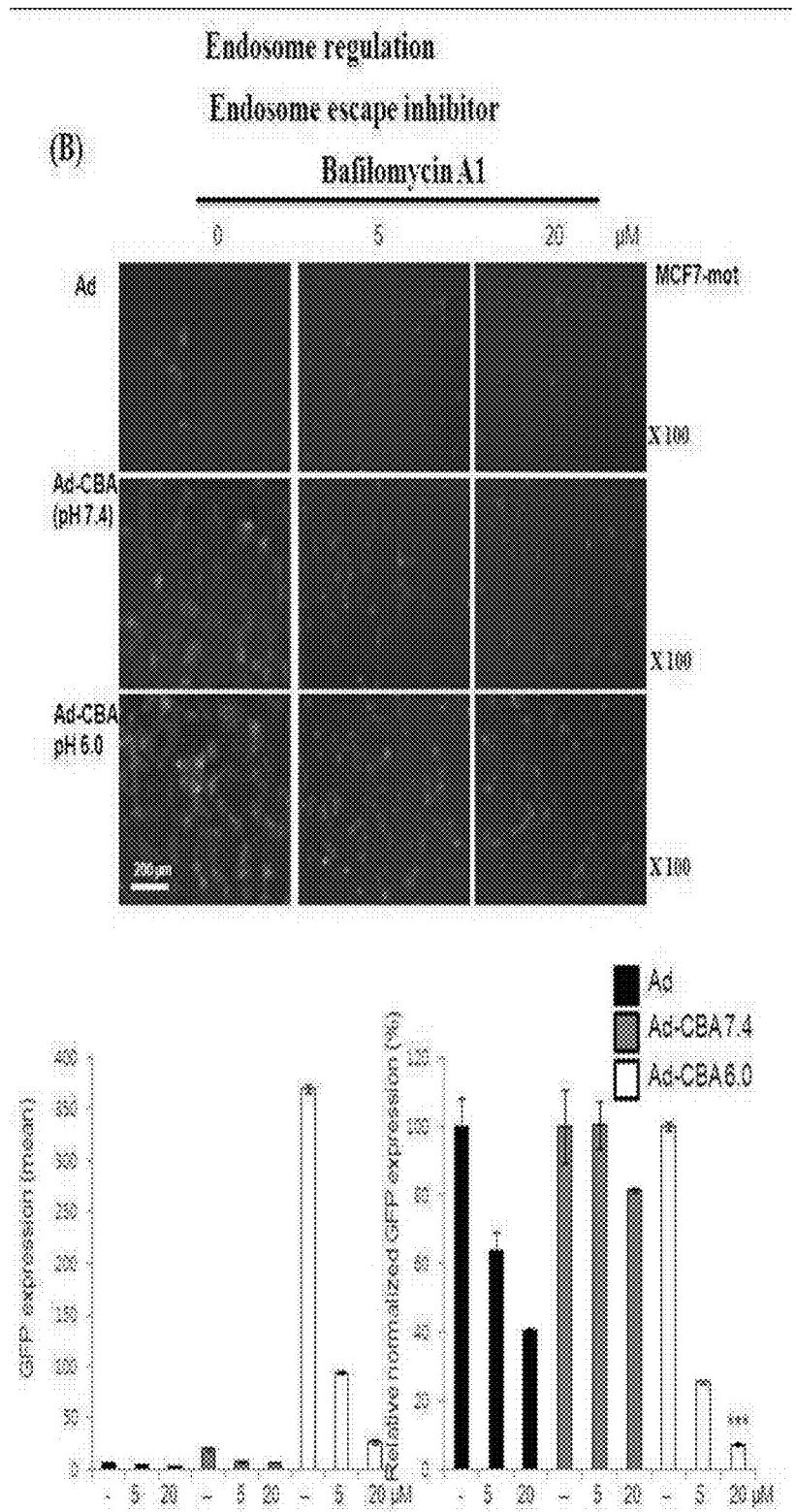

Bafilomycin (Bf-A) is a vacuolar H$^+$ ATPase to prevent acidification of Ad, which is an important element for viral escape from the endosome. In order to assess endosomal escape ability of Ad-CBA complex, U343 and the MCF-7 cell lines were co-cultured with 5 and 20 µM of Bf-A. As demonstrated in the transduction efficiency study, the Ad-CBA at pH 6.0 showed higher transduction efficiency than the naked type Ad and Ad-CBA group in CAR (+) and CAR (−) cell lines (pH 7.4). However, the relatively normalized GFP expression levels of two cell lines shows a rapid decrease in the transduction level of Ad-CBA (pH 6.0) on treatment of Bf-A (FIG. 5). Interestingly, in the U343 cell line, the present inventors could observe that the GFP expression level of Ad-CBA (pH 6.0) decreased to the level similar to the expression level of Ad-CBA (pH 7.4) on the initial treatment of Bf-A (5 µM), which suggests that the acidification of endosome is extremely important to the efficient transduction of Ad-CBA (p<0.001). MCF7 data demonstrate a similar point (FIG. 5B). Other CAR-dependent group (the naked type Ad and Ad-CBA (pH 7.4)) still showed a significant decrease after treatment of Bf-A (p<0.001). The experimental results indicate that the transduction path of Ad-CBA is under endosome control.

6. Therapeutic Effect of In Vitro Ad (RdB/shVEGF)-CBA

Figure 6A:
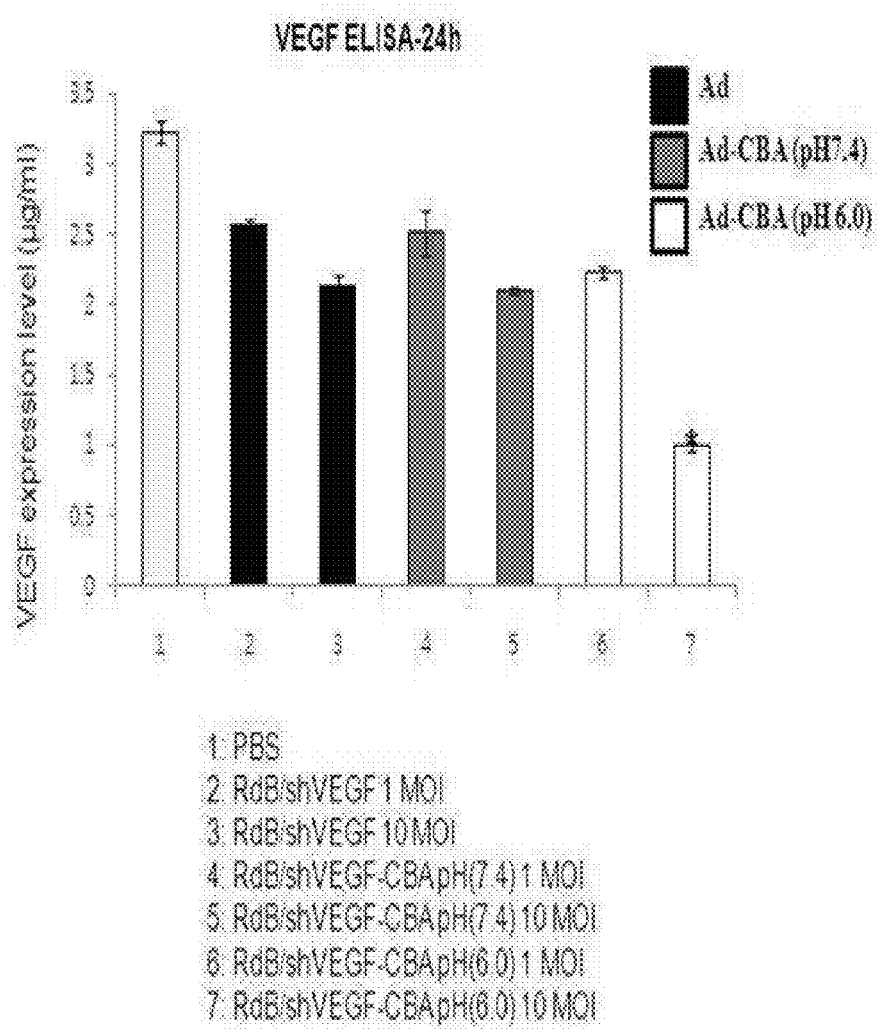
FIGS. 6A-6B are diagrams showing quantification of VEGF and anti-cancer lethal effect of RdB/shVEGF-CBA.

After determining transduction and uptake mechanism of Ad-CBA, the present inventors tried to assess the gene transfer and the degree of functional ability in oncology of Ad-CBA. The VEGF-specific shRNA expressing a plasmid was established and the Ad (RdB/shVEGF)-CBA expressing VEGF-specific short hairpin RNAs was synthesized as described above. The present inventors first monitored the degree of gene silencing by RdB/shVEGF-CBA as an indicator for the gene transfer ability of RdB/shVEGF-CBA. The inventors infected U343 cells with the naked type RdB/shVEGF, RdB/shVEGF-CBA (pH 7.4) or RdB/shVEGF-CBA (pH 6.0) at MOI 1 and 10 for 24 hours, respectively, and measured the expression of VEGF in each group using the VEGF ELISA assay. The naked type RdB/shVEGF and RdB/shVEGF-CBA (pH 7.4) groups did not show a significant decrease in VEGF levels at both two MOIs, and the RdB/shVEGF-CBA (pH 6.0) at 10 MOI effectively inhibited the VEGF expression (p<0.05). It was confirmed that the much improved transduction efficiency of RdB/shVEGF-CBA in acidic conditions the increased transfer and functionality of the therapeutic siRNA (FIG. 6A).

Figure 6B:
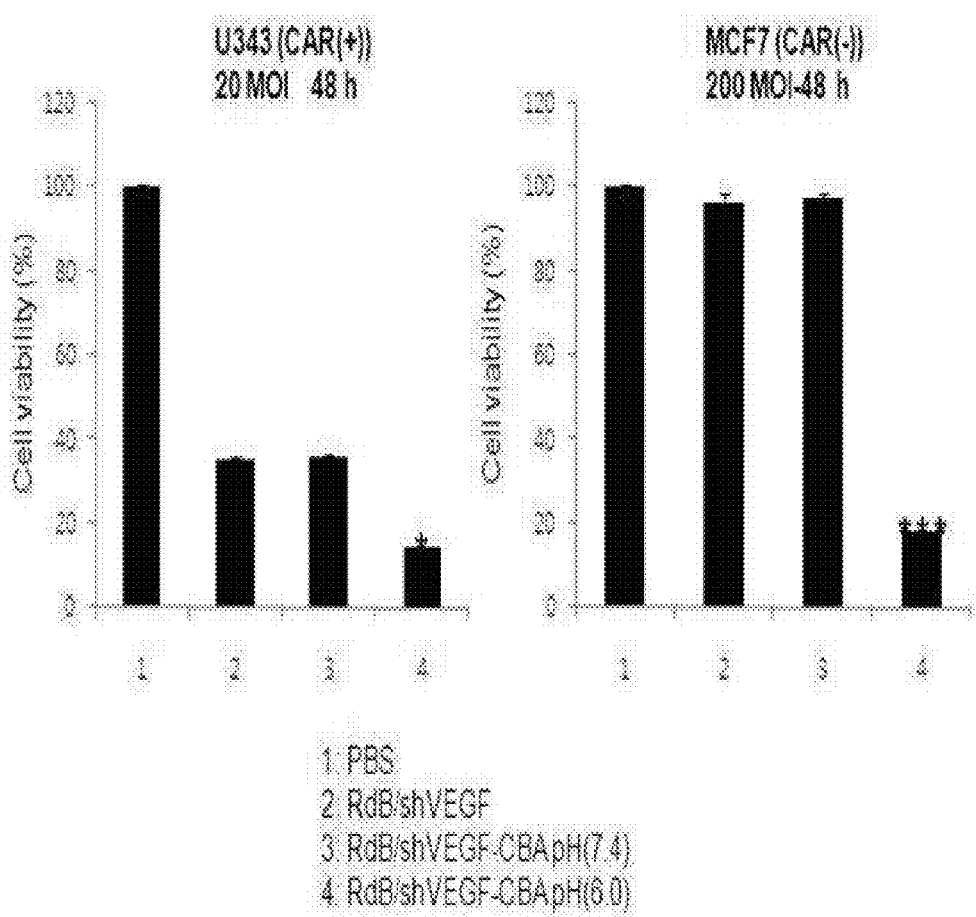

Furthermore, the present inventors tried to verify the tumor lethal effect of Ad (RdB/shVEGF)-CBA in both CAR (+) and CAR (−). The present inventors infected U343 and MCf7 cells with the naked type RdB/shVEGF, RdB/shVEGF-CBA (pH 7.4) or RdB/shVEGF-CBA (pH 6.0) for 48 hours and analyzed each group through the MTT assay. The naked type Ad and Ad-CBA exhibited varying degrees of anticancer activity in the U343 cell line at both pHs because of the facilitated uptake of Ad by the CAR receptor (FIG. 6B). However, RdB/shVEGF-CBA (pH 6.0) still showed the most significant tumor lethal effect compared with the naked type RdB/shVEGF or RdB/shVEGF-CBA (pH 7.4) group (p<0.01). The difference between RdB/shVEGF-CBA (pH 6.0) and the others appeared much more sharply than its CAR+ counterpart in the MCF7 cell line. The naked type RdB/shVEGF and RdB/shVEGF-CBA (pH 7.4) had almost no anticancer activity, but RdB/shVEGF-CBA (6.0) exhibited a rapid decrease in the cell group (p<0.001). The experimental results proved that the excellent transduction efficiency of RdB/shVEGF-CBA increases the strong anti-angiogenic and anticancer effects of the existing RdB/shVEGF by supplementing the normal limits of RdB/shVEGF, whereby the therapeutic effect and its synergic potential of RdB/shVEGF-CBA can be widely publicized.

7. In Vivo Therapeutic Effect of RdB/shVEGF-CBA

Figure 7A:
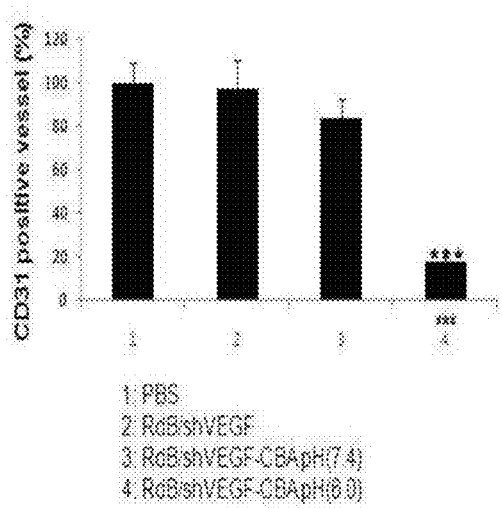
FIGS. 7A-7B are views showing a strong anti-angiogenic effect and anti-tumor effect of dB/shVEGF-CBA.

The present inventors intended to confirm that on the basis of the in vitro experimental results of therapeutic effects of RdB/shVEGF-CBA, the in vitro therapeutic effect of RdB/shVEGF-CBA is also interpreted as in vivo. First, the present inventors evaluated the anti-angiogenic effect of RdB/shVEGF-CBA through the matrigel plug assay. The MCF7 cells were infected with the naked type RdB/shVEGF or RdB/shVEGF-CBA treated with PBS at pH 7.4 or pH 6.0, mixed with cold matrigel and injected into the subcutaneous space in the flank area. The matrigel plug was dissected after 14 days and analyzed for the blood vessel quantification of each group. The naked type RdB/shVEGF and RdB/shVEGF-CBA (pH 7.4) showed the least reduction in blood levels, but RdB/shVEGF-CBA (pH 6.0) group exhibited the sharply reduced angiogenesis (FIG. 7A).

Figure 7B:
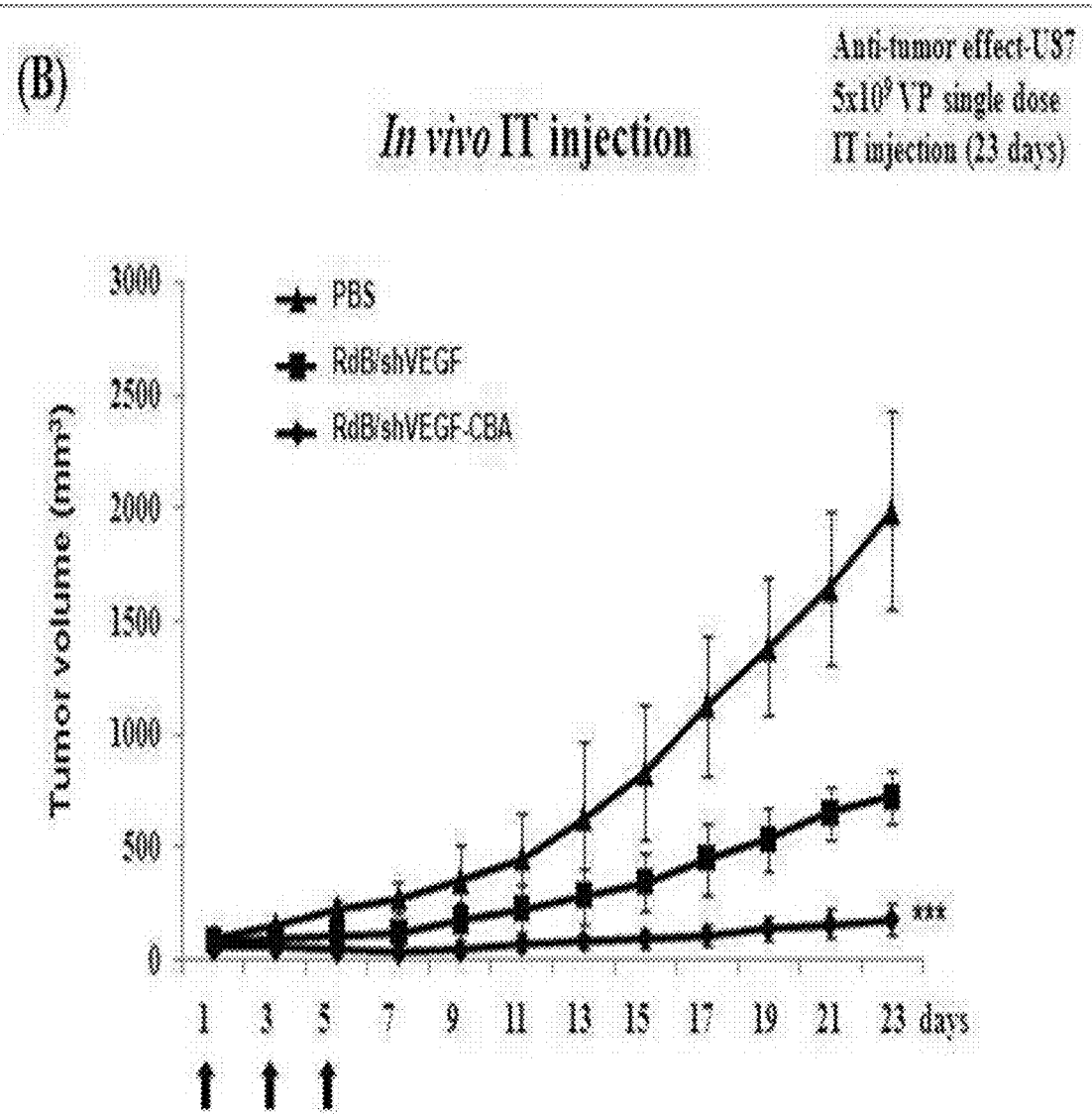

Next, the present inventors evaluated the anticancer effect of RdB/shVEGF-CBA in topical administration. Mice with U87 xenograft tumor were established and intratumorally treated with PBS, the naked type Ad or Ad-CBA over 23 days. As shown in FIG. 7B, the tumor growth was significantly inhibited in the RdB/shVEGF-CBA group compared to the Ad group (p<0.05). The average tumor sizes for PBS, AD and AD-CBA groups were 1984±439, 720±119, 177±73 mm$^3$, respectively, on Day 23 after xenograft subcutaneous injection. The corresponding tumor growth inhibition for Ad and Ad-CBA groups was Ad and Ad-CBA groups, respectively. Overall, the experimental results demonstrated the excellent efficiency of Ad-CBA in anti-angiogenesis and antitumor activity, whereby the in vivo therapeutic effect was confirmed.

8. Escape of In Vivo Immune Reaction (IL-6 Data, Liver Data of ALS/ALT)

One of the challenges inherent in the virus gene vectors in vivo administered, is the activation of the innate immune reaction to recognition of the system of Ad particles in blood. On the basis of the gel retardation assay and TEM images of the Ad-CBA, the present inventors hypothesized that the CBA encapsulation of Ad particles can allow for Ad-CBA complex avoiding the immune reaction of the system, that is, "stealth" Ad. The inventors observed a change of proinflammatory cytokine IL-6 (derived by Ad particles) in the serum level as measuring means of the innate immune system activation in order to assess the penetration characteristics of the Ad-CBA complex. BALB/C mice were intravenously injected with PBS, $1\times10^{10}$ VP of naked type Ad, CBA or Ad-CBA, and after 7 days mouse sera were obtained and then analyzed by IL-6 ELISA. As expected, the injection of naked type Ad rapidly increased the serum IL-6 level compared to the PBS counterpart. However, the intravenous treatment of CBA exhibited almost the same serum IL-6 level as one of the PBS group, which is to demonstrate the biocompatibility of CBA in the systemic administration. Consequently, the CBA encapsulation of Ad particles led to a significant decrease in the serum IL-6 level of Ad-CBA, which is to verify the ability of CBA to protect the Ad particles from the innate immunity.

Figure 8A:
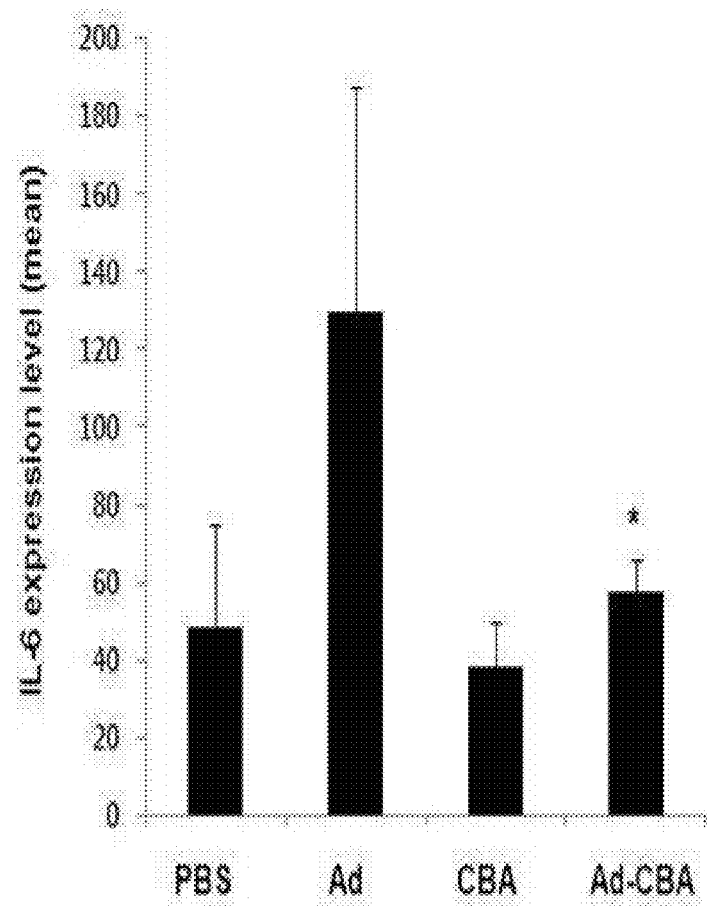
FIGS. 8A-8B are diagrams showing immune reaction and liver cell toxicity evaluation of Ad-CBA.
Figure 8B:
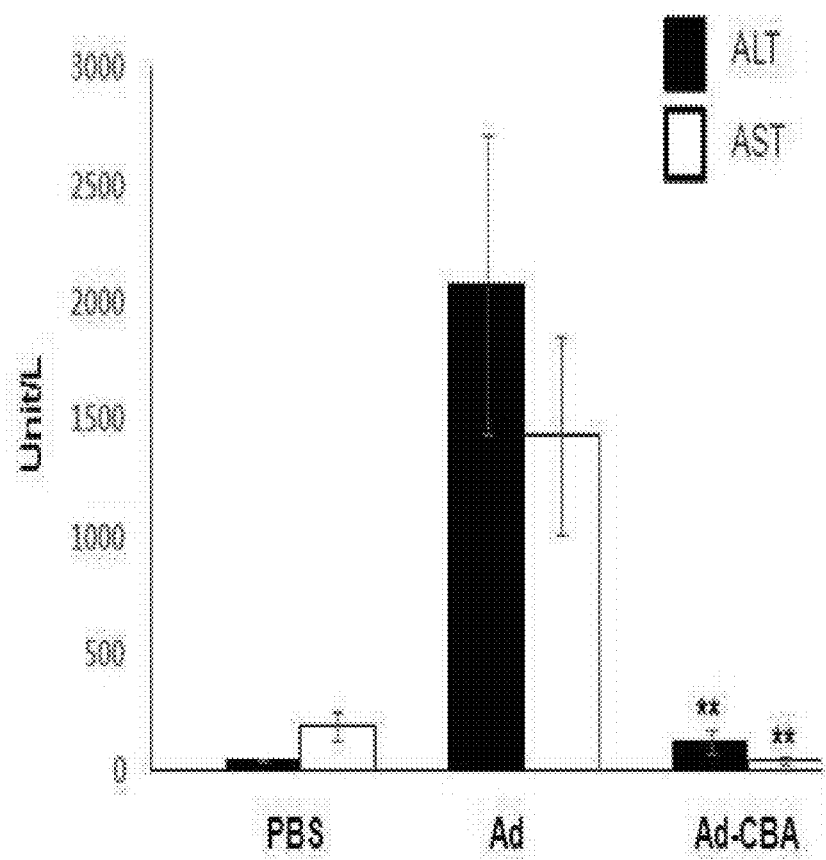

Another contribution factor in the fast removal of Ad in blood is collection of viral particles in liver by Kupffer cells. Large macrophages are specifically located in liver sinusoids, and the liver sinusoids are mostly mediated by scavenger receptors (XU, Z). Cytokines (TNF and IL-6) released by Kupffer cells have been known to cause the initial hepatotoxicity after liver transduction of Ad. In this regard, the degree of hepatotoxicity induced by the Ad-polymer complex is an additional evidence for the ability of the polymer in escape immunity. Thus, the present inventors measured serum levels of alanine aminotransferase (ALT) and aspartate aminotransferase (AST) after intravenous injection of PBS, naked Ad or Ad-CBA (FIG. 8). The naked type Ad group showed a rapid increase in serum ALT/AST levels, but the ALT/AST levels of the Ad-CBA group were lower than the Ad counterpart as 17.1 and 30.5, respectively. The experimental results indicate that the Ad-CBA decreased serum IL-6 and ALT/AST levels through the immune escape properties of the CBA.

9. Anticancer Effect of Intravenously Injected Ad-CBA Complex

Figure 9:
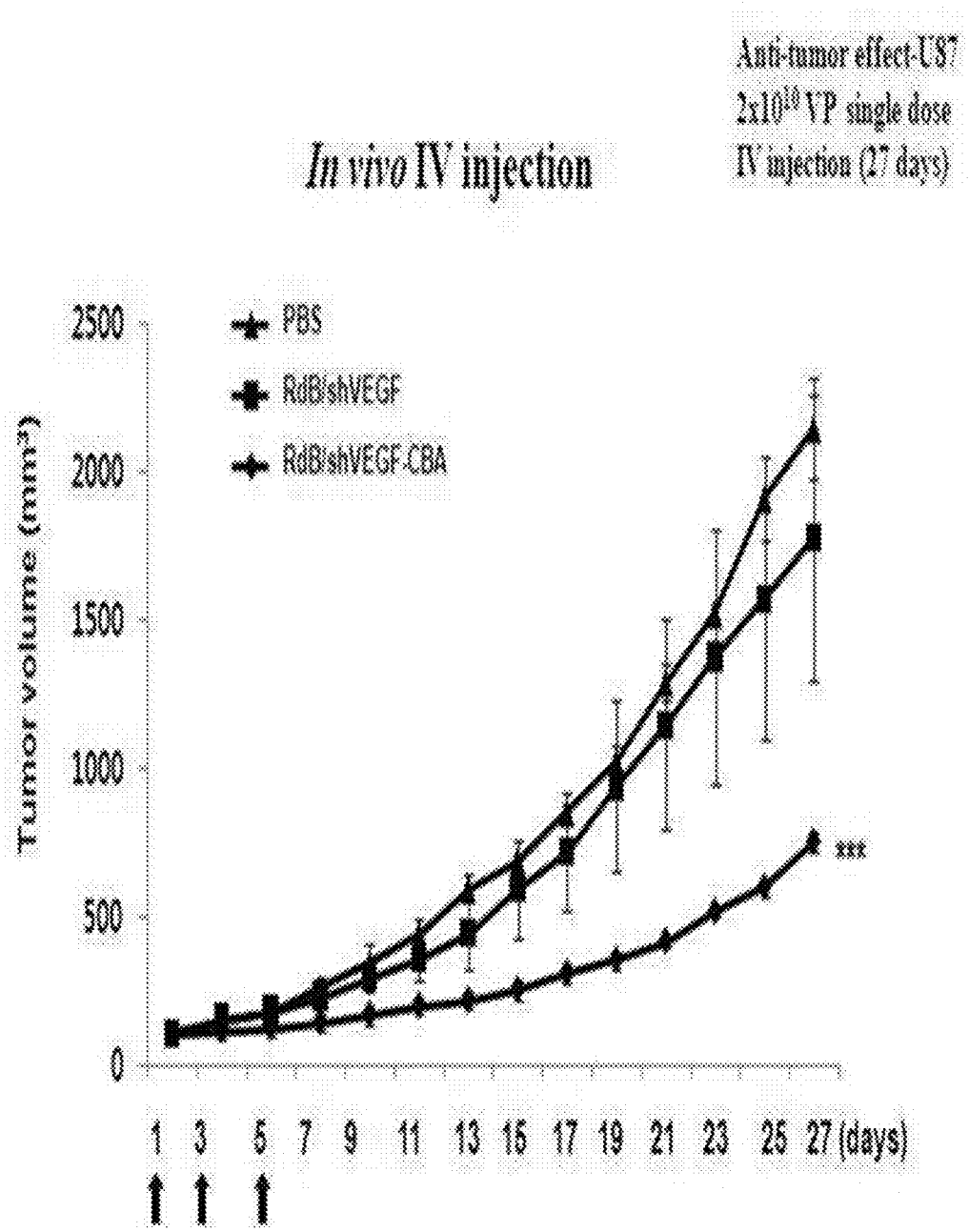
FIG. 9 is a diagram showing the anti-cancer therapeutic effect of the naked type Ad or Ad-CBA complex from U87 glioblastoma tumor xenograft in a nude mouse via intravenous (IV) injection. The subcutaneous tumor transplanted from U87 cells was treated with PBS, RdB/shVEGF (2×10$^{10}$ VP) or RdB/shVEGF-CBA (2×10$^{10}$ VP). The arrows indicate administration of therapeutic amount. Experimental results were expressed as mean±standard error (***P<0.001, RdB/shVEGF-treated group).

Mice bearing U87 xenograft tumors were established to evaluate the anticancer effect of RdB/shVEGF-CBA in systemic administration and treated with PBS, naked Ad or Ad-CBA over 27 days. As shown in FIG. 9, the tumor growth was significantly suppressed in the RdB/shVEGF-CBA compared to the RdB/shVEGF group (P<0.001). On the other hand, the antitumor activity of the naked type RdB/shVEGF was minimized because of the presence of immune reaction to remove the naked type AD in systemic administration. For PBS, RdB/shVEGF and RdB/shVEGF-CBA groups, the average tumor sizes on Day 27 after xenograft subcutaneous injection were 2144±167, 1777±484, 752±35 mm$^3$, respectively. The corresponding tumor growth inhibition for the RdB/shVEGF and RdB/shVEGF-CBA groups was 17.1% and 65.0%, respectively. The experimental results did not only confirm the immune evasion effect of the CBA through encapsulation of Ad particles, but also demonstrated the efficiency of anticancer activity of RdB/shVEGF-CBA, which is to determine the therapeutic potential in the systemic administration of RdB/shVEGF-CBA.

10. Stability and DTT Treatment Effect of the Ad Coated or Uncoated with CBA

Figure 10:
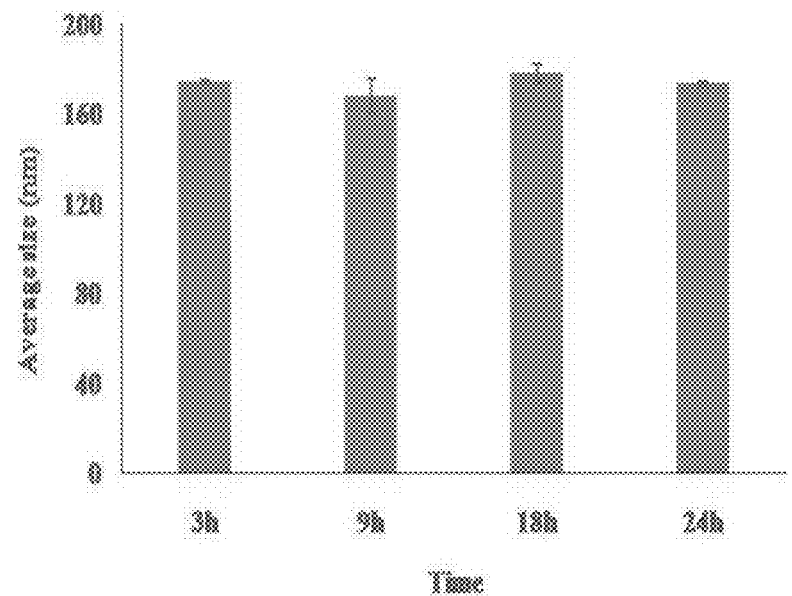
FIG. 10 shows stability test results of Ad coated or uncoated with CBA. Results of average sizes of particles measured by varying measurement time intervals are shown.
Figure 10:
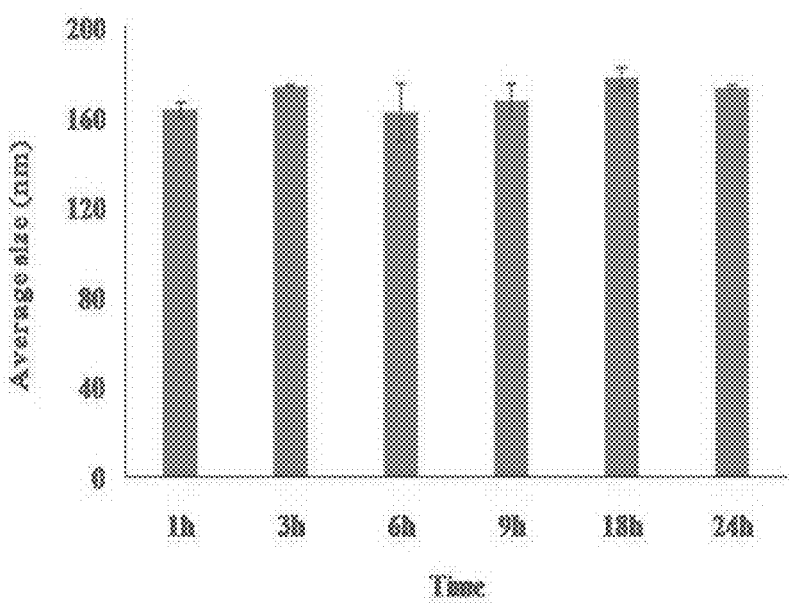
Figure 11:
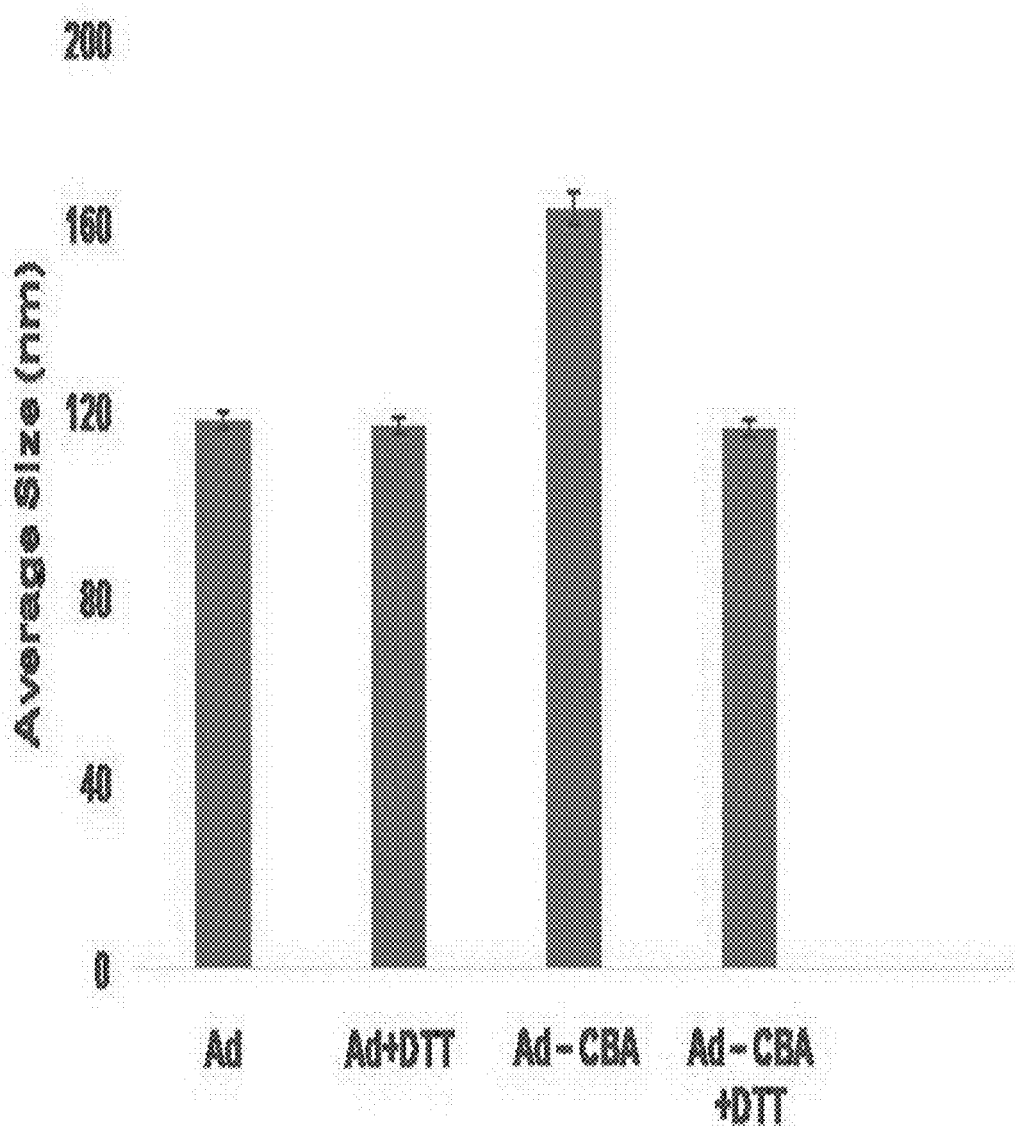
FIG. 11 shows results of average size distribution before/after treating Ad-CBA complex with DTT, measured by DLS.

The colloidal stability of the Ad-CBA nanocomplexes in the PBS buffer was measured at room temperature up to 24 hours. As shown in FIG. 10, the average size of the Ad-CBA nanocomplexes did not significantly change for 24 hours, which means that the CBA cationic polymer-coated Ad shows the good colloidal stability. Also, the reducing character was tested with a reducing agent dithiothreitol (DTT). The particle sizes of uncoated Ad and Ad-CBA, untreated or treated with DTT were measured by a DLS analyzer. As shown in FIG. 11, the size of the uncoated Ad did not change by the DTT treatment. However the average size of the CBA coated Ad complexes significantly decreased after DTT treatment and was close to the size of the uncoated Ad. These results clearly confirm that the CBA can be biodegradable under reducible microenvironment. In conclusion, the above data show that the Ad-CBA has been successfully formed in the complex, prepares particles with a diameter of 200 nm or less and is effectively introduced into cells.

11. Overall Conclusions

The present inventors devised a pH-sensitive and bioreducible polymer and a polymer coating adenovirus systems through ionic interactions in turn and then synthesized them. In addition, it was demonstrated that the transduction increased the gene transfer effect by the pH-dependent method in CAR positive and negative cells. It was determined that in the intracellular entry mechanism of Ad-CBA, the uptake of Ad-CBA through the macropinocytosis path is different from the naked type Ad. In addition, the cell lethal effect data showed that since the polymer coated with Ad has a strong binding affinity with cells and increases the cell uptake of the complex, the Ad-CBA polymer is more significantly higher than the naked type Ad and CBA polymer. Furthermore, the therapeutic effect of the Ad-CBA showed the significantly increased therapeutic effect in intratumorally and intravenously in vivo models as well as in the in vitro study compared to the naked type Ad. Moreover, it is an advantage of the present invention that the success of Ad-CBA can anticipate the development of other Ad complexes using the target characteristics of the tumor microenvironment.

Figure 12:
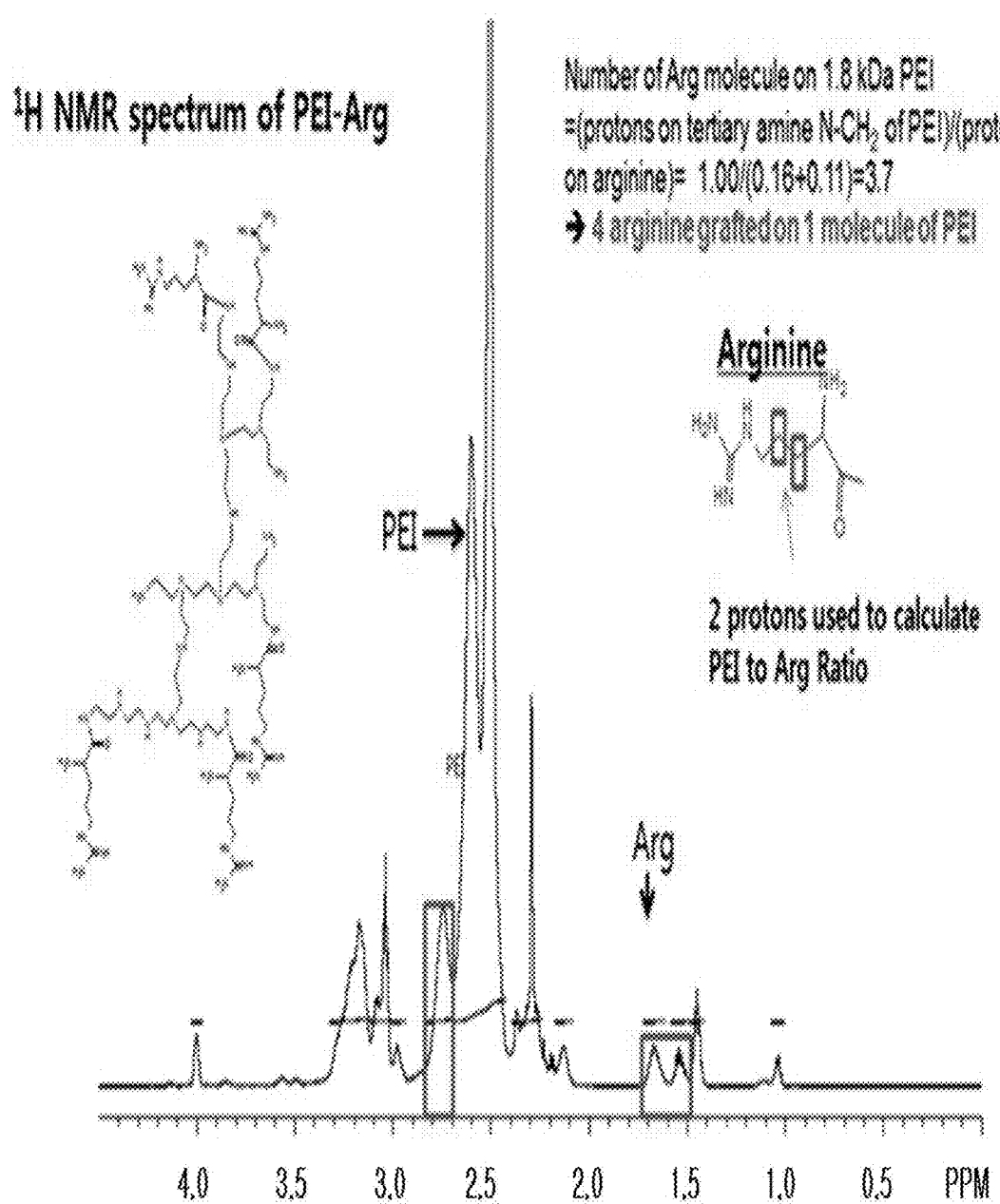
FIG. 12 is a diagram showing $^1$HNMR spectrum of PEI-Arg.
Figure 13:
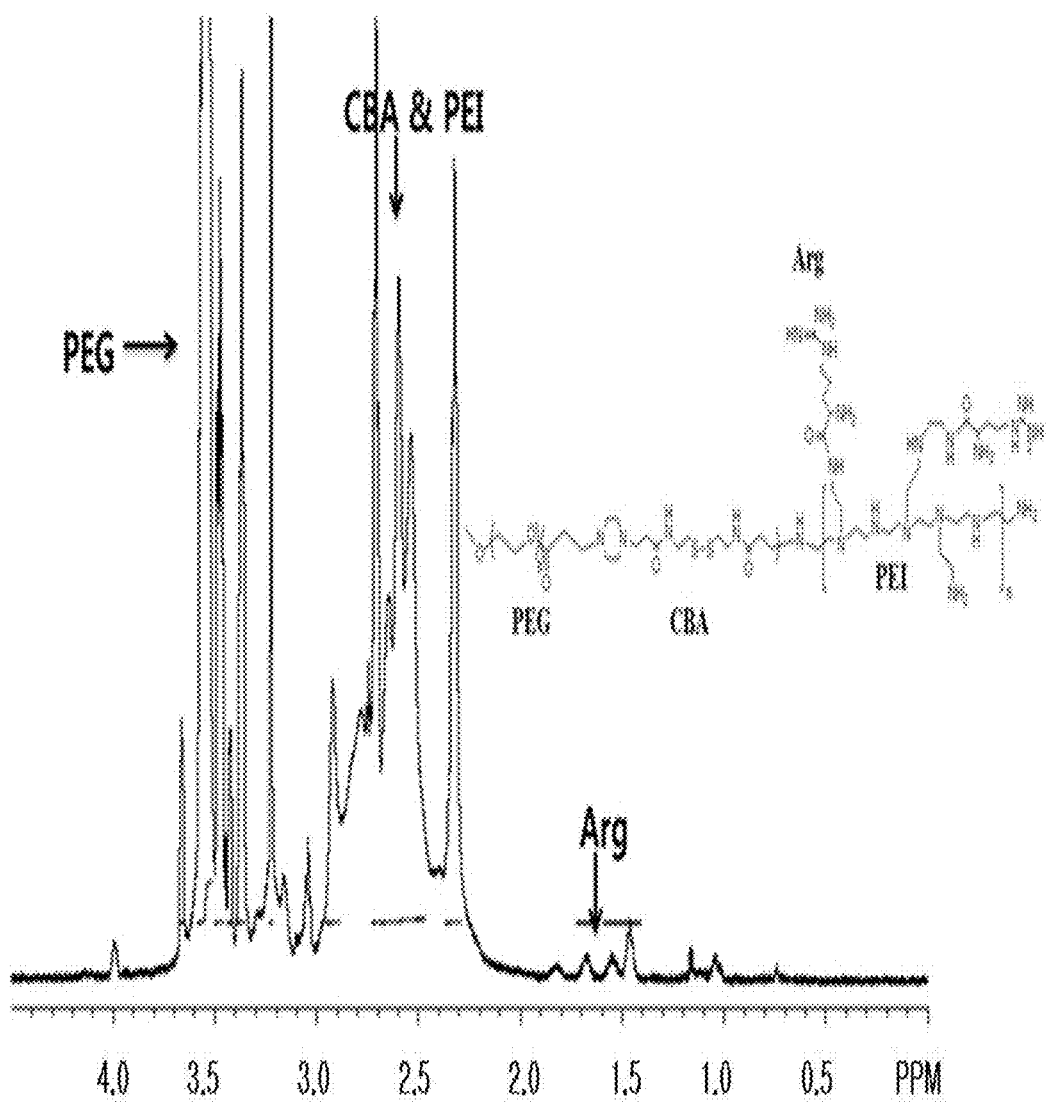
FIG. 13 is a diagram showing $^1$HNMR spectrum of PPR polymer.

II. Utilization of pH-Sensitive and Bioreducible Polymer (CBA) and Ad-CBA Complex 1. Synthesis of CBA-PEI-Arg (PPR) Polymer The inventors produced CBA-PEI-Arg (PPR) polymer by binding arginine (Arg) which was reported to have high cell permeability to the CBA polymer via 1.8 kDa low molecular weight PEI to maximize the cell transfer efficiency of Ad plasmid DNA. First, it could be confirmed that when the PEG-Arg complex was produced to analyze its structure and bond configuration through physical and chemical methods ($^1$H NMR), four Args were bonded to amine groups of 1.8 kDa low molecular weight PEI, as shown in FIG. 12. Then, CBA and PEI-Arg were bonded in a ratio of 1:1 to produce CBA-PEI-Arg polymer (PPR), and by analyzing the structure of the polymer via $^1$H NMR, inherent peaks of each component (PEG, CBA, Arg, etc.) were identified, as shown in FIG. 13, to verify the synthesis of the PPR polymer 2. Evaluation of Stability and Cytotoxicity in CBA-PEI-Arg Polymer (PPR)

In order to determine the stability of the PPR polymer, the size change was confirmed via dynamic light scattering (DLS) analysis in the same 37° C. condition. In addition to this, to determine the cytotoxicity of the PPR polymer, various human cancer cells (liver cancer cell line: Hep-1, pancreatic cancer cell lines: MIA PaCa-2, lung cancer cell lines: A549) and normal cell lines (NIH3T3, HDF) were treated with PBS, 25 kDa PEI, Lipofectamine, CBA polymer, and PPR polymer in various concentrations (0, 1, 2, 5, 10, 20, 50, 100 μg/ml) to perform the MTT assay.

Figure 14:
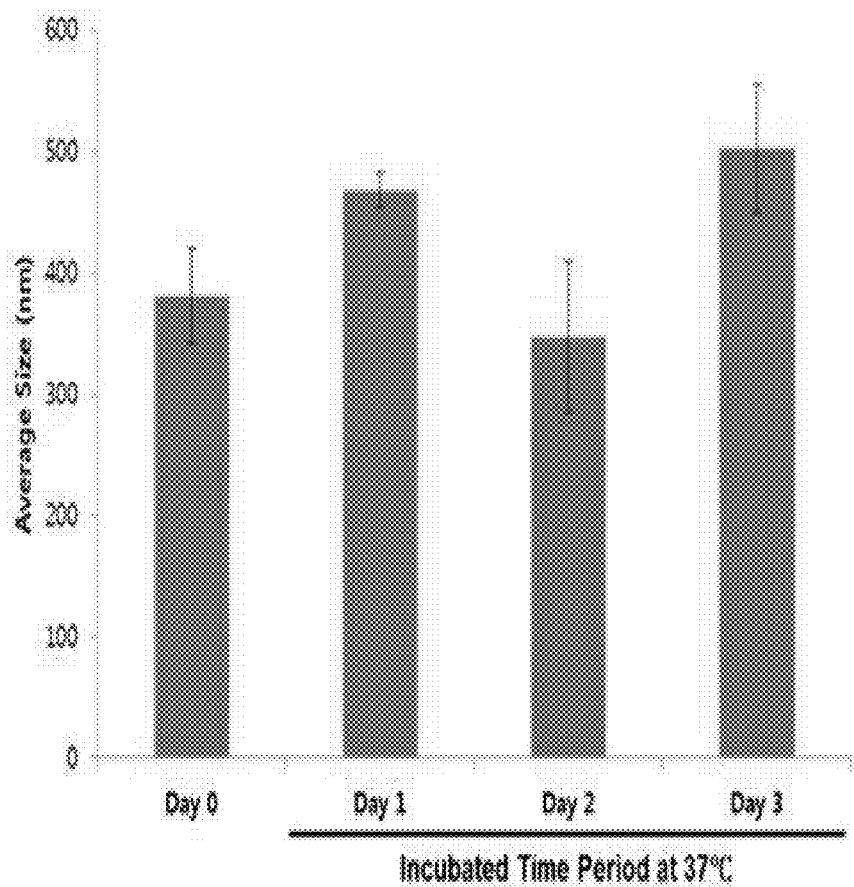
FIG. 14 is a result determining change of the PPR polymer size via DLS analysis in the same 37° C. condition as the in vivo temperature.
Figure 15:
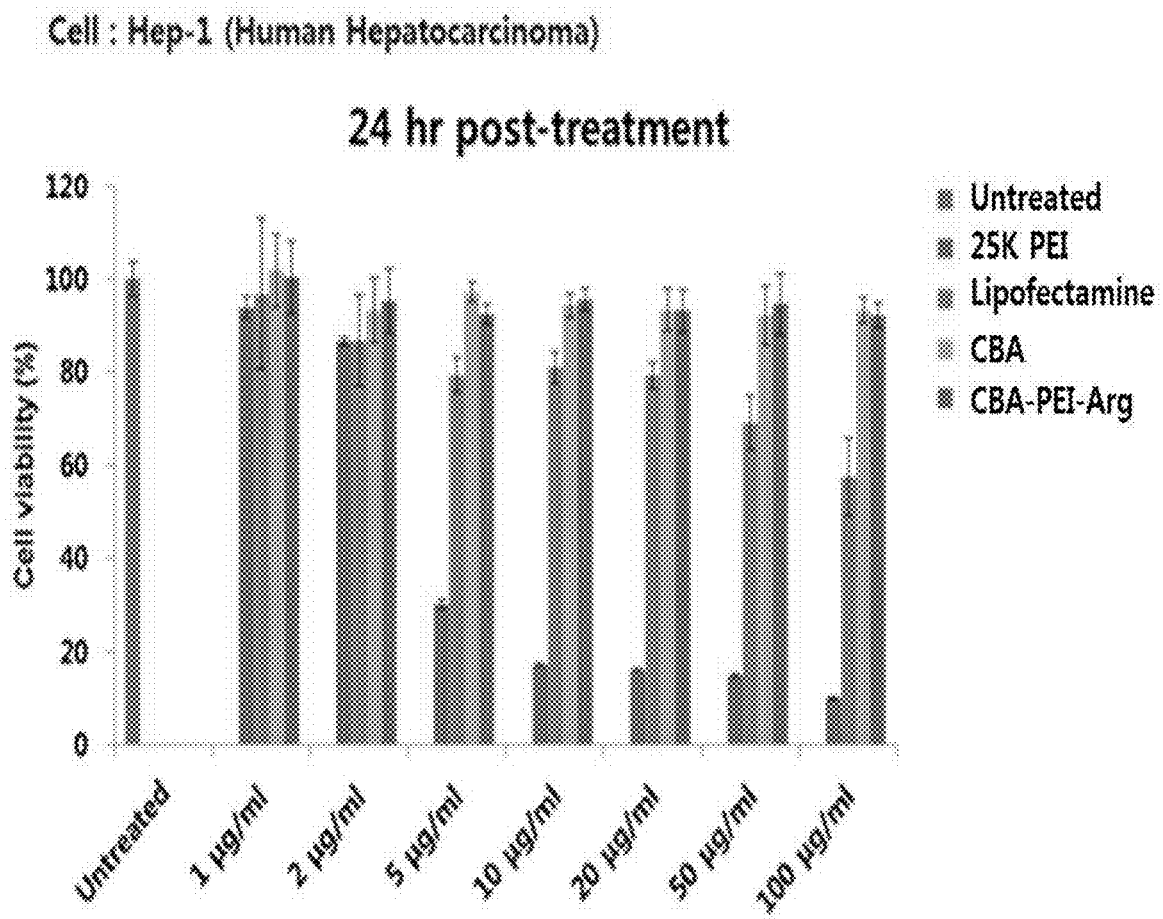
FIG. 15 is a result determining cytotoxcicity of PPR polymer via MTT assay in hepatoma cell lines (Hep-1).
Figure 16:
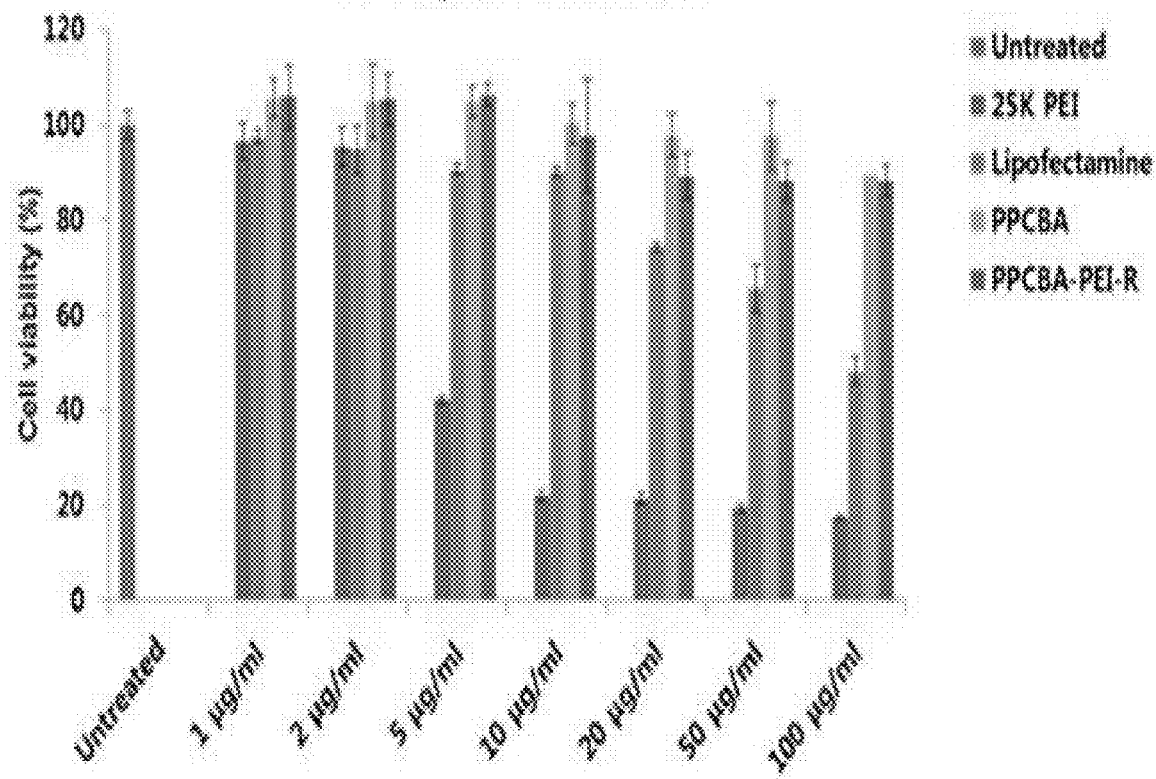
FIG. 16 is a result determining cytotoxcicity of PPR polymer via MTT assay in pancreatic cancer cell lines (MIA PaCa-2).
Figure 17:
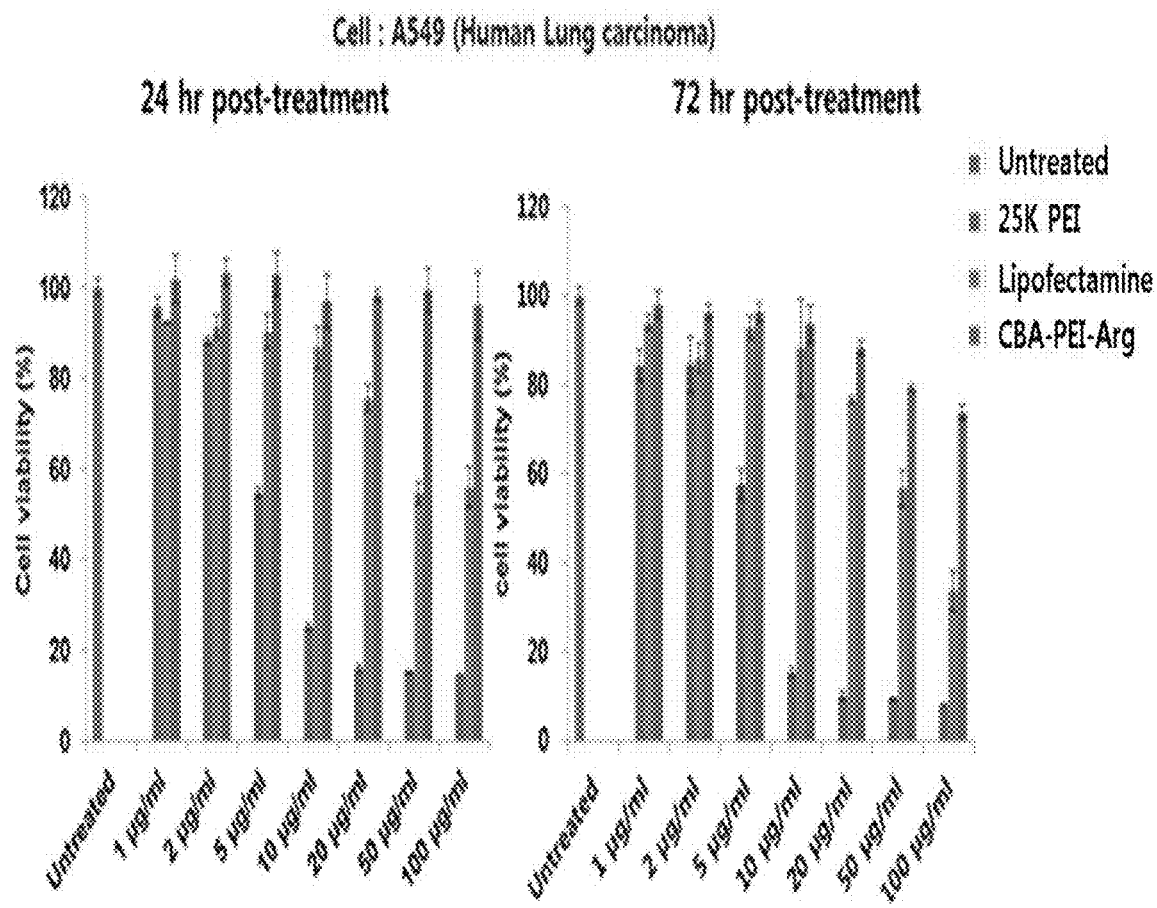
FIG. 17 is a result determining cytotoxcicity of PPR polymer via MTT assay in lung cancer cell lines (A549).
Figure 18:
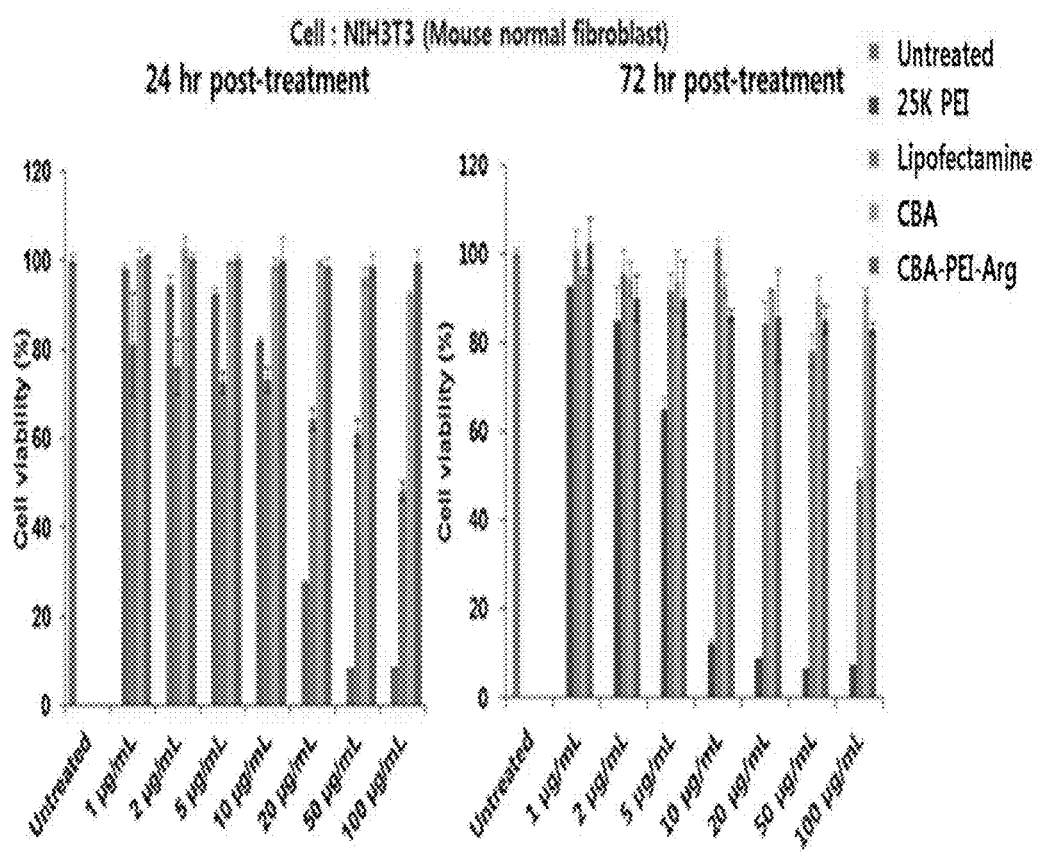
FIG. 18 is a result determining cytotoxcicity of PPR polymer via MTT assay in normal cell lines (NIH3T3).
Figure 19:
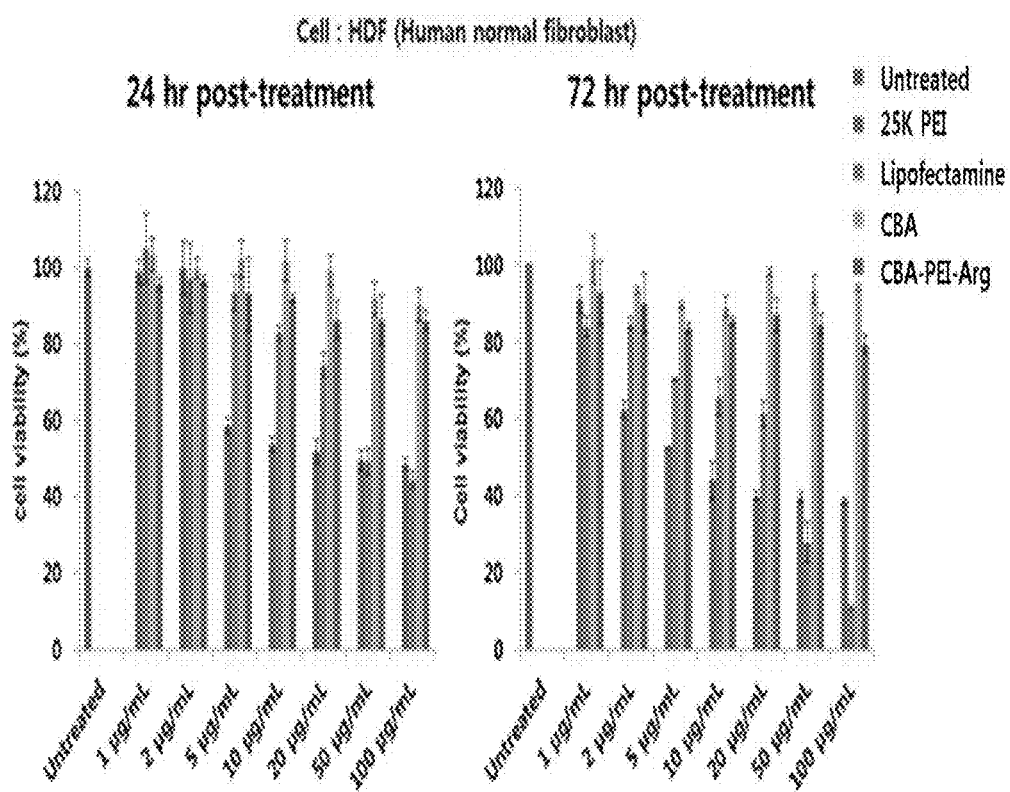
FIG. 19 is a result determining cytotoxcicity of PPR polymer via MTT assay in normal cell line (HDF).

As a result, as shown in FIG. 14, the size of polymer measured after synthesis (Day 0) was 381.0±39.2 nm, and the size after 1 day (Day 1) was measured to 468.3±14.6 nm, the size after 2 days (Day 2) to 347.3±61.7 nm, and the size after three days (Day 3) to 502.1±53.5 nm, whereby it could be confirmed that the structure of the PPR (PPCBA-PEI-Arg) polymer was stably maintained in the in vivo temperature. In addition, as shown in FIGS. 15 to 19, after 24 hours, in the group treated with 25 kDa PEI, both normal cells and tumor cells were confirmed to have high cytotoxicity in spite of a low concentration (5 μg/ml) (Hep-1; 69.7%, MIA PaCa-2; 57.7%, A549; 45.3%, NIH3T3; 7.5%, HDF; 41.5%), and in the case of the Lipofectamine treated group, it was observed to have lower toxicity than 25 kDa PEI at all the concentrations, but on treating with the highest concentration of 100 μg/ml, high cytotoxicity was observed (Hep-1; 6.7%, MIA PaCa-2; 51.8%, A549; 44%, NIH3T3; 51.9%, HDF; 55.4%). On the other hand, for CBA polymer and PPR polymer, they showed significantly low cytotoxicity relative to 25 kDa PEI or Lipofectamine Specifically, after 24 hours, in the case of being treated with CBA polymer or PPR polymer in the highest concentration of 100 μg/ml, low cytotoxicity was also observed in all cases (CBA: Hep-1; 6.7%, MIA PaCa-2; 10.6%, NIH3T3; 7.7%, HDF; 9.6%, CBA-PEI-Arg: Hep-1; 7.8%, MIA PaCa-2; 1.7%, A549; 4%, NIH3T3; 0.4%, HDF; 13.9%). This trend was maintained up to 72 hours, whereby it could be verified that the CBA and PPR polymers were a safe gene transfer material showing low cytotoxicity compared to the existing polymeric material (25 kDa PEI or lipofectamine).

3. Production of Ad-PPR Complex and Ad-Peptide-PPR Complex 3-1. Deduction of Appropriate Ratios for Forming Ad-PPR Complexes Ad-CBA complexes or Ad-PPR complexes were produced by electrostatic coupling between the negatively charged Ad plasmid DNA and the positively charged CBA polymer or PPR polymer. In order to deduct the optimum condition for forming the complexes, it was confirmed whether the complexes were formed according to changes in weight ratios between Ad plasmid DNA and CBA polymer or PPR polymer (Ad DNA:CBA=1:1, 1:10, 1:50, 1:100, 1:250, 1:500, 1:1000, Ad DNA:PPR=1:1, 1:2, 1:5, 1:10, 1:20, 1:50, 1:100).

Figure 20:
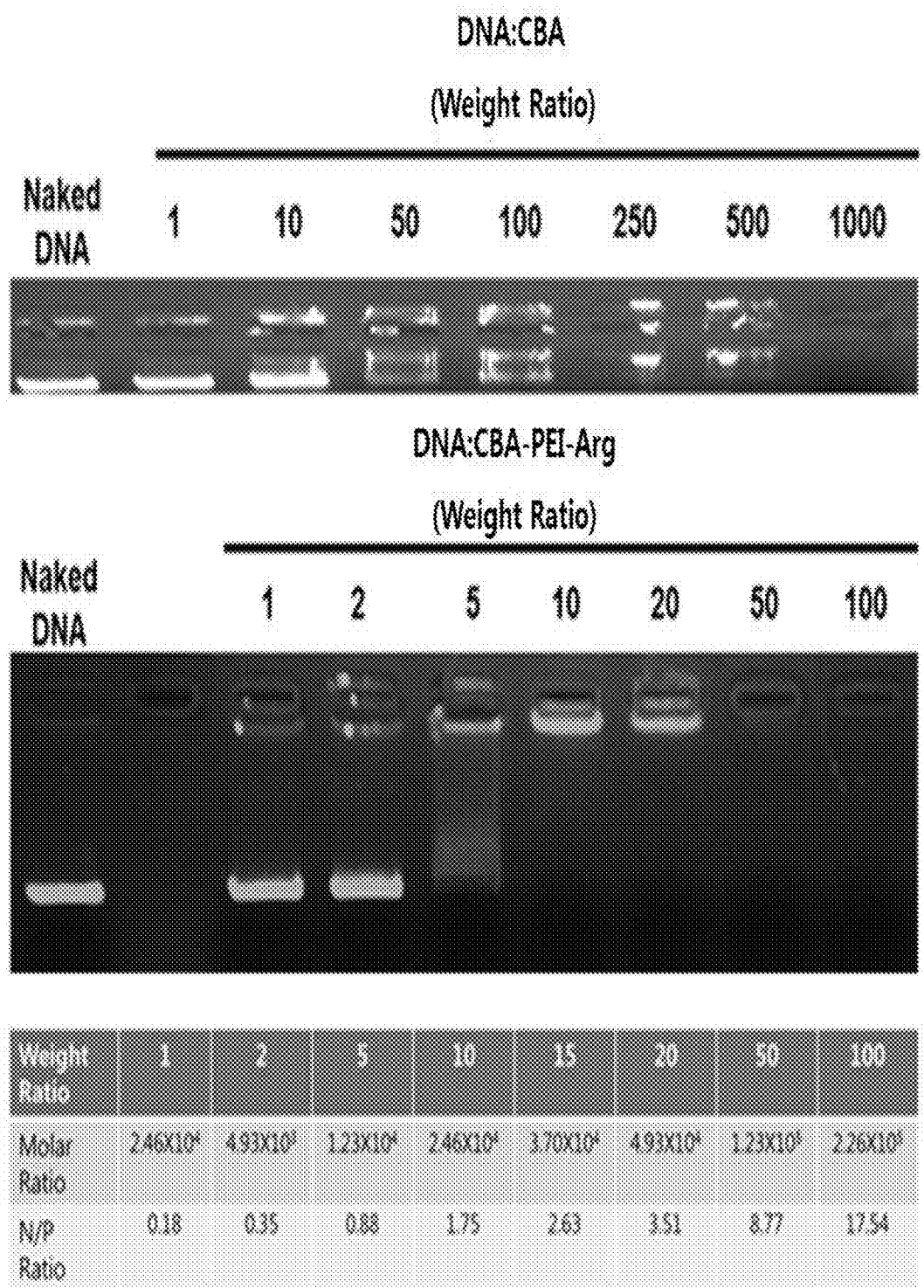
FIG. 20 is a result determining formation of Ad-CBA complexes/Ad-PPR complexes according to changes in weight ratios between Ad plasmid DNA and CBA polymer/PPR polymer.

As a result, as shown in FIG. 20, it could be confirmed that when the weight ratio of Ad DNA:CBA was 1:500 or more, Ad DNA was stably bonded to CBA, and in the case of the Ad-PPR complex, even when the weight ratio of Ad DNA: PPR was 1:10, Ad DNA was stably bonded to PPR. These experimental results show that the PPR polymer forms a stable coupling even in a smaller amount compared to the CBA polymer.

3-2. Physical Property Analysis of Ad-PPR Complex

In order to analyze physical and chemical properties of Ad-CBA and Ad-PPR complexes, the average size and surface charge of each complex were measured by performing DLS and zeta potential.

Figure 21:
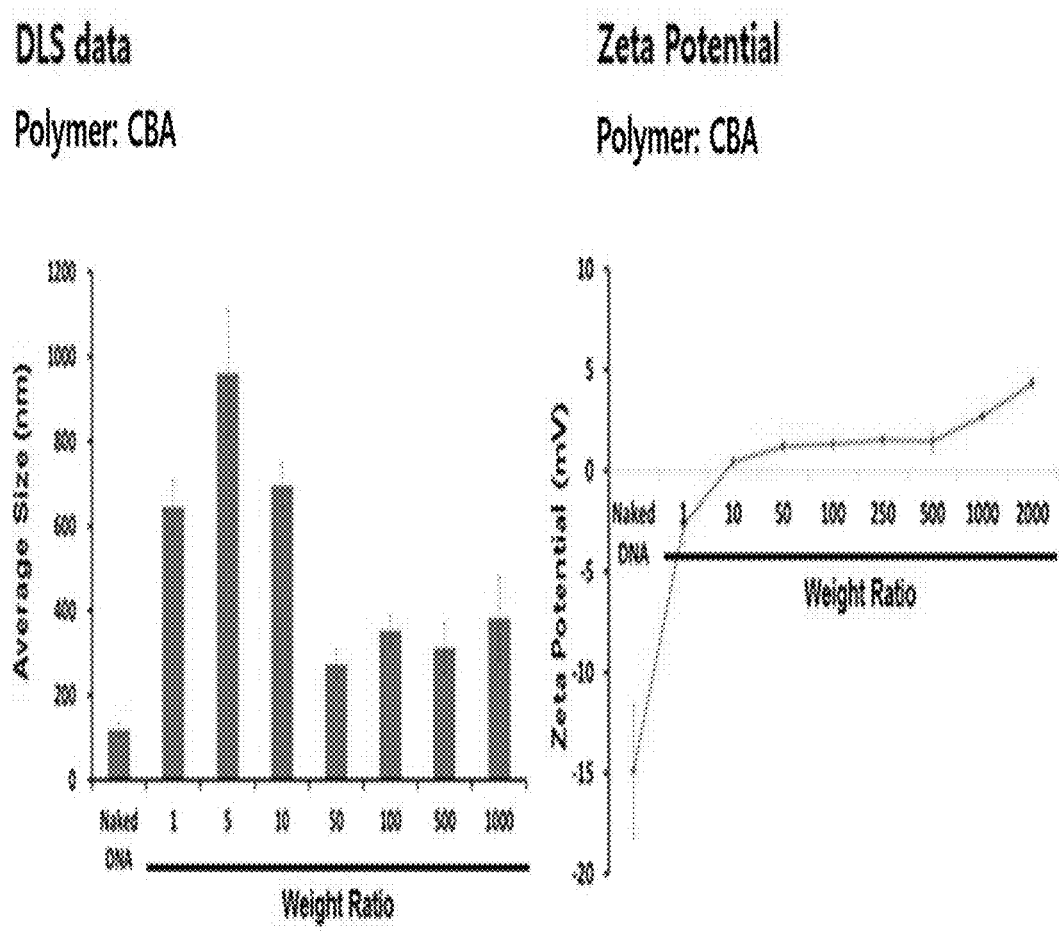
FIG. 21 is a result determining physical and chemical properties of Ad-CBA complexes through DLS and zeta potential.
Figure 22:
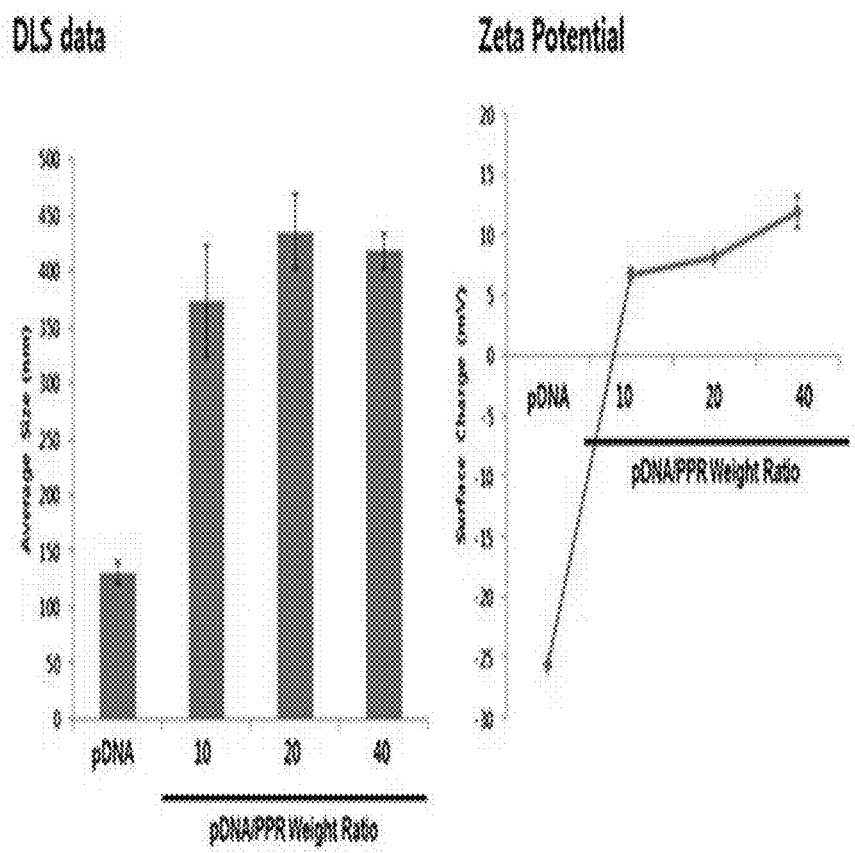
FIG. 22 is a result determining physical and chemical properties of Ad-PPR complexes through DLS and zeta potential.

As a result, as shown in FIG. 21, it was confirmed that the average size of the oncolytic Ad DNA forming no complex was 130.8±16.1 nm, but when forming complexes with CBA, the size gradually increased, as the weight ratio of Ad DNA:CBA increased from 1:1 to 1:5, and in the case of 1:50 or more, the size was stably maintained in around 350 nm on average. In zeta potential analysis, the naked Ad DNA had about −15 mV, but was observed to have positive charges from the weight ratio of Ad DNA:CBA of 1:10 by gradually increasing the charge amount with increasing the concentration of CBA, where the surface charge represented about +5 mV at the highest weight ratio (1:2000). In addition, as shown in FIG. 22, it could be confirmed that when the weight ratio of Ad DNA and PPR polymer is 1:10, 1:20, or 1:40, the size of Ad-PPR complexes is in average 400 nm or less and thus the micelle structure is stably maintained, and it can be seen that as the weight ratio of Ad DNA:PPR increases to 1:10, 1:20, 1:40, the surface charge increases depending on the concentration of PPR to 6.7±0.4 mV, 8.1±0.1 mV, 11.9±1.3 mV, respectively. These experimental results show that the complexes having a stable size and positive charges are formed even when the PPR polymer is used in much lower amount compared to CBA polymer.

3-3. Production of Ad-Peptide-PPR Complex

The peptide used in the present invention is an adenovirus-derived peptide consisting of SEQ ID NO: 1 (AF-SWGCLWSCIKNFGFCGALAERKKRRQRRR), which was introduced in order to promote the endosomal escape efficiency. In the case of dimeric peptide, it was produced by using the air oxidation technique. Specifically, 2 mg of monomer peptide was dissolved in 2 mL of 0.1M ammonium bicarbonate, and then the mixture was stirred at room temperature for 24 hours in a lid open condition. Then, after the monomer peptide was separated using a dialysis cassette, the remaining reactants were powdered through freeze-drying and used. Finally, the Ad-peptide-PPR complexes were produced by reacting Ad plasmid DNA and peptide in a weight ratio of 1:0.005 to 1:0.015 at room temperature for 10 minutes and then mixing Ad plasmid DNA and PPR polymer in a weight ratio of 1:30 to be again reacted at room temperature for 20 minutes.

4. Verification of Virus Production Ability and Killing Ability in Cancer Cells

To verify virus particle production ability and cancer cell killing ability of Ad-PPR complexes and Ad-peptide-PPR complexes, Ad-PPR (1:30) and Ad-peptide-PPR (1:0.01:30, 1:0.05:30) complexes were produced through coupling Ad DNA of tumor-selective oncolytic adenovirus expressing IL-12 (SEQ ID NO: 2) and GM-CSF (SEQ ID NO: 3) and polymeric materials (PPR or peptide/PPR). Ad DNA, PPR, peptide, Ad-Lipofectamine, Ad-PPR (1:30), or Ad-peptide-PPR (1:0.01:30, 1:0.05:30) complexes were treated in PC-3 being human prostate cancer cell lines to obtain a supernatant after 96 hours, from which Q-PCR was performed to determinate virus production ability and MTT assay being subject to cells in the supernatant was performed to determinate cancer cell killing ability. Next, the virus production ability and cancer cell killing ability of Ad-PPR complexes or Ad-peptide-PPR complexes were verified using HapTi being hamster pancreatic cell lines allowing for growth of virus. To this end, Ad DNA, PPR, peptide, Ad-Lipofectamine and Ad-PPR, or Ad-peptide-PPR (1:0.01:30, 1:0.05:30) complexes, were treated in the HapT1 cell lines, and then on Day 6, Q-PCR and MTT assay were carried out.

Figure 23A:
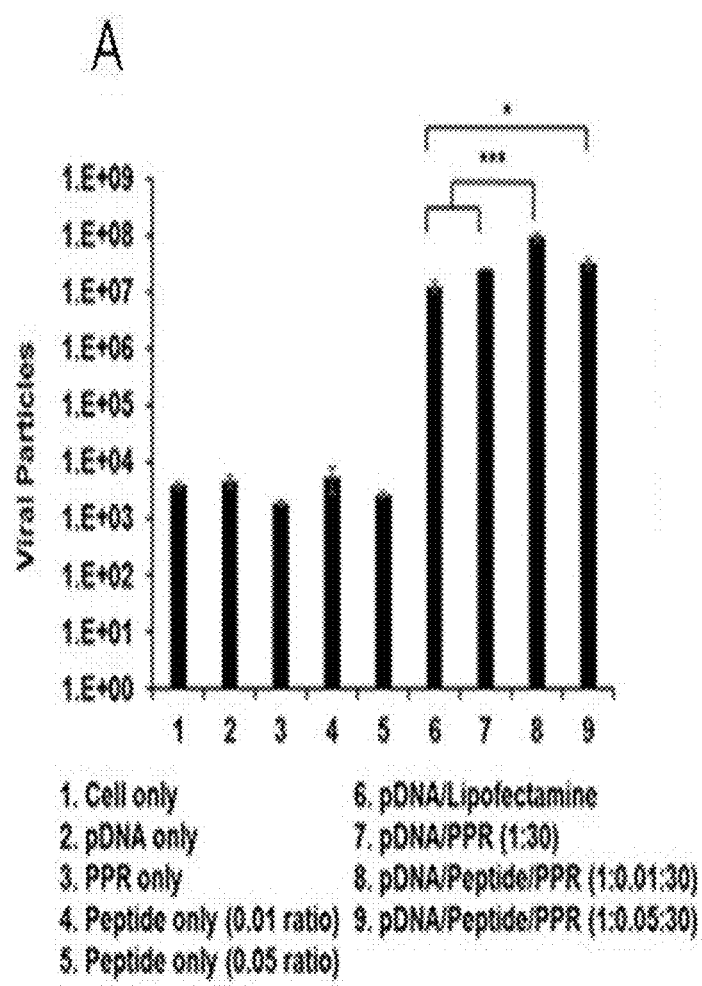
FIGS. 23A-23B identify an excellent virus particle production ability and cancer cell killing ability of Ad-PPR complexes or Ad-peptide-PPR complexes, where
Figure 23B:
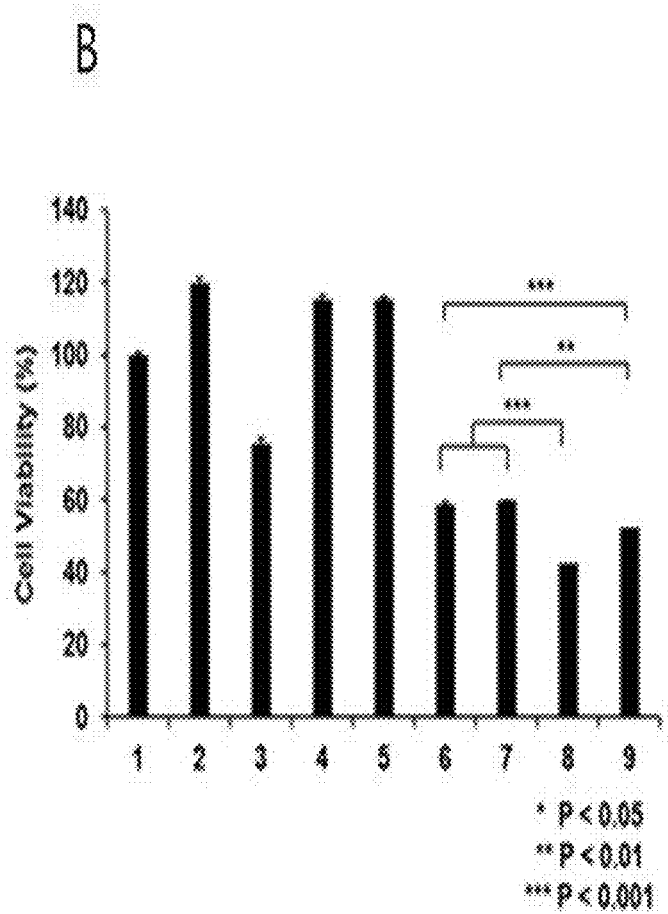
Figure 24A:
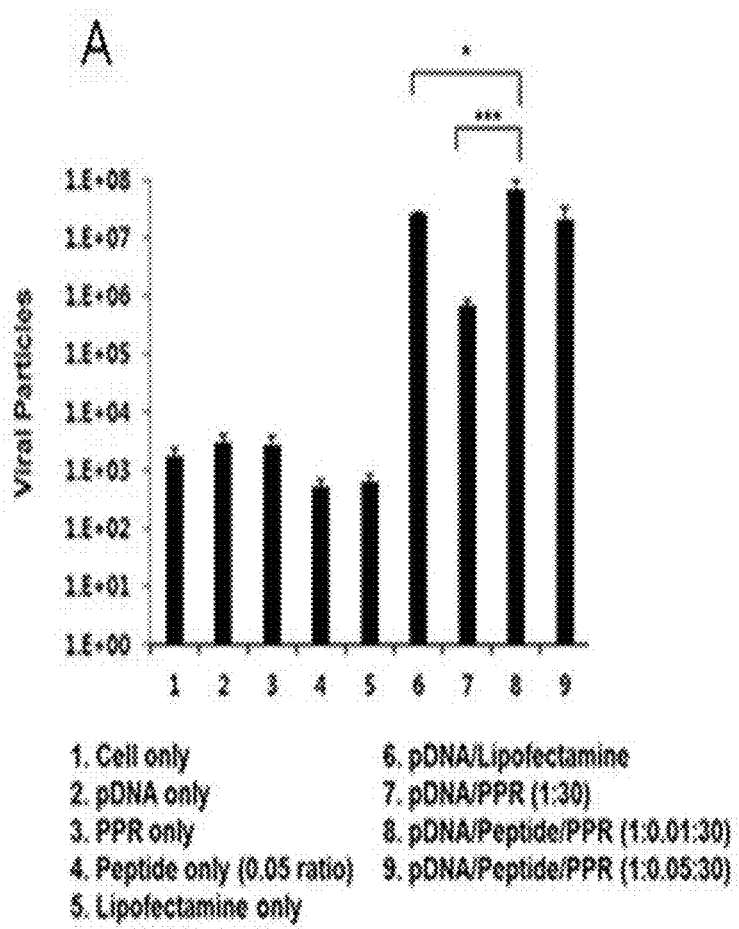
FIGS. 24A-24B identify an excellent virus particle production ability and cancer cell killing ability of Ad-PPR complex or Ad-peptide-PPR complexes using HapT1, which is hamster pancreatic cancer cell lines allowing for viral growth, where
Figure 24B:
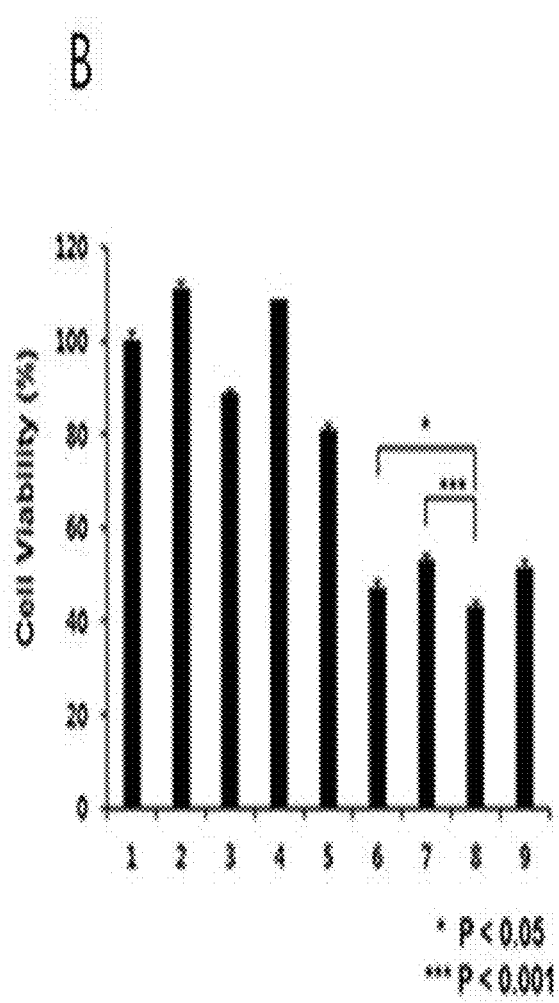

As a result, as shown in FIG. 23, in the case of being treated with Ad DNA only, it showed the number of viral particles similar to PBS, PPR only, but when the polymer such as lipofectamine, PPR, or peptide-PPR formed complexes with Ad DNA, the number of viral particles was observed as $1.2\times10^7$VP, $2.5\times10^7$VP, or $9.3\times10^7$VP, each of which is a value increased about 2695 times, about 5323 times and about 19858 times compared to the group treated with Ad DNA only. In particular, in the case of Ad DNA-peptide-PPR (1:0.01:30, 1:0.05:30) complexes, it also showed an increased virus production ability compared to the case of being treated with Ad-Lipofectamine, which is to show the excellent virus production ability of Ad DNA-peptide-PPR complexes. Furthermore, when analyzing the cancer cell killing ability, the group treated with Ad-peptide-PPR complexes showed the best excellent cancer killing ability, and inter alia when the peptide ratio is 0.01, it showed the highest cancer cell killing ability (57.6%). In addition, as shown in FIG. 24, if only Ad DNA was treated, it showed the number of viral particles almost similar to PBS, PPR only, but if Ad-PPR or Ad-peptide-PPR (1:0.01:30) was treated, it highly increased the virus production ability compared to Ad DNA. In particular, in the case of Ad-peptide-PPR (1:0.01:30) complexes, the number of viral particles is $6.5\times10^7$VP, which increased 23260 times compared to Ad DNA. These results are consistent with the verifying results of virus production ability in human prostate cancer cell lines as previously carried out, and thus the excellent virus production ability could be confirmed. Moreover, even in MTT results, the cancer cell killing ability of Ad-PPR or Ad-peptide-PPR (1:0.01:30) complexes is 47%, 57.3%, respectively, and thus it can be seen that it outstandingly increases compared to Ad DNA (0%). Consequently, the viral replication successfully occurs in cancer cells with Ad-PPR or Ad DNA-peptide-PPR, and as a result, it can be seen that the virus production ability in cancer cells and cancer cell killing ability significantly increase.

5. Determination of Antitumor Effect on Human Lung Cancer Cell Lines (H460)

In order to confirm the anti-tumor effect of Ad-peptide-PPR complexes, H460 ($5\times10^6$ cells/50 µl), which is human lung cancer cell lines, was subcutaneously injected to a mouse to prepare a tumor model. Then, when the tumor size reached about 100 mm$^3$, the change of tumor size was observed for 15 days, while repeatedly administrating the complexes formed by reacting oncolytic Ad DNA and peptide at a weight ratio of 1:0.1 or 1:1 intratumorally every other day.

Figure 25:
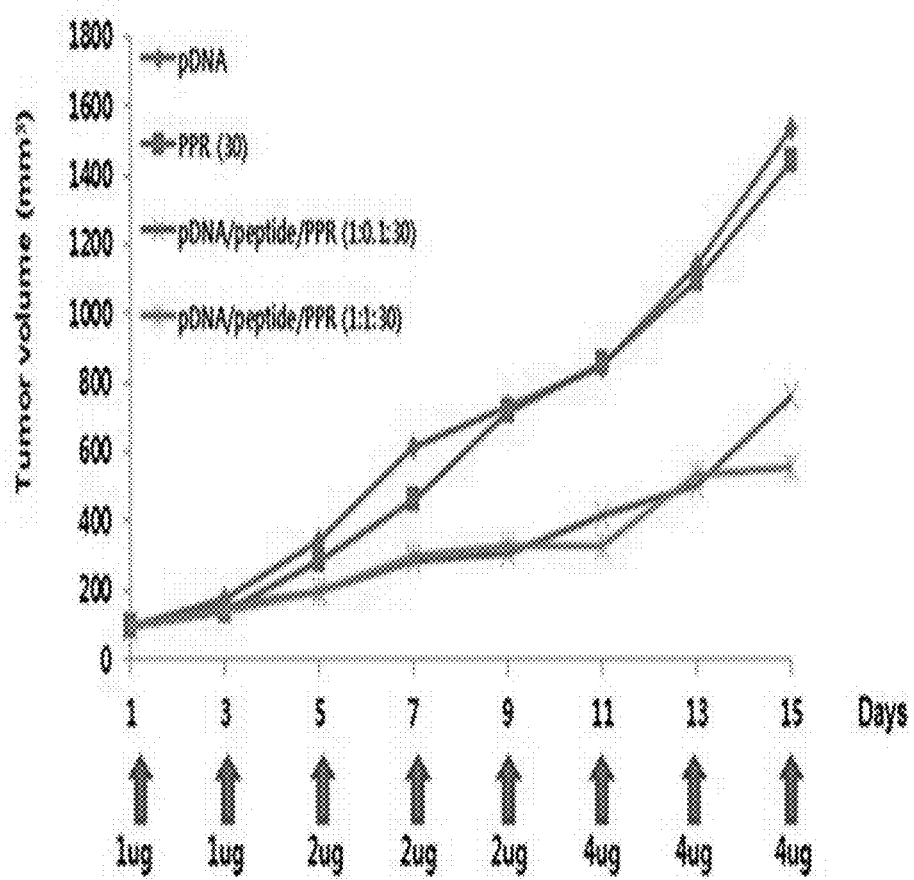
FIG. 25 is a result determining anti-tumor effect of Ad-peptide-PPR complexes on human lung cancer cell lines through change in the tumor size.

As a result, as shown in FIG. 25, it can be seen that the tumor in the group treated with Ad pDNA or PPR only had been continuously grown after 15 days to a size of 1537.8 mm$^3$, 1439.4 mm$^3$, respectively, while the group treated with Ad-peptide-PPR complexes was 762.3 mm$^3$ (peptide 0.1 treated group), 556.3 mm$^3$ (peptide 1 treated group), so that the tumor growth rate was outstandingly reduced.

6. Determination of Anti-Tumor Effect on Human Breast Cancer Cell Lines (SKBR3)

In order to confirm the anti-tumor effect of Ad-peptide-PPR complexes, SKBR3 ($1\times10^7$ cells/50 µl), which is human breast cancer cell lines, was subcutaneously injected to a mouse to prepare a tumor model. Then, the change of tumor size was observed for 15 days, while repeatedly administrating Ad pDNA, PPR, peptide or Ad-peptide-PPR (weight ratio: 1:0.1:30) complexes intratumorally once per two days.

Figure 26:
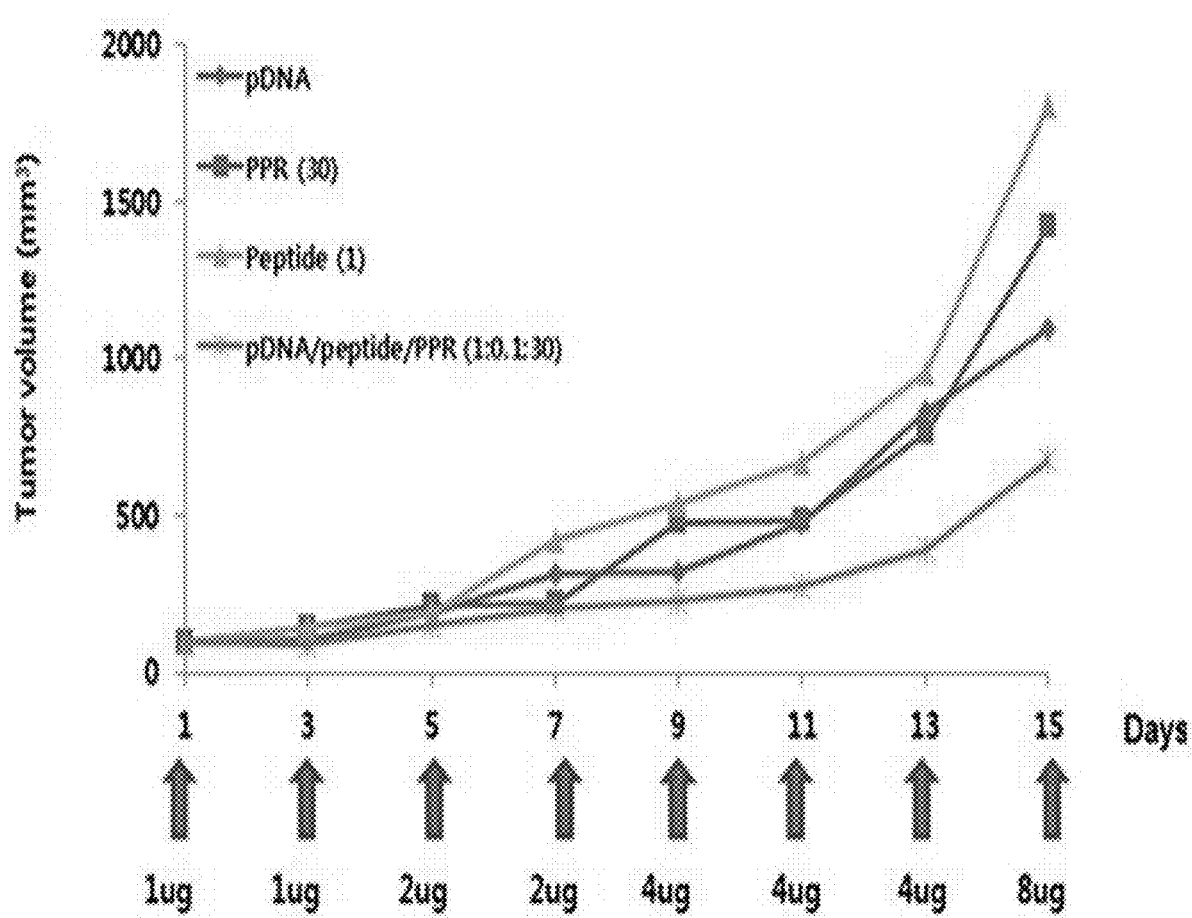
FIG. 26 is a result determining anti-tumor effect of Ad-peptide-PPR complexes on human breast cancer cell lines through change in the tumor size.

As a result, as shown in FIG. 26, it can be seen that the tumor in the group treated with Ad pDNA, PPR or peptide only had been continuously grown after 15 days to a size of 1098.3 mm$^3$, 1419.4 mm$^3$, and 1811.4 mm$^3$, respectively, while the size in the group administrating Ad-peptide-PPR complexes was 674.5 mm$^3$, so that it was reduced 61.4% compared to the group treated with Ad DNA.

7. Determination of Anti-Tumor Effect on Human Uterine Cancer Cell Lines (C33A)

7-1. Changes in Tumor Size

In order to confirm the anti-tumor effect of Ad-PPR or Ad-peptide-PPR complexes, C33A ($1\times10^7$ cells/50 µl), which is human uterine cancer cell lines, was subcutaneously injected to a mouse to prepare a tumor model. Then, when the tumor size reached about 100 mm$^3$, the change of tumor size was observed for 27 days, while repeatedly administrating PBS, Ad pDNA, PPR, peptide, Ad-PPR complexes using oncolytic Ad DNA intratumorally once per two days (n=6).

Figure 27:
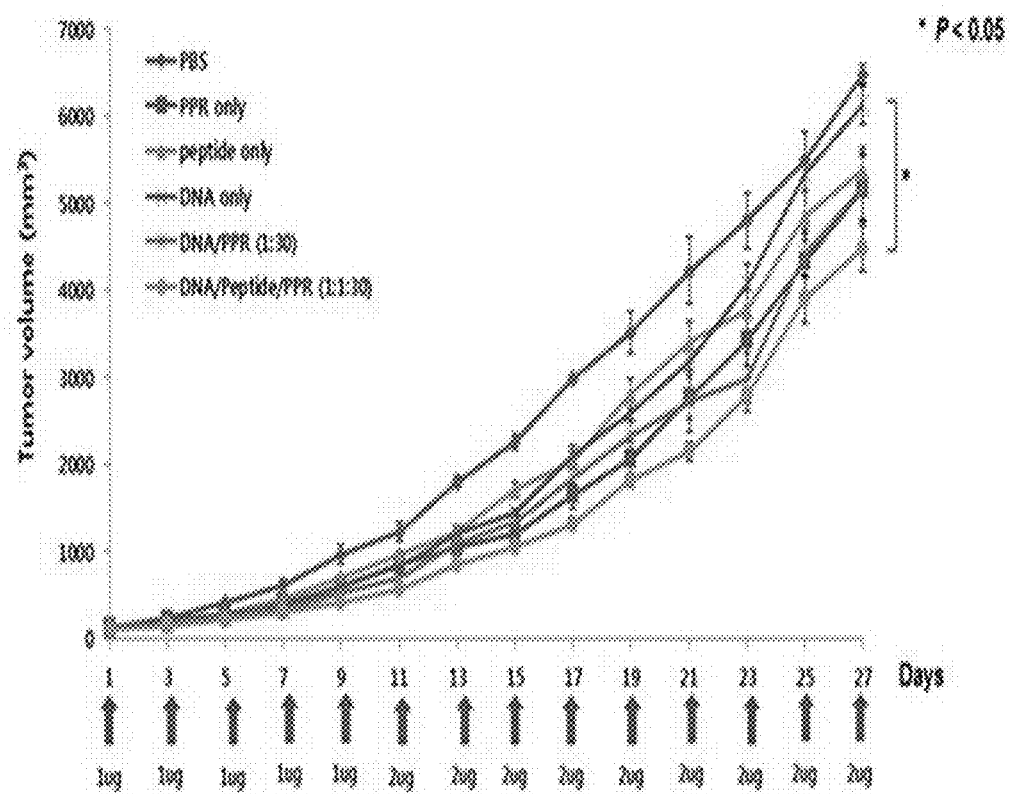
FIG. 27 is a result determining anti-tumor effect of Ad-PPR or Ad-peptide-PPR complexes on human uterine cancer cell lines through change in the tumor size.

As a result, as shown in FIG. 27, the size of tumor in the group treated with PBS and Ad DNA was average 6484.2 mm$^3$ and 6120.7 mm$^3$, respectively, and thus the tumor had been continuously grown, while in the case of the group treated with Ad-PPR complexes, the size of tumor was 5192.9 mm$^3$, so that it was reduced 20% compared to the group treated with PBS. In addition, in the case of the group treated with Ad-peptide-PPR complexes, it can be seen that the size of tumor is 4483 mm$^3$, so that it is reduced 30% compared to the group treated with PBS (P<0.05).

7-2. Changes in Virus Growth Ability

To determine the increased amount of Ad DNA in tumor tissues treated with Ad-PPR or Ad-peptide-PPR complexes, the tumor tissues treated with Ad-peptide-PPR complexes, and the like were extracted and dissolved, and then the DNA purification process was progressed. After quantifying DNA obtained through this, a sample was prepared by 50 ng and then the Q-PCR was progressed using a primer (XI) specific to adenovirus.

Figure 28:
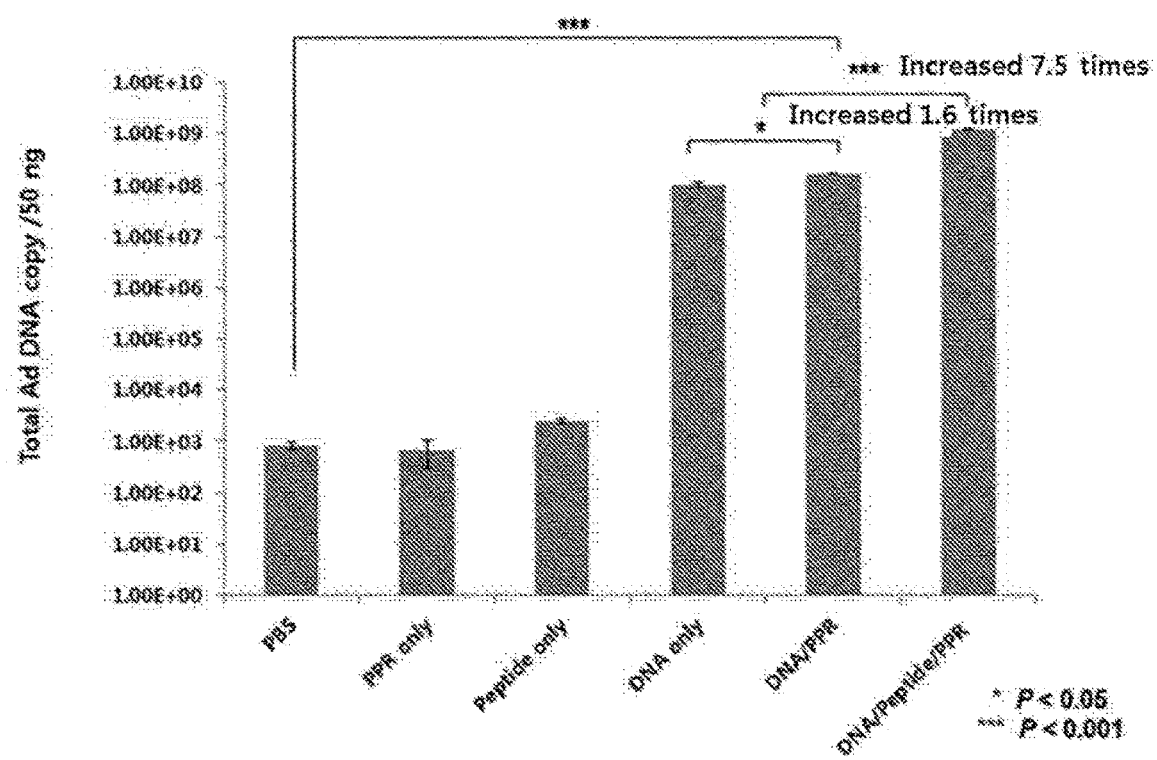
FIG. 28 is a result determining the increased amount of Ad DNA in the tumor tissues treated with Ad-PPR or Ad-peptide-PPR complexes.

As a result, as shown in FIG. 28, a large amount of Ad DNA was detected in the group treated with Ad-PPR or Ad-peptide-PPR complexes and, in particular, the viral DNA amount in the group treated with Ad-peptide-PPR complexes was observed to be 1.2×10$^9$VP, which is a value increased 12 times, 7.5 times, respectively, compared to the group treated with Ad DNA or Ad-PPR complexes. Therefore, when being treated with Ad-PPR or Ad-peptide-PPR complexes, it can be seen that the virus production and replication more effectively occur in tumor tissues.

7-3. Change in Expression Level of Therapeutic Genes

To determine expression levels of therapeutic genes in the tumor tissues treated with Ad-PPR or Ad-peptide-PPR complexes, the tumor tissues treated with Ad-peptide-PPR complexes, and the like were extracted to progress ELISA for TRAIL of a therapeutic gene.

Figure 29:
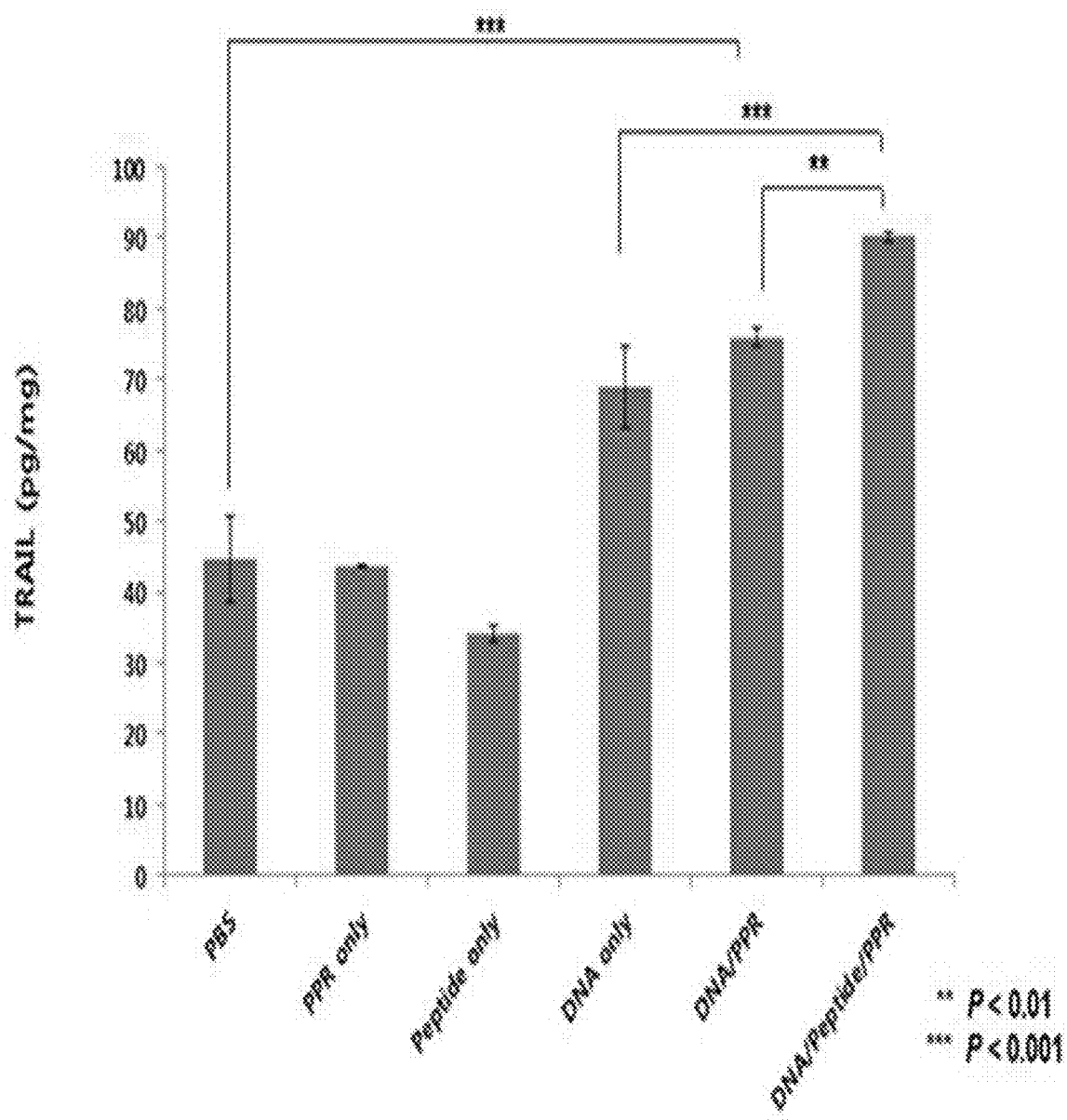
FIG. 29 is a result determining the expression level change of TRAL in the tumor tissues treated with Ad-PPR or Ad-peptide-PPR complexes.

As a result, as shown in FIG. 29, when PBS, PPR, or peptide was treated, TRAIL was detected in 40 pg/mg or less on average, while the TRAIL expression of 69 pg/mg could be confirmed in the group treated with Ad pDNA, and the TRAIL expression of 76 pg/mg in the group treated with Ad-PPR complexes. In particular, in the case of Ad DNA/peptide/PPR complexes, it was 90.2 pg/ml, so that the outstandingly increased TRAIL expression could be confirmed compared to the group treated with PBS, PPR, or peptide. Thus, it can be seen that the treatment of Ad-PPR or Ad-peptide-PPR complexes can improve the expression of tumor tissue-specific TRAIL genes as well as increase in the growth of virus in tumor tissues.

7-4. Change in Intratumoral Tissues

In order to observe changes in tumor tissues by Ad-PPR or Ad-peptide-PPR complexes, H & E staining and TUNEL assay were carried out. In order to compare necrosis of the tumor tissues according to the treated group, the extracted tumor tissues were stained with H & E solutions and observed.

Figure 30A:
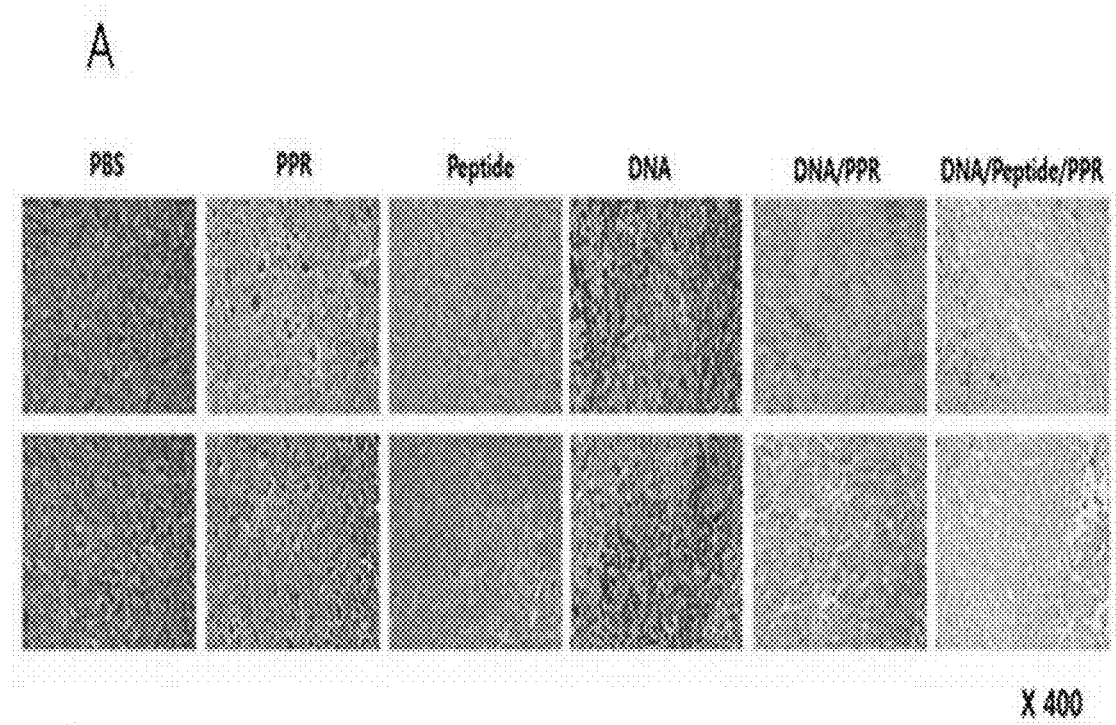
FIGS. 30A-30B are views observing change in the tumor tissues by Ad-PPR or Ad-peptide-PPR complex, where
Figure 30B:
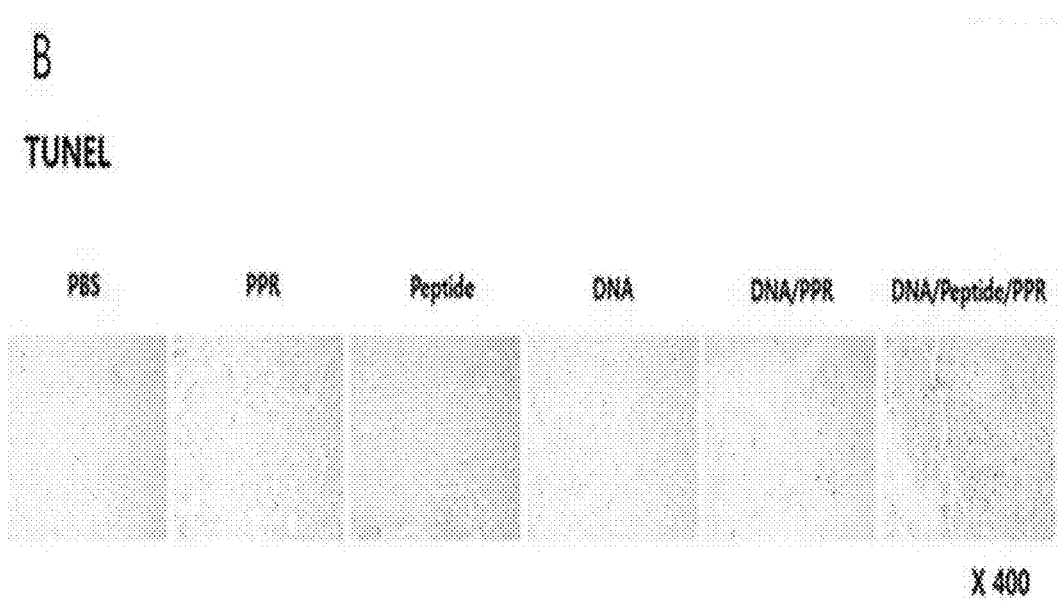

As a result, as shown in FIG. 30, it could be confirmed that the degree of necrosis in the tumor tissues treated with Ad-PPR or Ad-peptide-PPR complexes is highly increased compared to the group treated with PBS, PPR, or peptide. Furthermore, even when comparing the necrosis degree in the tumor tissues through TUNEL assay, a large number of TUNEL-positive spots could be confirmed in the tissues treated with Ad-peptide-PPR complexes. That is, it means that the intratumoral transfer and replication of Ad DNA by treatment of Ad-PPR or Ad-peptide-PPR complexes were effectively developed to result in cell death, whereby the basis is provided, which can explain the anti-tumor effect as previously determined.

8. Determination of Anti-Tumor Effect Using C57BL/6 Mouse Model Introduced by Melanoma Cell Lines (B16-F10)

In order to confirm the in vivo anti-tumor effect of Ad-peptide-PPR complexes in an animal model allowing for growth of virus and having the preserved immune system, B16-F10 (5×10$^5$ cells/50 µl), which is melanoma cell lines, was subcutaneously injected to a mouse to prepare an animal model. Then, when the size of tumor reached about 100 mm$^3$, the size of tumor was observed for 14 days, while repeatedly administrating the complexes formed by reacting Ad DNA (1 µg) expressing IL-12 and GMCSF and peptide (weight ratio of Ad DNA:peptide; 1:0.5 or 1:1), followed by reaction with PPR each day. Next, to observe changes in tumor tissues by Ad-peptide-PPR complexes, the H & E staining was performed using the mouse melanoma tumor model. When the tumor size reached 50-75 mm$^3$, Ad DNA, Ad-PPR, or Ad-peptide-PPR complexes (weight ratio 1:1:30) were administered into the tumor tissues every other day and Day 2 after the last dose, the tumor tissues were observed.

Figure 31:
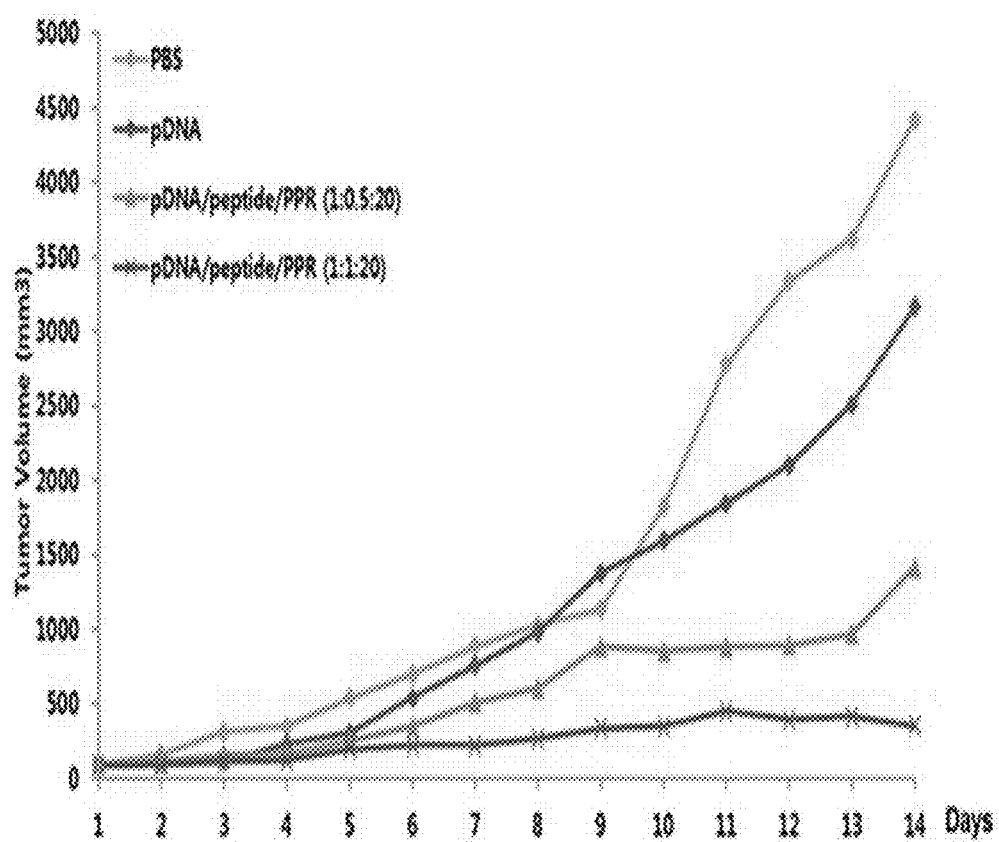
FIG. 31 is a result determining in vivo anti-tumor effect of Ad-peptide-PPR complexes via change in the tumor size using the C57BL/6 mouse model introduced by melanoma cell lines.

As a result, as shown in FIG. 31, it could be seen that in the case of PBS, the size of tumor was 4417.8 mm$^3$, and thus the tumor had been continuously grown, while in the case of being treated with Ad DNA, the size of tumor was 3162.5 mm$^3$, so that it was reduced 29%. In particular, when treated with Ad-peptide-PPR complexes, the size of tumor was confirmed to be 1413.3 mm$^3$ (weight ratio of Ad DNA: peptide of 1:0.5), or 354.6 mm$^3$ (weight ratio of Ad DNA: peptide of 1:1), whereby the size of tumor is each reduced 68%, or 92% compared to the group treated with PBS. Furthermore, it could be confirmed that when treated with Ad-peptide-PPR complexes (weight ratio; 1:1), the size of tumor was reduced 89% compared to the group treated with Ad DNA only, whereby the excellent anti-tumor effect of Ad-peptide-PPR complexes could be verified. In particular, as mentioned above, the present experiment, which is performed in the animal model having the preserved immunity, shows that the strong anti-tumor immune reaction by the complex expressing IL-12 and GMCSF genes synergistically acts together with the anti-tumor effect of Ad DNA-peptide-PPR complexes themselves to improve the anti-tumor effect.

Figure 32:
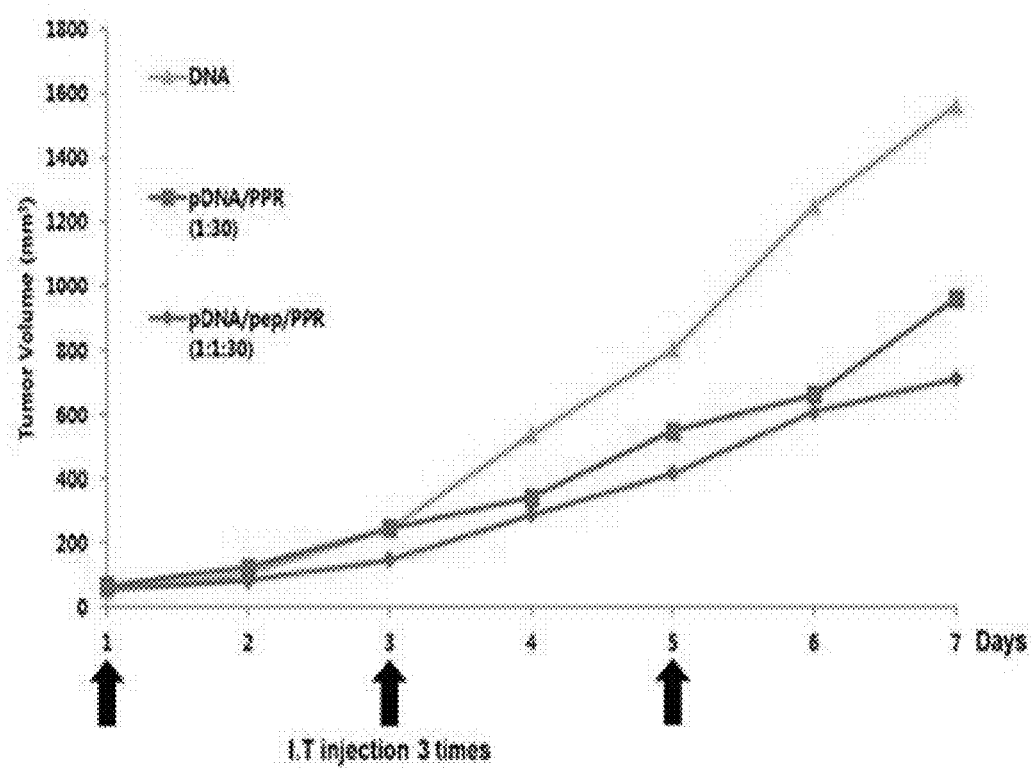
FIG. 32 is a result determining in vivo anti-tumor effect of Ad-peptide-PPR complexes by H & E staining using the C57BL/6 mouse model introduced by melanoma cell lines.
Figure 32:
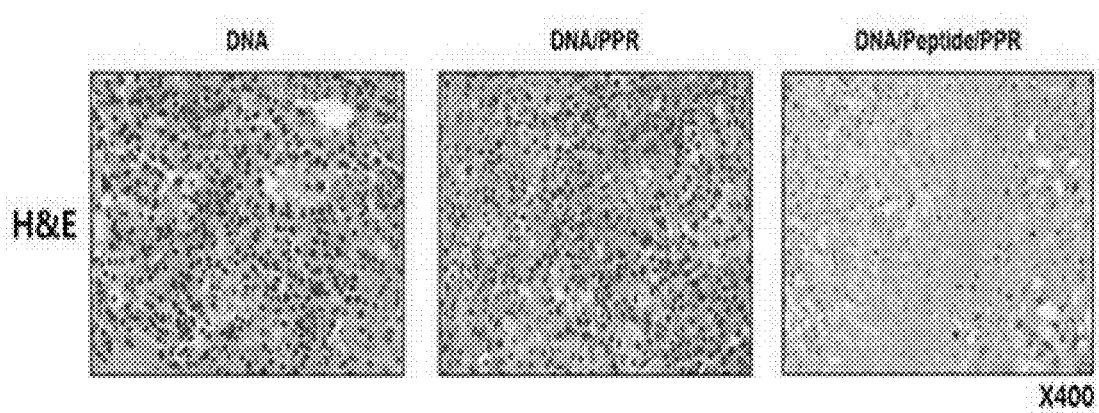

In addition, as shown in FIG. 32, from the H & E staining results, the outstandingly increased cell necrosis could be observed in the group treated with Ad-peptide-PPR complexes compared to the group treated with Ad DNA, or Ad-PPR complexes.

9. Determination of Anti-Tumor Effect Using Hamster Model Introduced by Pancreatic Cancer Cell Lines (HapT1)

9-1. Changes in Tumor Size

In order to confirm the in vivo anti-tumor effect of Ad-PPR or Ad-peptide-PPR complexes in a hamster allowing for growth of virus and having the preserved immune system, hamster pancreatic cancer cell line HapT1 (3×10$^6$ cells/50 µl) was subcutaneously injected to the hamster to prepare a tumor model. Then, when the size of tumor reached about 100 mm$^3$, the size of tumor was observed for 25 days, while repeatedly administrating PBS, Ad DNA, Ad DNA/PPR (1, 2, 4 µg) or Ad DNA/peptide/PPR (1, 2, 4 µg) in the total 5 times intratumorally each other day.

Figure 33:
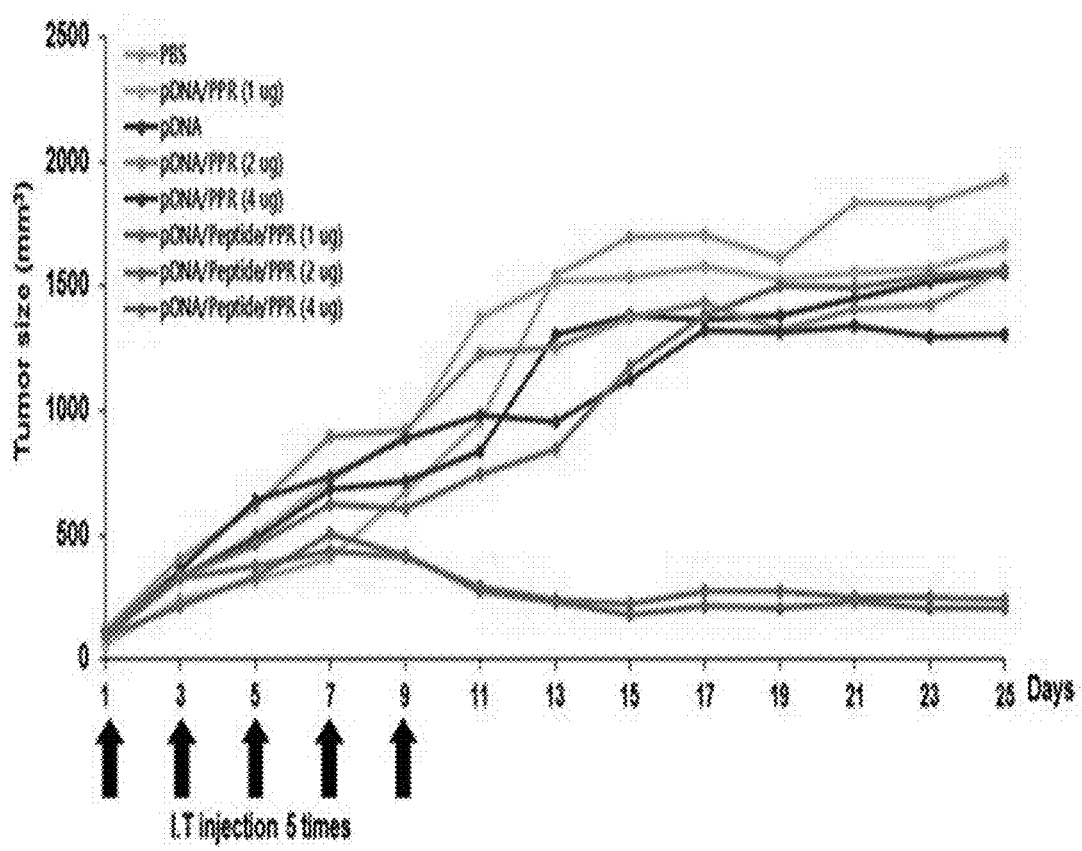
FIG. 33 is a result determining in vivo anti-tumor effect of Ad-PPR or Ad-peptide-PPR complexes via change in the tumor size using the hamster model introduced by pancreatic cancer cell lines.

As a result, as shown in FIG. 33, the size of tumor in the group treated with PBS was 1933.3 mm³ after 25 days, and thus the tumor had been continuously grown, and in the case of the group treated with Ad-PPR complexes, as the dose of DNA increased to 1, 2, 4 µg, the size decreased to 1663.3, 1572.7, 1309.4 mm³, so that the tendency could be confirmed, which increases the anti-tumor effect dose-dependently. Even in the case of Ad-peptide-PPR complexes, as the dose of DNA increased to 1, 2, 4 µg, the size of tumor was observed to be each 1566.3 mm³, 245.2 mm³, 207.7 mm³, and in particular, inter alia, in the group treated with Ad DNA by 2 µg, or 4 µg, the growth of tumor was effectively inhibited until 25 days, so that it could be confirmed that the size of tumor was reduced 84% compared to Ad-PPR complexes.

9-2. Change in Expression Level of Therapeutic Genes

To determine expression levels of therapeutic genes expressed by oncolytic Ad DNA in the tumor tissues treated with Ad-peptide-PPR complexes, the tumor tissues treated with Ad-peptide-PPR complexes, and the like were extracted to progress ELISA for GM-CSF of a therapeutic gene.

Figure 34:
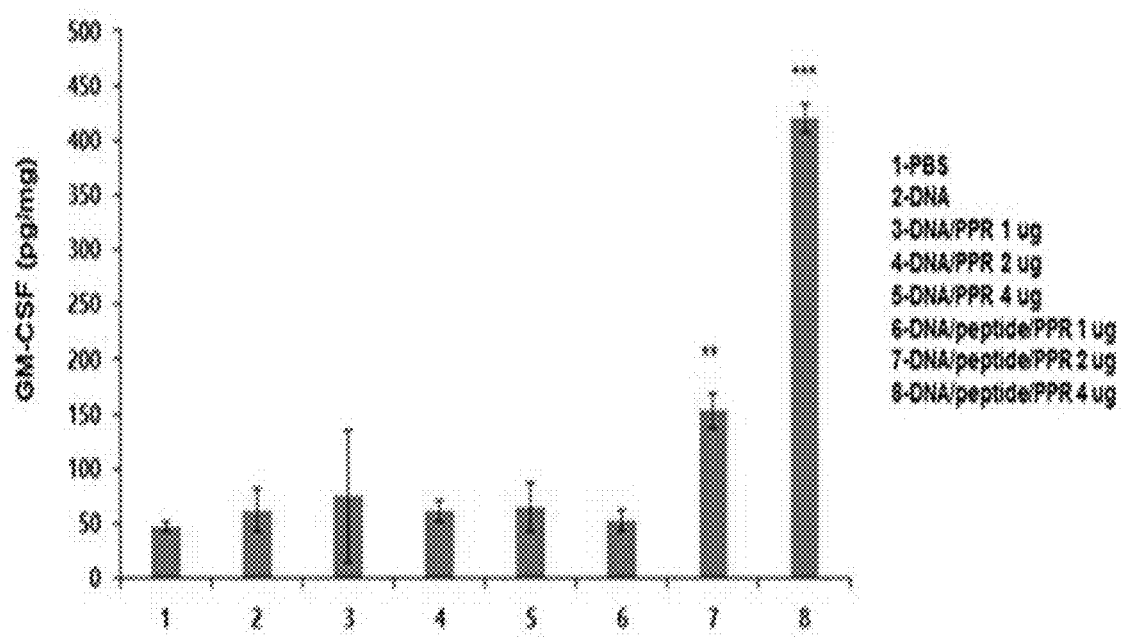
FIG. 34 is a result determining the expression level change of GM-CSF in the tumor tissues treated with Ad-peptide-PPR complexes.

As a result, as shown in FIG. 34, in the group treated with Ad-peptide-PPR complexes (4 µg), the expression of GM-SCF outstandingly increased to 420 pg/mg compared to the group treated with PBS (47 pg/mg), Ad DNA (62 pg/mg), Ad-PPR complexes (65 pg/mg), which increased about 9 times compared to the group treated with PBS. These results mean that when the complexes are formed together using peptide and PPR, intratumoral introduction and selective growth and replication of oncolytic Ad DNA are improved, and consequently, the GM-CSF expression expressed by oncolytic Ad DNA also increases.

9-3. Changes in Various Organs

In order to determine the presence or absence of hepatotoxicity according to administration of Ad-peptide-PPR complexes, liver was extracted from the hamster confirming the anti-tumor effect, from which the presence or absence of toxicity was determined through type analysis and weight confirmation. Furthermore, spleen is a major portion that the immune response to the antigen delivered into blood occurs, where a phenomenon that the larger the size of tumor is, the larger the size of spleen is, appears, and lymph node is an organ that the captured antigens are delivered and activation of the major B cells and T cells occurs, which is enlarged, in general, as a result of the anti-tumor immune reaction. In addition, immunosuppressive factors such as Treg, VEGF, and TGF-β inhibit the growth of thymocytes to induce regression of thymus, where if the anti-tumor immune reaction actively occurs to decrease the size of tumor, the size and weight of thymus are maintained, but as the anti-tumor immune reaction is inhibited to increase the size of tumor, thymus is generally degraded to reduce its size. Based on these facts, spleen, draining lymph nodes (DLNs) and thymus, which are immune reaction mediated organs, were extracted, from which changes according to treatment of Ad-peptide-PPR complexes were observed.

Figure 35A:
FIGS. 35A-35B are views evaluating hepatocyte toxicity according to administration of Ad-peptide-PPR complexes, where
Figure 35B:
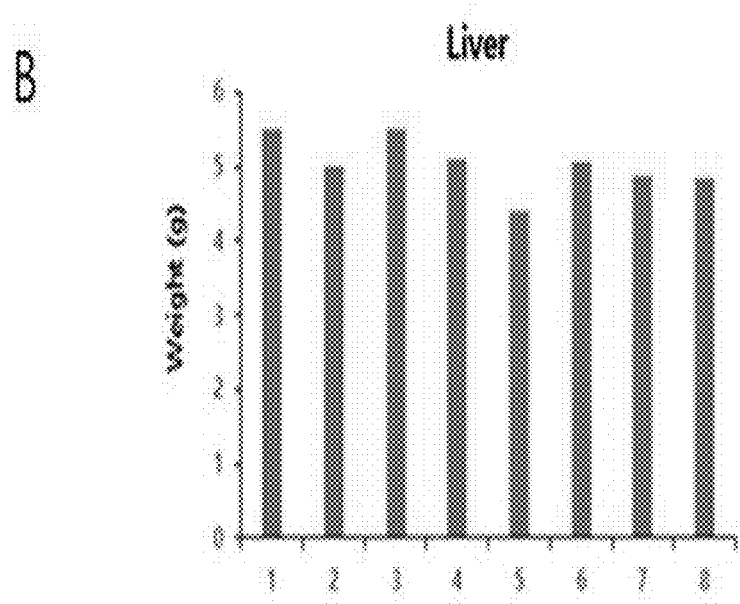
Figure 36A:
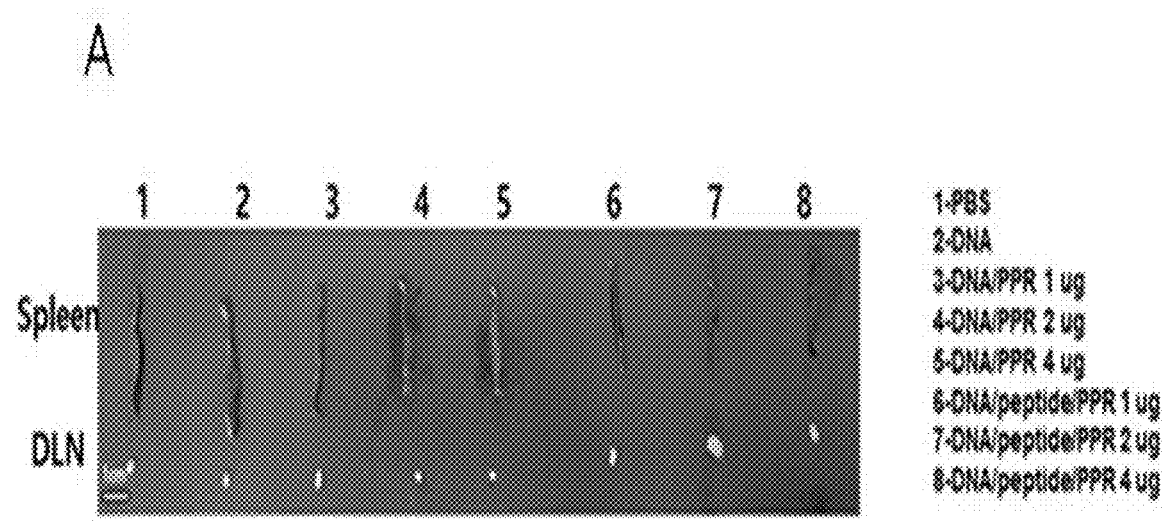
FIGS. 36A-36B are views determining changes in spleen and lymph nodes according to administration of Ad-peptide-PPR complexes, where
Figure 36B:
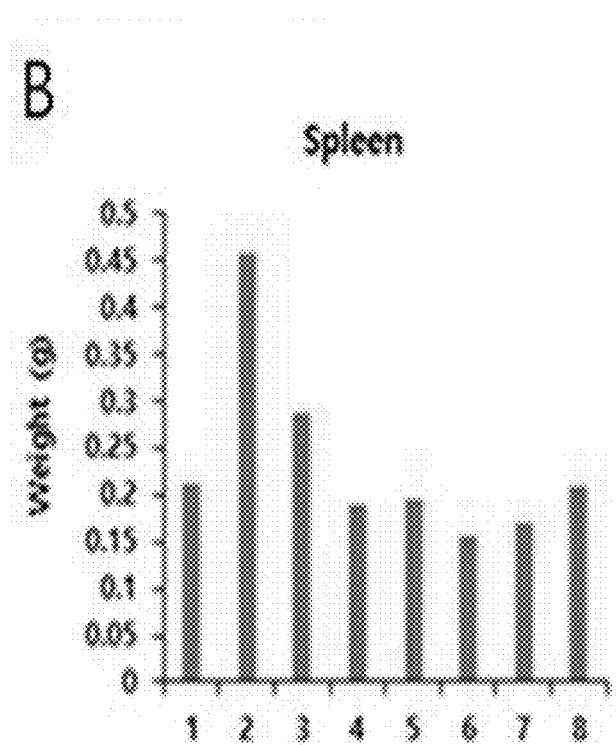
Figure 36C:
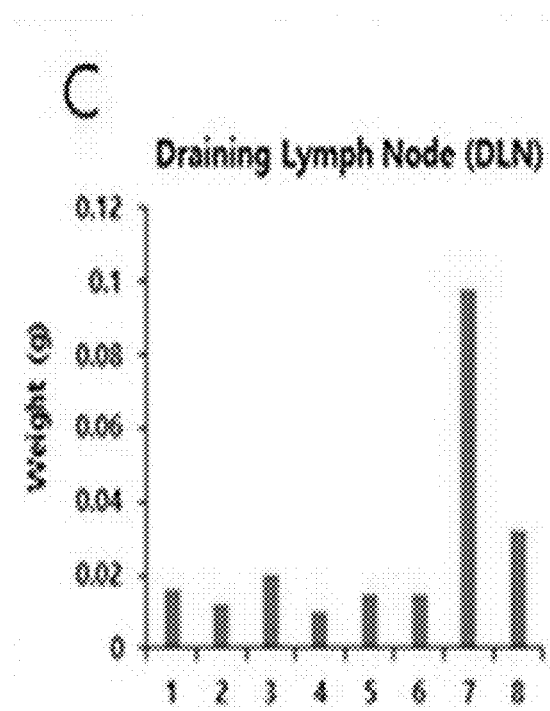
FIG. 36C is a result measuring the weight of lymph nodes.
Figure 37A:
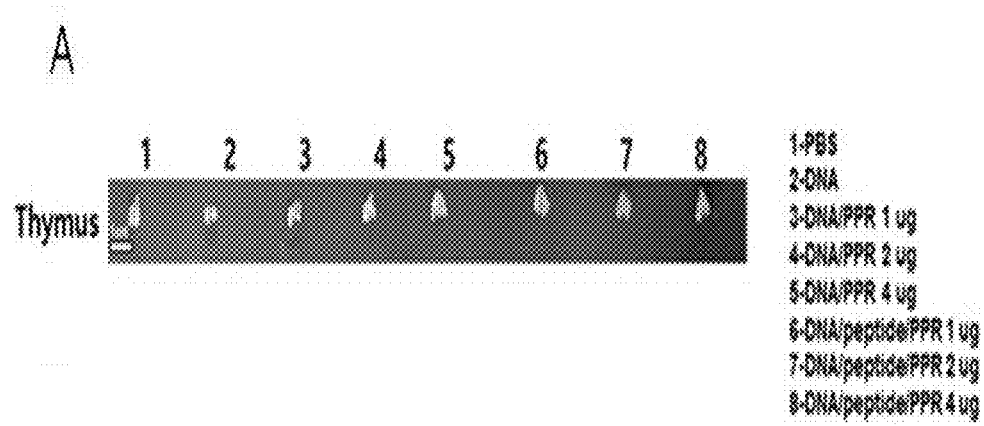
FIGS. 37A-37B are views determining change of thymus according to administration of Ad-peptide-PPR complexes, where
Figure 37B:
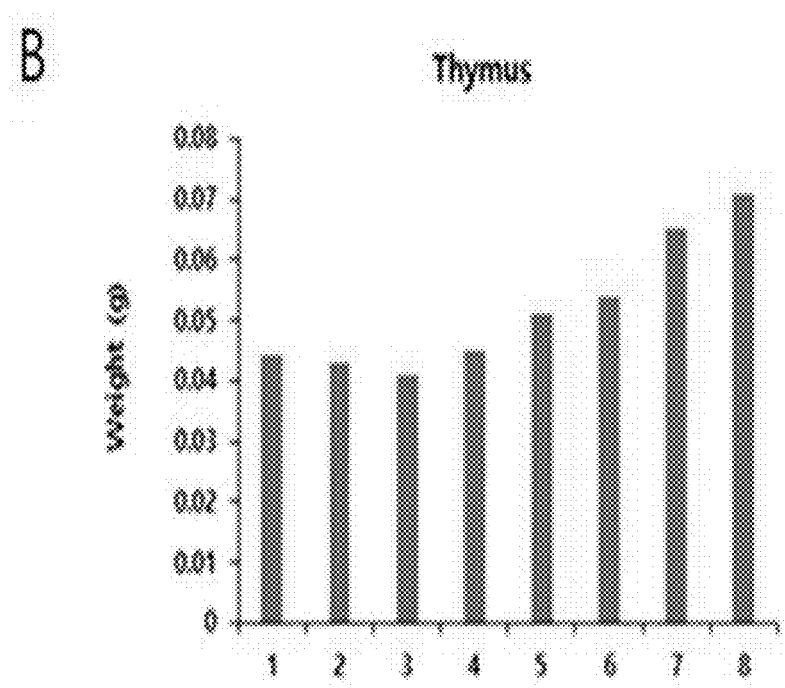

As a result, as shown in FIG. 35, no lesion by hepatotoxicity was observed in the group treated with Ad-peptide-PPR complexes. However, there was a tendency that the weight of liver decreases, as the concentration of DNA contained in the complexes increases. In addition, as shown in FIG. 36, in the group treated with Ad-peptide-PPR complexes, it could be observed that the size and weight of spleen were outstandingly reduced and the size and weight of lymph node were apparently increased, whereby the anti-tumor effect and the anti-tumor immune reaction could be determined. Moreover, as shown in FIG. 37, it could be confirmed that in the group treated with Ad-peptide-PPR complexes that the strong anti-tumor effect had been induced, the size and weight of thymus were maintained, but in the case of the group treated with PBS, Ad DNA that the anti-tumor effect had been slight, thymus was degraded. These results shows that Ad DNA-peptide PPR complexes induced the strong anti-tumor effect through active anti-tumor immune reactions.

9-4. Determination of Anticancer Immune Effect

PBS, Ad DNA, Ad DNA/PPR (1, 2, 4 µg) or Ad DNA/peptide/PPR (1, 2, 4 µg) was intratumorally administered to a pancreatic cancer hamster model each other day in a total of 5 times, and then on Day 16, the tumor was extracted to confirm the presence of CD4+, CD8+ T cells via immunochemical staining Next, to confirm cancer cell killing ability of Ad-peptide-PPR complexes in the tumor tissues, TUNEL assay was performed, and to determine whether the generation of adenoviruses results in the anti-tumor effect of Ad-peptide-PPR complexes, the immunochemical staining was performed using an antibody specific to the adenovirus capsid protein.

Figure 38:
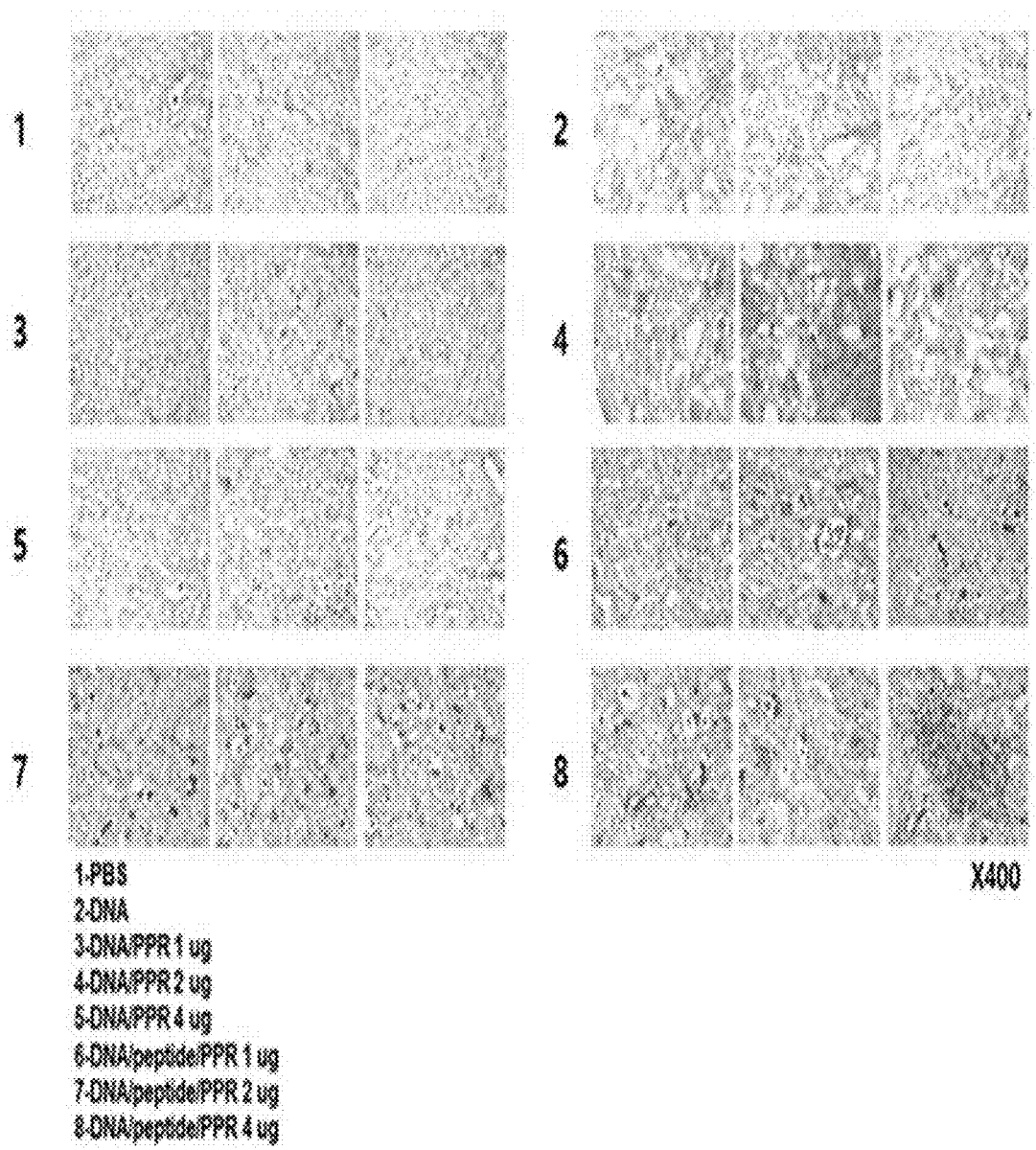
FIG. 38 is a result determining change of the number of CD4+ T cells according to administration of Ad-peptide-PPR complexes via immunochemical staining.
Figure 39:
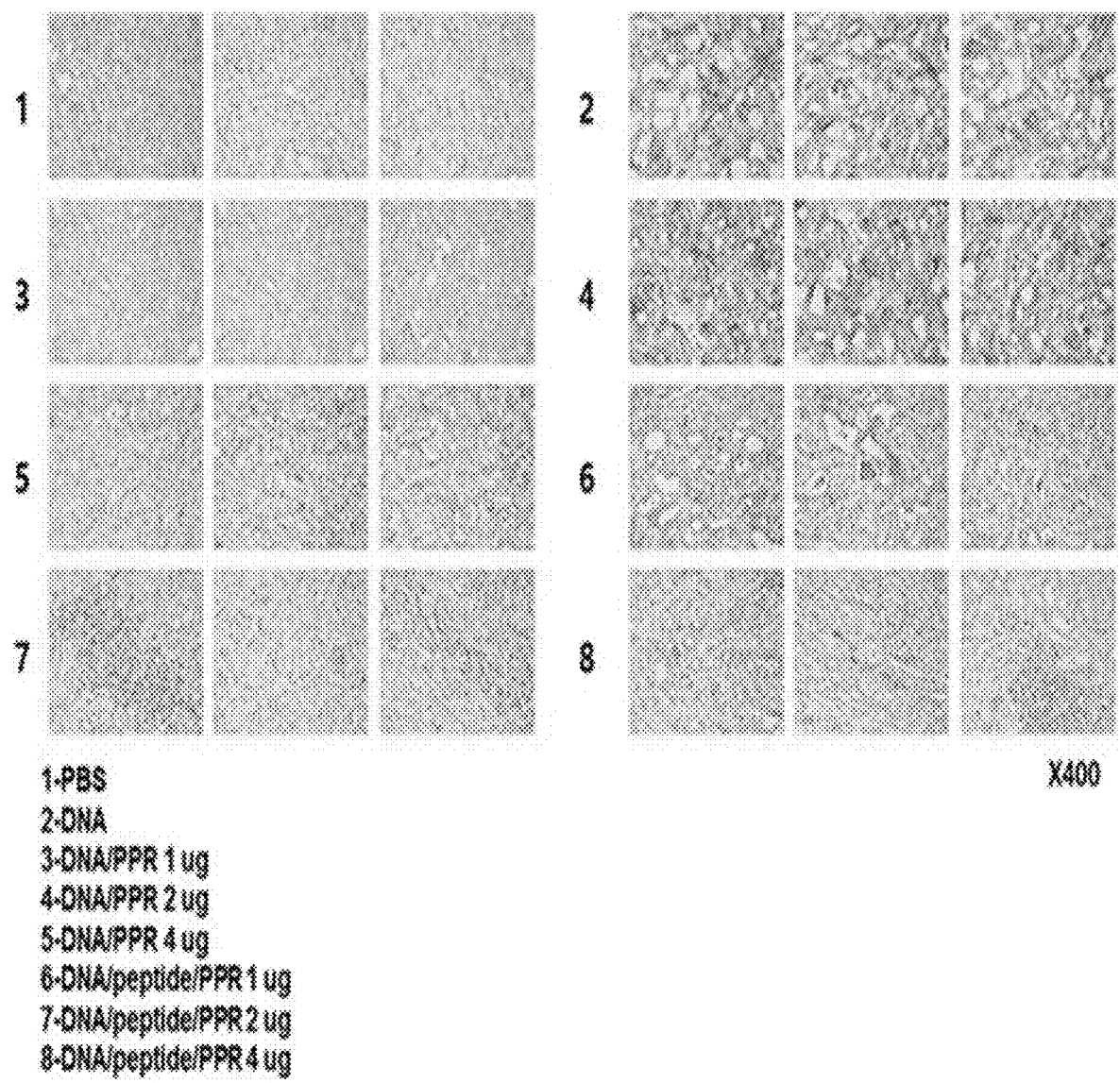
FIG. 39 is a result determining change of the number of CD8+ T cells according to administration of Ad-peptide-PPR complexes via immunochemical staining.
Figure 40:
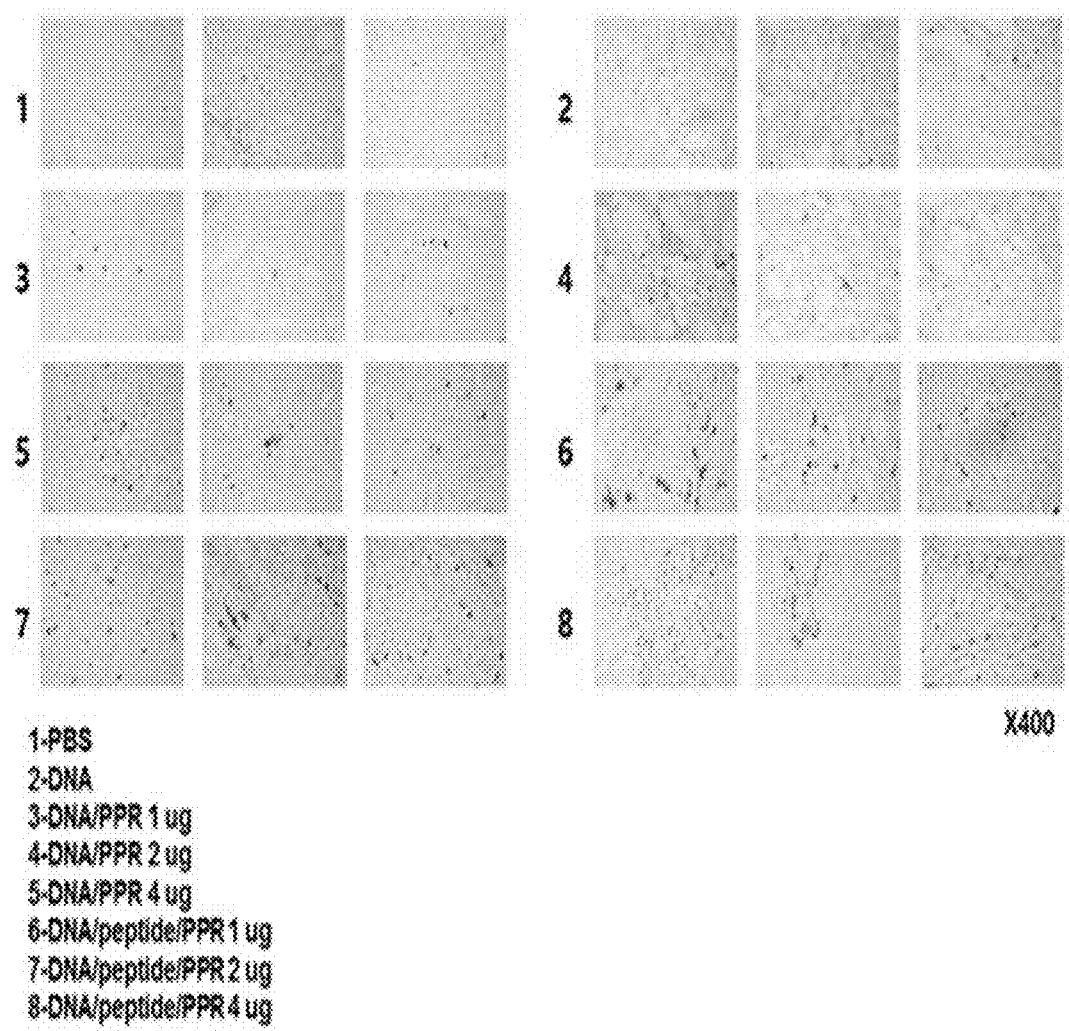
FIG. 40 is a result determining cancer cell killing ability in the tumor tissues according to administration of Ad-peptide-PPR complexes via TUNEL assay.
Figure 41:
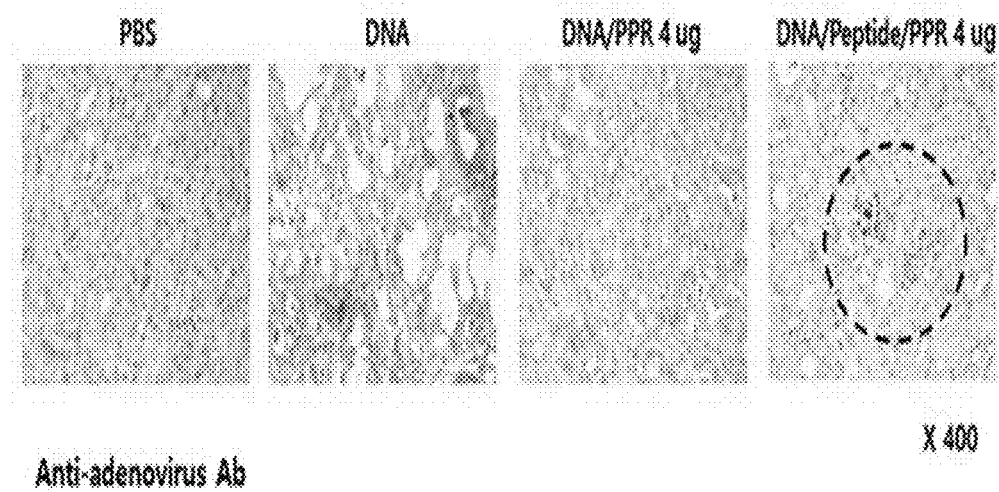
FIG. 41 is a result determining the presence of adenovirus capsid protein in the tumor tissues administered by Ad-peptide-PPR complexes.

As a result, as shown in FIG. 38 and FIG. 39, in the tumor tissues treated with Ad-peptide-PPR complexes, the outstandingly increased CD4+ and CD8+ T cells could be observed, and in particular, in the tumor tissues treated with the Ad-peptide-PPR complexes (2, 4 µg) having an excellent anti-tumor effect, the outstandingly increased CD4+ and CD8+ T cells could be determined. These experimental results mean that the T cell infiltration into the tumor tissues increased due to the strong anti-tumor immune reaction of the Ad-peptide-PPR complexes. In addition, as shown in FIG. 40, in the group treated with Ad-peptide-PPR complexes, the cell necrosis was most actively progressed compared to the group treated with PBS, DNA, and this result shows that Ad DNA was effectively transferred into the tumor tissues by Ad-peptide-PPR complexes to produce viruses, whereby the effective anti-tumor effect appeared. Moreover, as shown in FIG. 41, a large amount of virus particles were observed in the tumor tissues treated with Ad-peptide-PPR complexes, and in particular, the generation of adenovirus particles could be confirmed even after 25 days, whereby it suggests that Ad-peptide-PPR complexes show excellent virus production ability and growth ability in vivo as well as in vitro, so that the strong anti-tumor effect appears.

Hereinabove, the specific parts of the present invention have been described in detail, where it is apparent to those having ordinary knowledge in the art that such specific descriptions are only preferred embodiments, and the scope of the present invention is not limited thereto. Accordingly, the substantial scope of the present invention will be defined by the appended claims and their equivalents.

The invention claimed is:

1. A pH-sensitive and bioreducible polymer, comprising (i) an escapable portion from immune reactions, (ii) a chargeable portion and (iii) a bioreducible portion including disulfide linkages;
   wherein (i) the escapable portion is bound to the chargeable portion; and any one selected from the group consisting of PEG (polyethylene glycol) and mPEG (methoxy polyethylene glycol),
   wherein (ii) the chargeable portion is piperazine or 1-(2-aminoethyl)piperazine,
   wherein (iii) the bioreducible portion is bound to the chargeable portion, and the bioreducible portion is N,N-cystaminebisacrylamide, and
   wherein said polymer has PEI-Arg (polyethyleneimine-arginine) additionally bonded at the end of the bioreducible portion.

2. A polymer-virus complex, having a pH-sensitive and bioreducible polymer comprising (i) an escapable portion from immune reactions, (ii) a chargeable portion having one or more amine groups and (iii) a bioreducible portion including one or more disulfide linkages, wherein the pH-sensitive and bioreducible polymer is bounded to a surface of virus,
   wherein (i) the escapable portion is bound to the chargeable portion; and any one selected from the group consisting of PEG (polyethylene glycol) and mPEG (methoxy polyethylene glycol),
   wherein (ii) the chargeable portion is piperazine or 1-(2-aminoethyl)piperazine, and
   wherein (iii) the bioreducible portion is bound to the chargeable portion, and is N,N-cystaminebisacrylamide.

3. The polymer-virus complex according to claim 2, characterized in that said polymer has PEI-Arg (polyethyleneimine-arginine) additionally bonded at the end of the bioreducible portion.

4. The polymer-virus complex according to claim 3, characterized in that said complex further comprises a peptide of SEQ ID NO: 1.

5. The polymer-virus complex according to claim 2, characterized in that said virus is an oncolytic virus selected from the group consisting of adenovirus, adeno-associated virus (AAV), retrovirus, lentivirus, herpes simplex virus, and vaccinia virus.

* * * * *

SEQUENCE LISTING

<160> NUMBER OF SEQ ID NOS: 3

<210> SEQ ID NO 1
<211> LENGTH: 31
<212> TYPE: PRT

<213> ORGANISM: Artificial Sequence
<220> FEATURE:
<223> OTHER INFORMATION: Peptide

<400> SEQUENCE: 1

Ala Phe Ser Trp Gly Cys Leu Trp Ser Cys Ile Lys Asn Phe Gly Phe
1               5                   10                  15

Cys Gly Ala Leu Ala Glu Arg Lys Lys Arg Gln Arg Arg
            20                  25                  30

<210> SEQ ID NO 2
<211> LENGTH: 3703
<212> TYPE: DNA
<213> ORGANISM: Artificial Sequence
<220> FEATURE:
<223> OTHER INFORMATION: IL-12

<400> SEQUENCE: 2

| | | | | | |
|---|---|---|---|---|---|
| gcaagagaca | cagtcctggg | aaagtctgcc | ggctatccag | acaattataa | aaatgtgtct | 60 |
| cccaaggtca | gcgttccaac | agcctcaccc | tcggcatcca | gcagctcctc | tcagtgccgg | 120 |
| tccagcatgt | gtcaatcacg | ctacctcctc | ttttttggcca | cccttgccct | cctaaaccac | 180 |
| ctcagtttgg | ccagggtcat | tccagtctct | ggacctgcca | ggtgtcttag | ccagtcccga | 240 |
| aacctgctga | gaccacaga | tgacatggtg | aagacggcca | gagaaaaact | gaaacattat | 300 |
| tcctgcactg | ctgaagacat | cgatcatgaa | gacatcacac | gggaccaaac | cagcacattg | 360 |
| aagacctgtt | taccactgga | actacacaag | aacgagagtt | gcctggctac | tagagagact | 420 |
| tcttccacaa | caagagggag | ctgcctgccc | cacagaaga | cgtctttgat | gatgaccctg | 480 |
| tgccttggta | gcatctatga | ggacttgaag | atgtaccaga | cagagttcca | ggccatcaac | 540 |
| gcagcacttc | agaatcacaa | ccatcagcag | atcattctag | acaagggcat | gctggtggcc | 600 |
| atcgatgagc | tgatgcagtc | tctgaatcat | aatggcgaga | ctctgcgcca | gaaacctcct | 660 |
| gtgggagaag | cagaccccta | cagagtgaaa | atgaagctct | gcatcctgct | tcacgccttc | 720 |
| agcacccgcg | tcgtgaccat | caacagggtg | atgggctatc | tgagctccgc | ctgaaagctc | 780 |
| aaggccctct | gccacagcgc | cctcctcaca | cagataggaa | acaaagaaag | attcataaga | 840 |
| gtcaggtggt | cttggcctgg | tgggcttaag | ctccttcagg | aatctgttct | cccatcacat | 900 |
| ctcatctccc | caaggtggc | acagctacct | cagcatggtg | ccctccatcg | cttctctcat | 960 |
| attcactata | caagttgttt | gtaagttttc | atcaaaatat | tgttaagggg | cgaagacgtc | 1020 |
| ctccccctcaa | tgtgttagca | gaagagcaag | aactgataag | ctattgtttt | tgtgccaaag | 1080 |
| tgtttatgaa | acactcagt | caccccttat | ttaaaaatat | ttattgctat | attttatact | 1140 |
| catgaaagta | catgagccta | tttatattta | tttattttct | atttattata | atatttctta | 1200 |
| tcagatgaat | ttgaaacatt | tgaaacata | ccttattttg | tggttctaat | aaagtaatgt | 1260 |
| tatcatagcg | atccgcccct | ctccctcccc | cccccctaac | gttactgcc | gaagccgctt | 1320 |
| ggaataaggc | cggtgtgcgt | ttgtctatat | gttattttcc | accatattgc | cgtcttttgg | 1380 |
| caatgtgagg | gcccggaaac | ctggccctgt | cttcttgacg | agcattccta | ggggtctttc | 1440 |
| ccctctcgcc | aaaggaatgc | aaggtctgtt | gaatgtcgtg | aaggaagcag | ttcctctgga | 1500 |
| agcttcttga | agacaaacaa | cgtctgtagc | gaccctttgc | aggcagcgga | accccccacc | 1560 |
| tggcgacagg | tgcctctgcg | gccaaaagcc | acgtgtataa | gatacacctg | caaaggcggc | 1620 |
| acaaccccag | tgccacgttg | tgagttggat | agttgtggaa | agagtcaaat | ggctctcctc | 1680 |
| aagcgtattc | aacaaggggc | tgaaggatgc | ccagaaggta | ccccattgta | tgggatctga | 1740 |

```
tctgggcct cggtacacat gctttacatg tgtttagtcg aggttaaaaa aacgtctagg    1800
ccccccgaac cacggggacg tggttttcct tttgaaaaac acgatgataa tatggccaca    1860
accgcacatc agaccaggca gctcgcagca aagcaagatg tgtcctcaga agctaaccat    1920
ctcctggttt gccatcgttt tgctggtgtc tccactcatg gccatgtggg agctggagaa    1980
agacgtttat gttgtagagg tggactggac tcccgatgcc cctggagaaa cagtgaacct    2040
cacctgtgac acgcctgaag aagatgacat cacctggacc tcagaccaga gacatggagt    2100
cataggctct ggaaagaccc tgaccatcac tgtcaaagag tttctagatg ctggccagta    2160
cacctgccac aaaggaggcg agactctgag ccactcacat ctgctgctcc acaagaagga    2220
aaatggaatt tggtccactg aaattttaaa aaatttcaaa acaagactt tcctgaagtg    2280 tgaagcacca aattactccg gacggttcac gtgctcatgg ctggtgcaaa gaaacatgga    2340
cttgaagttc aacatcaaga gcagtagcag ttcccctgac tctcgggcag tgacatgtgg    2400
aatggcgtct ctgtctgcag agaaggtcac actggaccaa agggactatg agaagtattc    2460
agtgtcctgc caggaggatg tcacctgccc aactgccgag gagaccctgc ccattgaact    2520
ggcgttggaa gcacggcagc agaataaata tgagaactac agcaccagct tcttcatcag    2580
ggacatcatc aaaccagacc cgcccaagaa cttgcagatg aagcctttga gaactcaca    2640 ggtggaggtc agctgggagt accctgactc ctggagcact ccccattcct acttctccct    2700
caagttcttt gttcgaatcc agcgcaagaa agaaaagatg aaggagacag aggaggggtg    2760
taaccagaaa ggtgcgttcc tcgtagagaa gacatctacc gaagtccaat gcaaaggcgg    2820
gaatgtctgc gtgcaagctc aggatcgcta ttacaattcc tcatgcagca gtgggcatg    2880 tgttccctgc agggtccgat cctaggatgc aacgttggaa aggaaagaaa agtggaagac    2940
attaaggaag aaaaatttaa actcaggatg gaagagtccc ccaaaagctg tcttctgctt    3000
ggttggcttt ttccagtttt cctaagttca tcatgacacc tttgctgatt tctacatgta    3060
aatgttaaat gcccgcagag ccagggagct aatgtatgca tagatattct agcattccac    3120
ttggccttat gctgttgaaa tatttaagta atttatgtat ttattaattt atttctgcat    3180
ttcacatttg tataccaaga tgtattgaat atttcatgtg ctcgtggcct gatccactgg    3240
gaccaggccc tattatgcaa attgtgagct tgttatcttc ttcaacagct cttcaatcag    3300
ggctgcgtag gtacattagc ttttgtgaca accaataaga acataatatt ctgacacaag    3360
cagtgttaca tatttgtgac cagtaaagac ataggtggta tttggagaca tgaagaagct    3420
gtaaagttga ctctgaagag tttagcacta gtttcaacac caagaaagac tttttagaag    3480
tgatattgat aagaaaccag ggccttcttt agaagggtac ctaaatttaa aagaatttg    3540 aaaggctggg tatcggtggt atatgctttt aattccagca ctcaggagac caaggcaggc    3600
agatctctgt gagtttgagg acagcctggt gtacagaggg agttccagca cagccagtgc    3660
cacacagaaa ttctgtctca aaacaatta aaaaaaaaa aaa    3703
```

<210> SEQ ID NO 3
<211> LENGTH: 618
<212> TYPE: DNA
<213> ORGANISM: Artificial Sequence
<220> FEATURE:
<223> OTHER INFORMATION: GM-CSF

<400> SEQUENCE: 3

```
gaaaggctaa ggtcctgagg aggatgtggc tgcagaattt acttttcctg ggcattgtgg     60
```

```
tctacagcct ctcagcaccc acccgctcac ccatcactgt cacccggcct tggaagcatg    120
tagaggccat caaagaagcc ctgaacctcc tggatgacat gcctgtcaca ttgaatgaag    180
aggtagaagt cgtctctaac gagttctcct tcaagaagct aacatgtgtg cagacccgcc    240
tgaagatatt cgagcagggt ctacggggca atttcaccaa actcaagggc gccttgaaca    300
tgacagccag ctactaccag acatactgcc ccccaactcc ggaaacggac tgtgaaacac    360
aagttaccac ctatgcggat ttcatagaca gccttaaaac ctttctgact gatatcccct    420
ttgaatgcaa aaaaccagtc caaaaatgag gaagcccagg ccagctctga atccagcttc    480
tcagactgct gcttttgtgc ctgcgtaatg agccaggaac tcggaatttc tgccttaaag    540
ggaccaagag atgtggcaca gccacagttg gagggcagta taccctctg aaaacgctga     600 ctcagcttgg acagcgga                                                  618
```